US010723753B2

(12) United States Patent
Gray et al.

(10) Patent No.: US 10,723,753 B2
(45) Date of Patent: Jul. 28, 2020

(54) RAS INHIBITORS AND USES THEREOF

(71) Applicant: Dana-Farber Cancer Institute, Inc., Boston, MA (US)

(72) Inventors: Nathanael Gray, Boston, MA (US); Sang Min Lim, San Diego, CA (US); Hwan Geun Choi, Chestnut Hill, MA (US); Kenneth Dale Westover, Southlake, TX (US); Matthew Meyerson, Concord, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/775,162

(22) PCT Filed: Mar. 13, 2014

(86) PCT No.: PCT/US2014/026033
§ 371 (c)(1),
(2) Date: Sep. 11, 2015

(87) PCT Pub. No.: WO2014/160200
PCT Pub. Date: Oct. 2, 2014

(65) Prior Publication Data
US 2016/0046661 A1    Feb. 18, 2016

Related U.S. Application Data

(60) Provisional application No. 61/780,050, filed on Mar. 13, 2013.

(51) Int. Cl.
| | |
|---|---|
| *C07H 19/16* | (2006.01) |
| *C07H 19/207* | (2006.01) |
| *A61K 45/06* | (2006.01) |
| *A61K 31/708* | (2006.01) |
| *C07H 19/167* | (2006.01) |
| *C07F 9/6561* | (2006.01) |
| *C07H 19/20* | (2006.01) |

(52) U.S. Cl.
CPC ........... *C07H 19/16* (2013.01); *A61K 31/708* (2013.01); *A61K 45/06* (2013.01); *C07F 9/65616* (2013.01); *C07H 19/167* (2013.01); *C07H 19/20* (2013.01); *C07H 19/207* (2013.01)

(58) Field of Classification Search
CPC ...... C07H 19/16; C07H 19/20; C07F 9/65616
USPC .......................................................... 514/47
See application file for complete search history.

(56) References Cited

U.S. PATENT DOCUMENTS

2003/0129615 A1   7/2003 Tadeusz et al.
2004/0241706 A1   12/2004 Shah et al.

FOREIGN PATENT DOCUMENTS

| WO | WO 9815563 A1 * | 4/1998 |
|---|---|---|
| WO | WO 9830720 A1 * | 7/1998 |
| WO | WO 03/072757 | 9/2003 |
| WO | WO 2004/024082 | 3/2004 |
| WO | WO 2008/055875 | 5/2008 |
| WO | WO 2013/155223 | 10/2013 |

OTHER PUBLICATIONS

Bamford et al. (Journal of Carbohydrate Chemistry (1996), 15(6), 727-737) (abstract sent).*

(Continued)

*Primary Examiner* — Shaojia A Jiang
*Assistant Examiner* — Michael C Henry
(74) *Attorney, Agent, or Firm* — Wolf, Greenfield & Sacks, P.C.

(57) ABSTRACT

Described herein are compounds of Formulae (I)-(II), and pharmaceutically acceptable salts, and pharmaceutical compositions thereof. Also provided are methods and kits involving the inventive compounds or compositions for treating or preventing proliferative diseases such as cancers (e.g., lung cancer, large bowel cancer, pancreas cancer, biliary tract cancer, or endometrial cancer), benign neoplasms, angiogenesis, inflammatory diseases, autoinflammatory diseases, and autoimmune diseases in a subject.

39 Claims, 10 Drawing Sheets

(56) References Cited

OTHER PUBLICATIONS

STN abstract of Pankiewicz et al.; WO 9815563; Apr. 16, 1998.*
STN abstract of Willis et al.; WO 9830720 A1; Jul. 16, 1998.*
Niewiadomski et al. (Organic & Biomolecular Chemistry (2010), 8(15), 3488-3499) (abstract sent).*
Vollmer et al. (Journal of Biological Chemistry (1994), 269(11), 8082-90) (abstract sent).*
Partial Supplementary European Search Report for EP 14774148.2, dated Oct. 19, 2016.
International Search Report and Written Opinion for PCT/US2014/026033, dated Aug. 28, 2014.
International preliminary Report on Patentability for PCT/US2014/026033, dated Sep. 24, 2015.
Invitation to Pay Additional Fees for PCT/US2014/026033, dated Jun. 18, 2014.
[No Author Listed], PubChem CID 11316586. Create date Oct. 26, 2006. Last accessed May 29, 2014. Accessed at http://pubchem.ncbi.nlm.nih.gov/summary/summary.cgi?cid=11316586&loc=ec_rcs.
Bamford et al., An Improved Method for the Synthesis of GDP-Hexanolamine Derivatives, Key Reagents for the Purification and Characterization of Carbohydrate Processing Enzymes. J Carbohydrate Chemistry. 1996;15(6):727-737.
Berge et al., Pharmaceutical salts. J Pharm Sci. Jan. 1977;66(1):1-19.
Bos, Ras oncogenes in human cancer: a review. Cancer Res. Sep. 1, 1989;49(17):4682-9.
Downward, Targeting RAS signalling pathways in cancer therapy. Nat Rev Cancer. Jan. 2003;3(1):11-22.
Gysin et al., Therapeutic strategies for targeting ras proteins. Genes Cancer. Mar. 2011;2(3):359-72.
Jones et al., Increased frequency of the k-ras G12C mutation in MYH polyposis colorectal adenomas. Br J Cancer. Apr. 19, 2004;90(8):1591-3.
Lim et al., Therapeutic targeting of oncogenic K-Ras by a covalent catalytic site inhibitor. Angew Chem Int Ed. 2014;53:199-204.

Meanwell, Synopsis of some recent tactical application of bioisosteres in drug design. Med Chem. Apr. 28, 2011;54(8):2529-91. doi: 10.1021/jm1013693. Epub Mar. 17, 2011.
Niewiadomski et al., Rationally designed squaryldiamides—a novel class of sugar-nucleotide mimics? Org Biomol Chem. Aug. 7, 2010;8(15):3488-99. doi: 10.1039/c004165c. Epub Jun. 7, 2010.
Patricelli et al., Functional interrogation of the kinome using nucleotide acyl phosphates. Biochemistry. Jan. 16, 2007;46(2):350-8.
Prior et al., A comprehensive survey of Ras mutations in cancer. Cancer Res. May 15, 2012;72(10):2457-67.
Santos et al., Structural and functional properties of ras proteins. FASEB J. Aug. 1989;3(10):2151-63.
Scheffzek et al., The Ras-RasGAP complex: structural basis for GTPase activation and its loss in oncogenic Ras mutants. Science. Jul. 18, 1997;277(5324):333-8.
Vetter et al., The guanine nucleotide-binding switch in three dimensions. Science. Nov. 9, 2001;294(5545):1299-304.
Wang et al., Ras inhibition via direct Ras binding—is there a path forward? Bioorg Med Chem Lett. Sep. 15, 2012;22(18):5766-76.
Wennerberg et al., The Ras superfamily at a glance. J Cell Sci. Mar. 1, 2005;118(Pt 5):843-6.
Vollmer et al., Guanosine 5'-O[-S-(4-bromo-2,3-dioxobutyl)]thiophosphate and adenosine 5'-O-[S-(4-bromo-2,3-dioxobutyl)]thiophosphate. New nucleotide affinity labels which react with rabbit muscle pyruvate kinase. J Biol Chem. Mar. 18, 1994;269(11):8082-90.
Extended European Search Report for EP 14774148.2, dated Jan. 23, 2017.
Ozturk et al. "Guanosina 5'-O-[pS-(3-Bromo-2-oxopropyl)]thiophosphate: A New Reactive Purine Nucleotide Analog Labeling Met-169 and Tyr-262 in Bovine Liver Glutamate Dehydrogenase" Biochemistry 1992, 31, 10544-10555.
Eckstein et al. Synthesis and Properties of Diastereoisomers of Adenosine 5'-(O-1-Thiotriphosphate) and Adenosine 5'-(O-2-Thiotriphosphate), Biochemistry, vol. 15, No. 8, 1976; pp. 1685-1691.

* cited by examiner

1

Cellular Activities of Example of 21 and 22

| $EC_{50}(\mu M)$ | A549(G12S) | H23(G12C) | H358(G12C) |
|---|---|---|---|
| Example 21 | - | 52 | 61 |
| Example 22 | - | 48 | 27 |

Fig. 8

RAS INHIBITORS AND USES THEREOF

RELATED APPLICATIONS

The present application is a national stage filing under 35 U.S.C. § 371 of international PCT application, PCT/US2014/026033, filed Mar. 13, 2014, which claims priority under 35 U.S.C. § 119(e) to U.S. provisional patent application, U.S. Ser. No. 61/780,050, filed Mar. 13, 2013, each of which is incorporated herein by reference.

GOVERNMENT SUPPORT

This invention was made with government support under grant numbers U54HG006097 and RC2CA148164 awarded by The National Institutes of Health. The government has certain rights in the invention.

FIELD OF THE INVENTION

This invention relates to Ras inhibitors. The present invention also provides compositions of the Ras inhibitors and methods of treating proliferative diseases, such as cancer, using the Ras inhibitors.

BACKGROUND OF THE INVENTION

Ras proteins belong to a family of related proteins that are present in all eukaryotic organisms from yeast to human (Santos et al., Structural and functional properties of ras proteins, *FASEB J.* 1989, 3(10), 2151-2163). Ras play a vital role in transducing extracellular cues into diverse cellular responses such as proliferation, apoptosis, and differentiation (Barbacid, M. *Annual review of biochemistry*, 1987, 56, 779). Ras operates as a molecular switch. In its resting (or "off") state, it is found complexed with GDP. In its active (or "on") state, it has GTP bound to it (Vetter et al., *Science,* 2001, 294, 1299). Ras becomes activated when growth factors bind to extracellular receptors which induce nucleotide exchange from GDP to GTP (Vetter et al., *Science,* 2001, 294, 1299). Ras proteins usually possess a slow intrinsic GTPase activity for hydrolysis of GTP to GDP, a reaction that can be enhanced by GTPase activating proteins (GAPs), converting Ras into an inactive signaling state. Mutations which diminish the GTPase activity or induce GAP insensitivity result in constitutively activated signaling pathways, leading to deregulated cell growth, inhibition of cell death, invasiveness, and induction of angiogenesis (Scheffzek et al., *Science,* 1997, 277, 333).

About 30% of all human cancers have been demonstrated to harbor activating Ras mutations (Bos, J. L. *Cancer Research*, 1989, 49, 4682; Prior et al., *Cancer Research*, 2012, 72, 2457). Of the oncogenic Ras family members (H, K, N), K-Ras is most often mutated with most cancer causing mutations located at codons 12, 13, and 61 (Bos, J. L. *Cancer research,* 1989, 49, 4682; Prior et al., *Cancer Research*, 2012, 72, 2457). G12C is a naturally occurring activating K-Ras mutation that is present in roughly 10-20% of all Ras-driven cancers with most cases involving lung, large bowel, pancreas, biliary tract, or uterus (Forbes et al., *Nucleic Acids Research*, 2011, 39, D945; Jones et al., *British Journal of Cancer,* 2004, 90, 1591). This mutation places a solvent-accessible cysteine adjacent to the active site, near the usual position of the gamma-phosphate of the native GTP and results in a constitutively activated K-Ras. Despite more than 20 years of effort in industry and academia, targeting Ras has proven highly elusive (Downward, J. *Nature reviews. Cancer,* 2003, 3, 11; Gysin et al., *Genes & Cancer,* 2011, 2, 359; Wang et al., *J. Bioorganic & medicinal chemistry letters,* 2012, 22, 5766). Therefore, there is a need for new compounds to inhibit Ras for the treatment of diseases associated with aberrant Ras signaling, such as cancer.

SUMMARY OF THE INVENTION

Ras proteins are essential for the regulation of cell growth, proliferation, and differentiation (Barbacid, M. *Annual Review of Biochemistry,* 1987, 56, 779). Ras operates as a molecular switch between the active GTP-bound and the inactive GDP-bound state (Vetter et al., *Science,* 2001, 294, 1299). Mutations of Ras constitutively activate the signaling pathways leading to deregulated cell growth, inhibition of cell death, invasiveness, and induction of angiogenesis. Accordingly, Ras is one of the most common oncogene in human cancer—mutations that permanently activate Ras are found in about 30% of all human tumors (Bos, J. L. *Cancer Research,* 1989, 49, 4682; Prior et al., *Cancer Research*, 2012, 72, 2457). For this reason, this invention is devoted to developing Ras inhibitors for the treatment of proliferative disorders such as cancer.

The present invention provides compounds of Formulae (I)-(II), and pharmaceutically acceptable salts, solvates, hydrates, polymorphs, co-crystals, tautomers, stereoisomers, isotopically labeled derivatives, prodrugs, and compositions thereof. The compounds of Formulae (I)-(II), and pharmaceutically acceptable salts, solvates, hydrates, polymorphs, co-crystals, tautomers, stereoisomers, isotopically labeled derivatives, prodrugs, and compositions thereof, may inhibit the activity of Ras proteins. In certain embodiments, the Ras protein is K-Ras. In certain embodiments, the Ras protein is mutated. In certain embodiments, the Ras protein is a mutant K-Ras. In certain embodiments, the Ras protein is mutant K-Ras G12C. The present invention further provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of Ras in a cell or organism and as therapeutics for the prevention and/or treatment of diseases associated with overactivated Ras and/or aberrant activity of Ras. In certain embodiments, the inventive compounds are used for the prevention and/or treatment of proliferative diseases such as cancers (e.g., lung cancer, large bowel cancer, pancreas cancer, biliary tract cancer, or endometrial cancer), benign neoplasms, angiogenesis, inflammatory diseases, autoinflammatory diseases, and autoimmune diseases in a subject.

In one aspect, the present invention provides compounds of Formula (I):

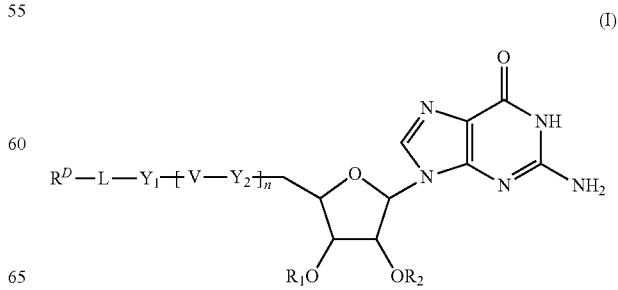

or a pharmaceutically acceptable salt, solvate, hydrate, polymorph, co-crystal, tautomer, stereoisomer, isotopically labeled derivative, or prodrug thereof, wherein $R^D$, L, $Y_1$, $Y_2$, V, $R_1$, $R_2$ and n are as defined herein.

In one aspect, the present invention provides compounds of Formula (I-a):

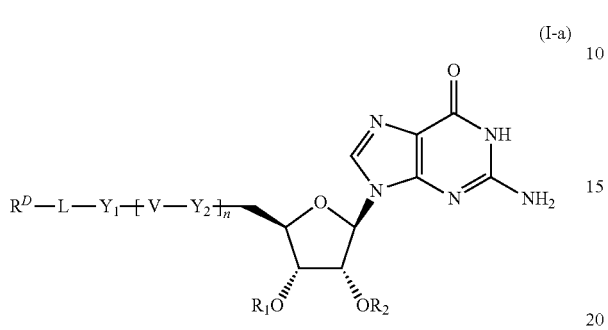

(I-a)

or a pharmaceutically acceptable salt, solvate, hydrate, polymorph, co-crystal, tautomer, stereoisomer, isotopically labeled derivative, or prodrug thereof, wherein $R^D$, L, $Y_1$, $Y_2$, V, $R_1$, $R_2$ and n are as defined herein.

In one aspect, the present invention provides compounds of Formula (I-b):

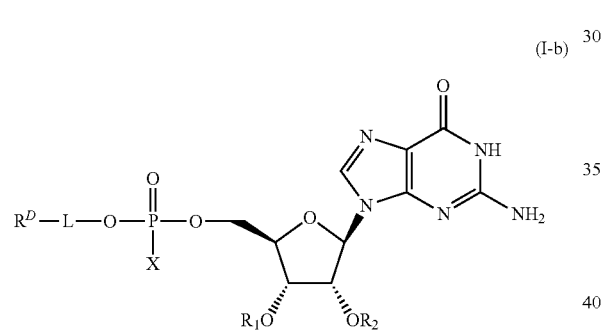

(I-b)

or a pharmaceutically acceptable salt, solvate, hydrate, polymorph, co-crystal, tautomer, stereoisomer, isotopically labeled derivative, or prodrug thereof, wherein $R^D$, L, X, $R_1$, and $R_2$ are as defined herein.

In one aspect, the present invention provides compounds of Formula (I-c):

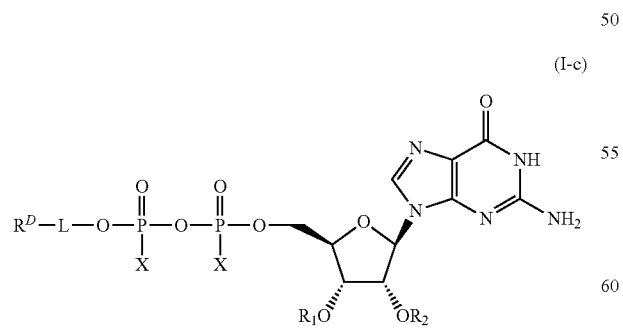

(I-c)

or a pharmaceutically acceptable salt, solvate, hydrate, polymorph, co-crystal, tautomer, stereoisomer, isotopically labeled derivative, or prodrug thereof, wherein $R^D$, L, X, $R_1$, and $R_2$ are as defined herein.

In one aspect, the present invention provides compounds of Formula (I-d):

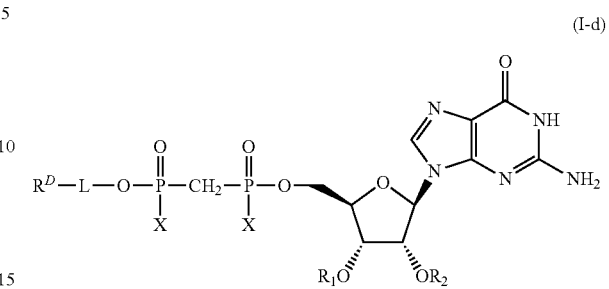

(I-d)

or a pharmaceutically acceptable salt, solvate, hydrate, polymorph, co-crystal, tautomer, stereoisomer, isotopically labeled derivative, or prodrug thereof, wherein $R^D$, L, X, $R_1$, and $R_2$ are as defined herein.

In one aspect, the present invention provides compounds of Formula (I-e):

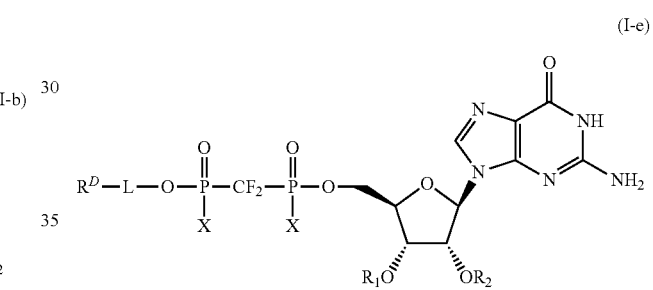

(I-e)

or a pharmaceutically acceptable salt, solvate, hydrate, polymorph, co-crystal, tautomer, stereoisomer, isotopically labeled derivative, or prodrug thereof, wherein $R^D$, L, X, $R_1$, and $R_2$ are as defined herein.

In one aspect, the present invention provides compounds of Formula (I-f):

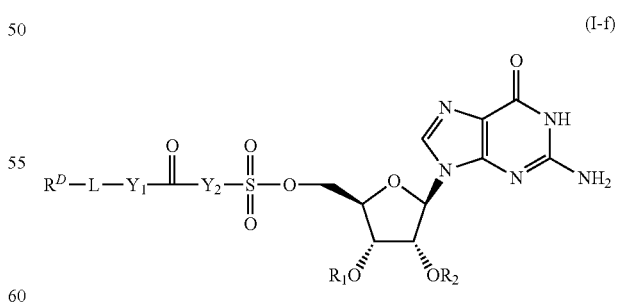

(I-f)

or a pharmaceutically acceptable salt, solvate, hydrate, polymorph, co-crystal, tautomer, stereoisomer, isotopically labeled derivative, or prodrug thereof, wherein $R^D$, L, $Y_1$, $Y_2$, $R_1$, and $R_2$ are as defined herein.

In one aspect, the present invention provides compounds of Formula (II):

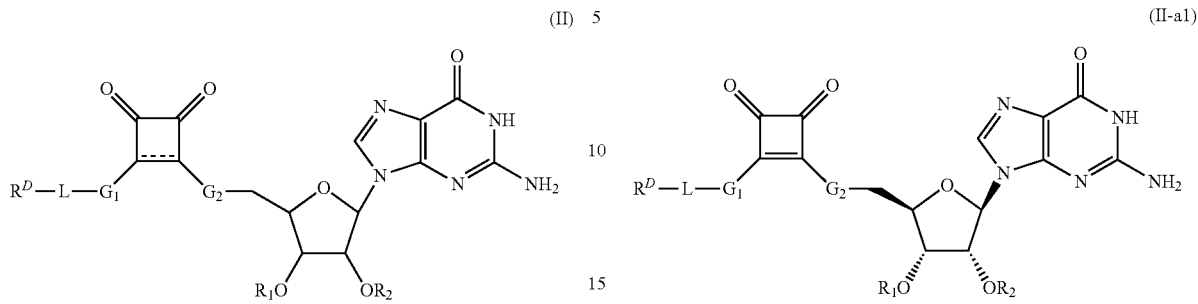

or a pharmaceutically acceptable salt, solvate, hydrate, polymorph, co-crystal, tautomer, stereoisomer, isotopically labeled derivative, or prodrug thereof, wherein $R^D$, L, $G_1$, $G_2$, $R_1$, and $R_2$ are as defined herein.

In one aspect, the present invention provides compounds of Formula (II-a):

In one aspect, the present invention provides compounds of Formula (II-a1):

or a pharmaceutically acceptable salt, solvate, hydrate, polymorph, co-crystal, tautomer, stereoisomer, isotopically labeled derivative, or prodrug thereof, wherein $R^D$, L, $G_1$, $G_2$, $R_1$, and $R_2$ are as defined herein.

In one aspect, the present invention provides compounds of Formula (II-a2):

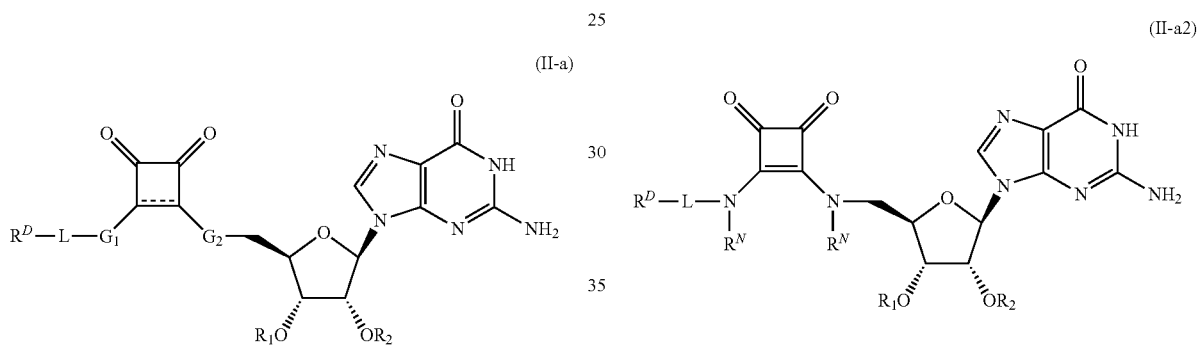

or a pharmaceutically acceptable salt, solvate, hydrate, polymorph, co-crystal, tautomer, stereoisomer, isotopically labeled derivative, or prodrug thereof, wherein $R^D$, L, $G_1$, $G_2$, $R_1$, and $R_2$ are as defined herein.

or a pharmaceutically acceptable salt, solvate, hydrate, polymorph, co-crystal, tautomer, stereoisomer, isotopically labeled derivative, or prodrug thereof, wherein $R^D$, L, $R^N$, $R_1$, and $R_2$ are as defined herein.

Exemplary compounds of Formulae (I)-(II) include, but are not limited to:

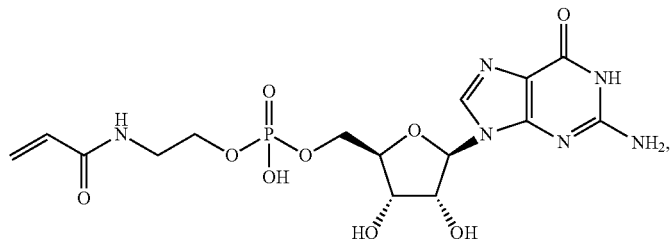

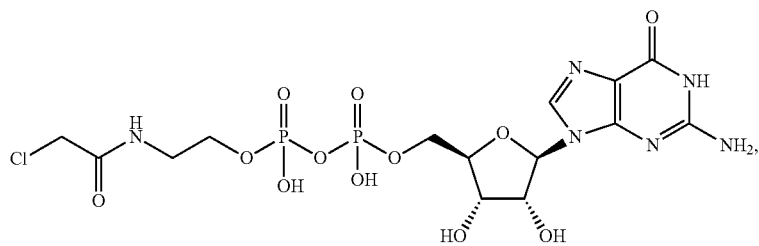

-continued
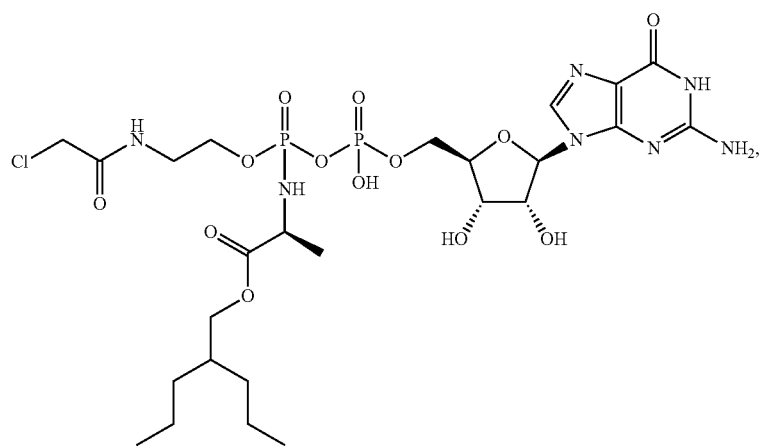
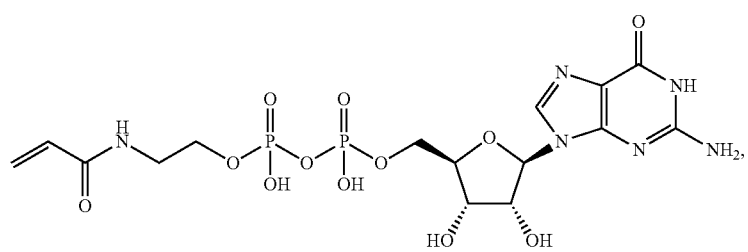
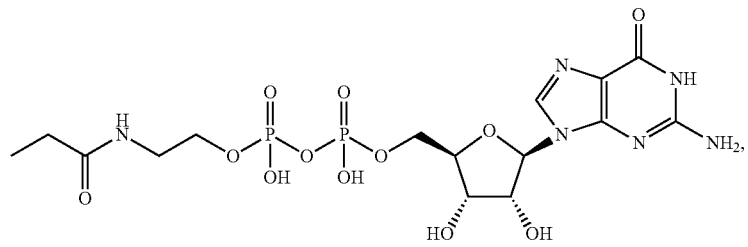
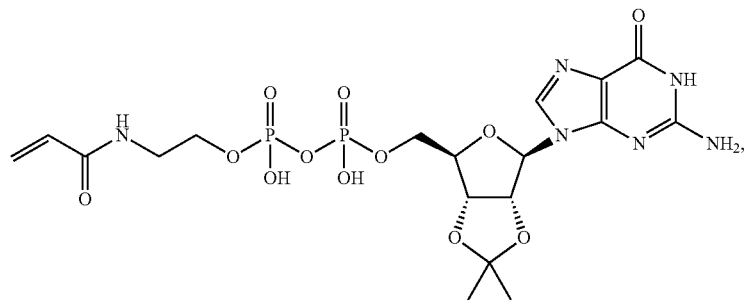
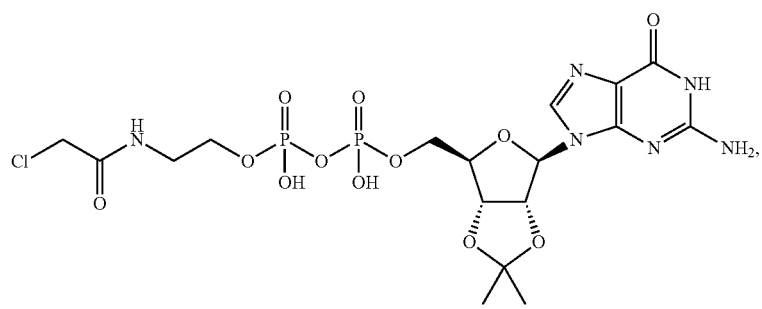

-continued
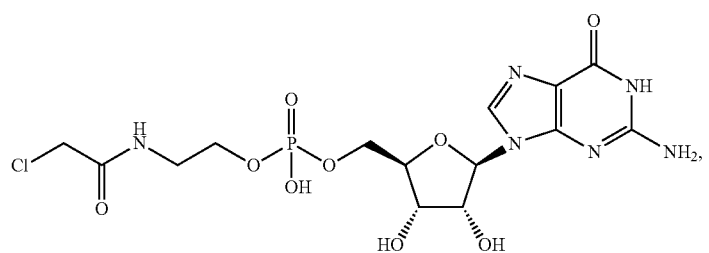
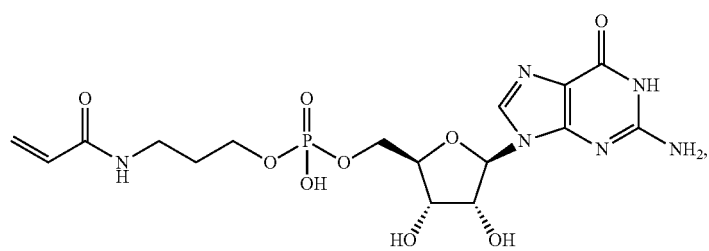
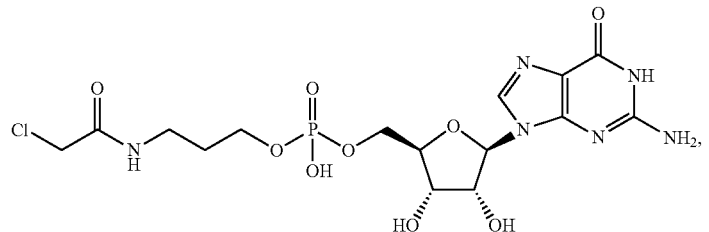
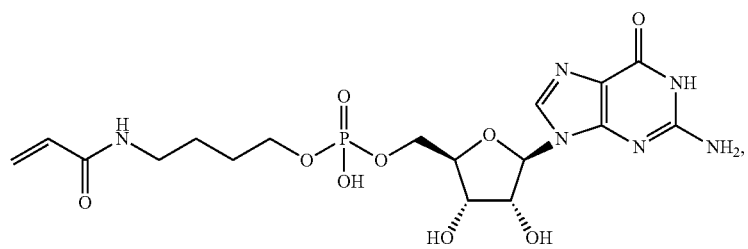
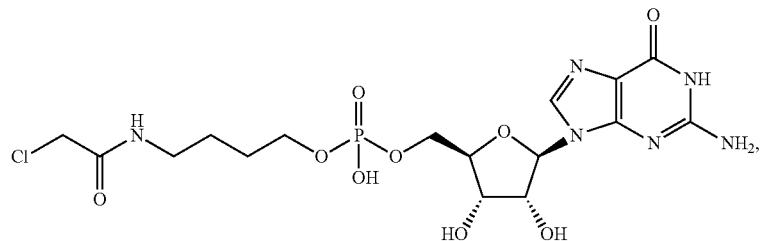
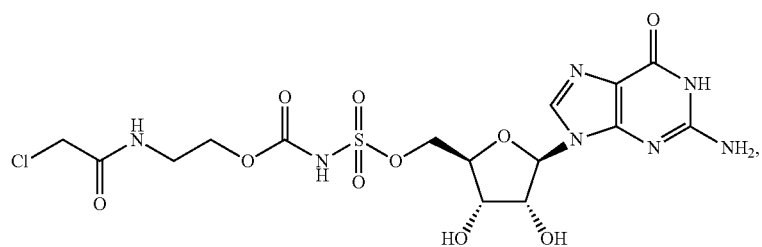

-continued
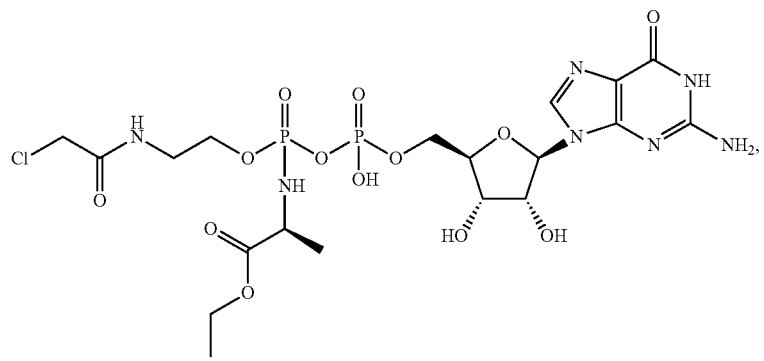
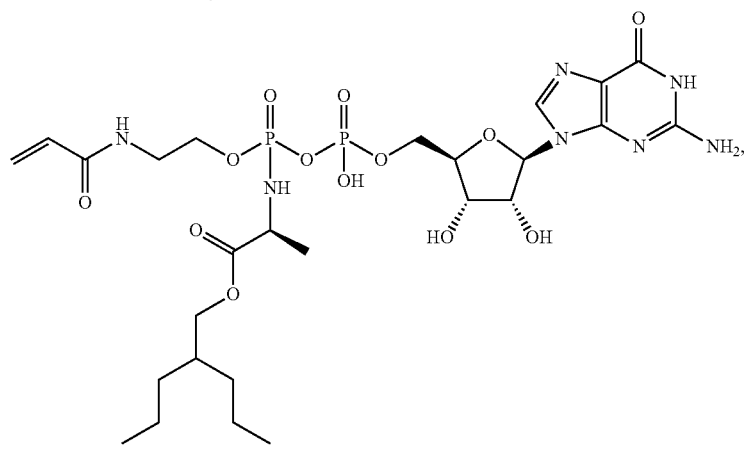
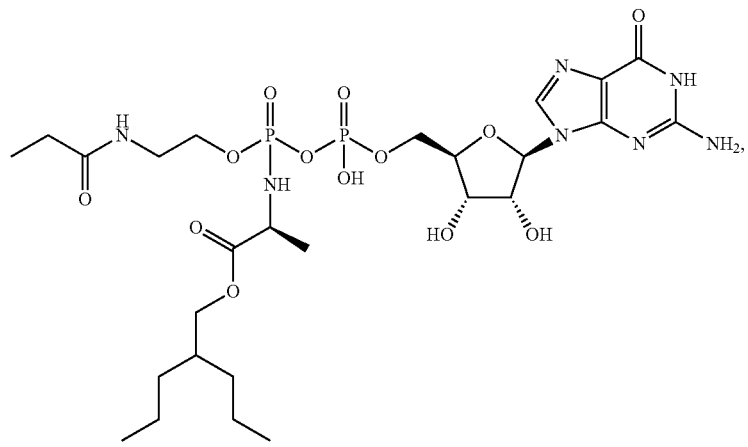
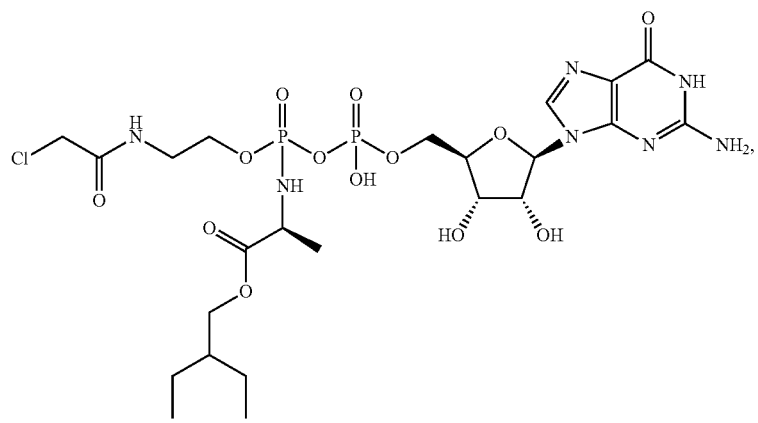

-continued
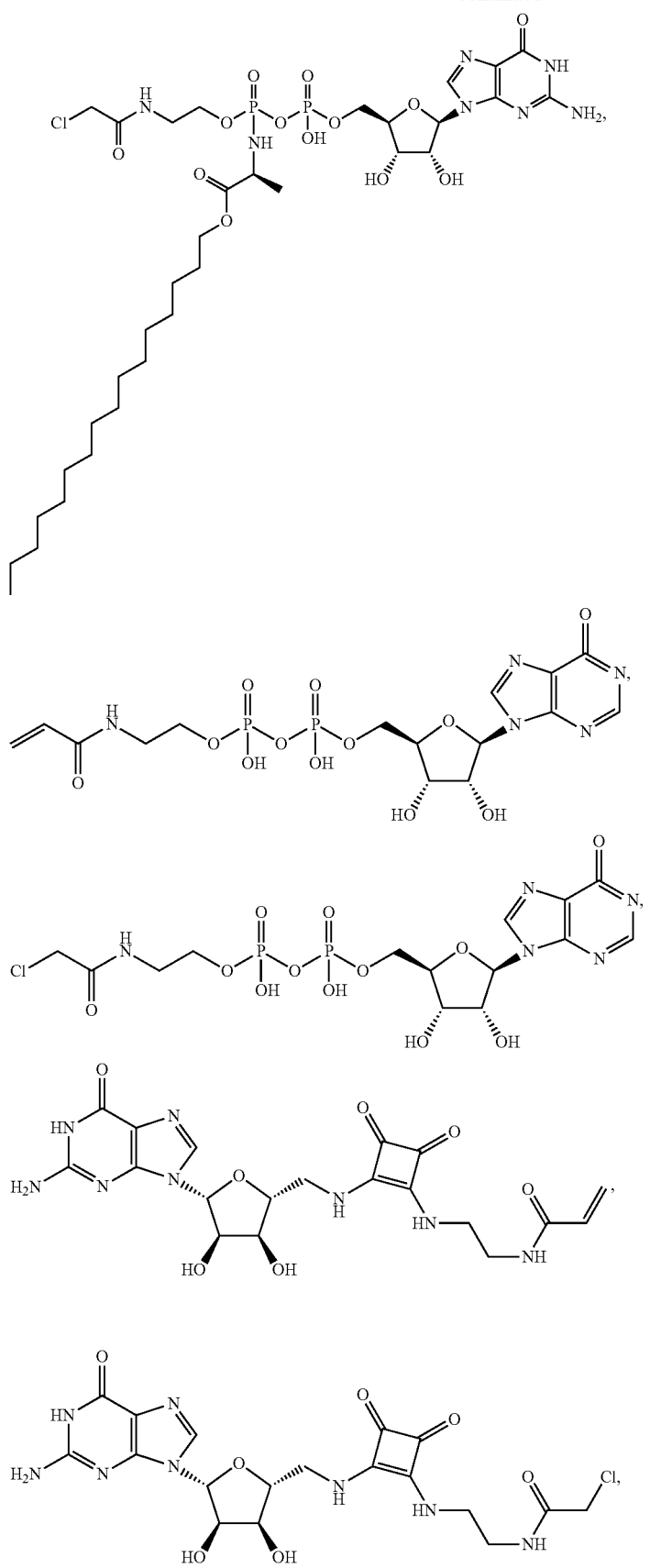

-continued
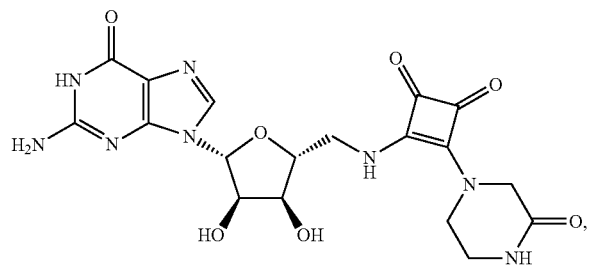
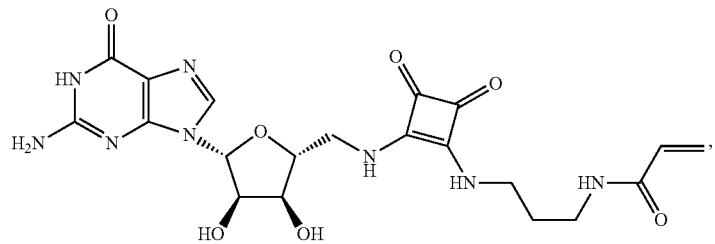
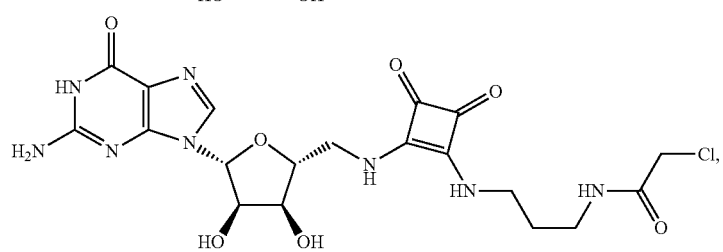
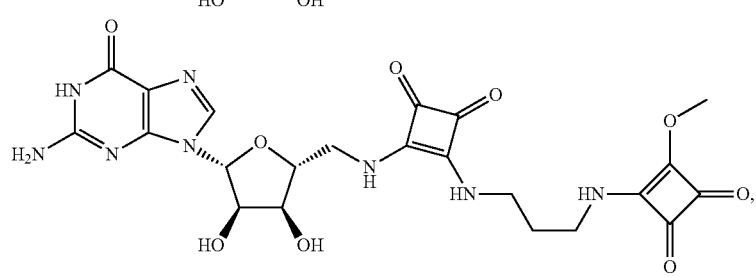
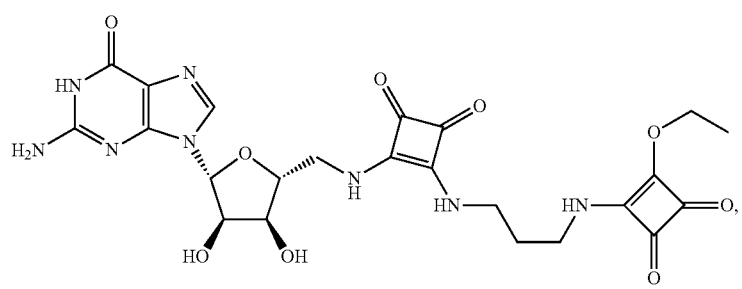
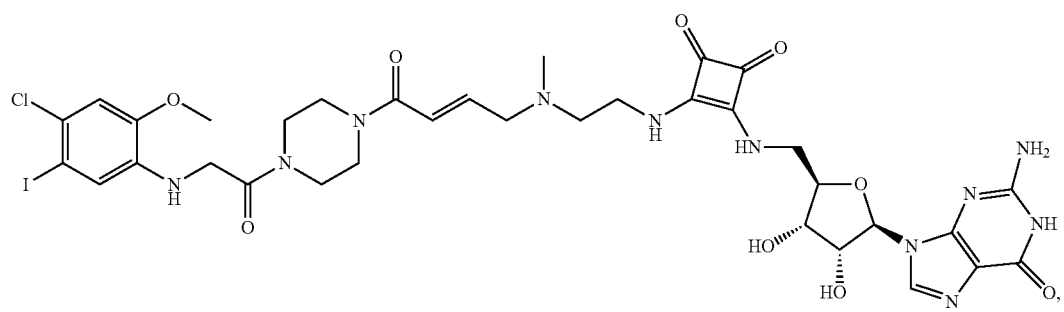 [SMILES: COc1cc(Cl)c(I)cc1NCC(=O)N1CCN(C/C=C/C(=O)NCCNc2c(NC[C@H]3O[C@@H](n4cnc5c(=O)[nH]c(N)nc54)[C@H](O)[C@@H]3O)c(=O)c2=O)CC1]

-continued

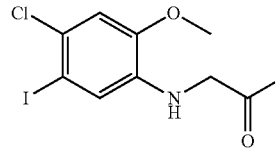 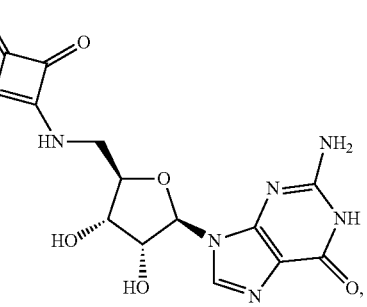

and pharmaceutically acceptable salts, solvates, hydrates, polymorphs, co-crystals, tautomers, stereoisomers, isotopically labeled derivatives, and prodrugs thereof.

In another aspect, the present invention provides pharmaceutical compositions comprising a compound of Formula (I) or Formula (II), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of Formula (I) or Formula (II), or a pharmaceutically acceptable salt, solvate, hydrate, polymorph, co-crystal, tautomer, stereoisomer, isotopically labeled derivative, or prodrug thereof. The pharmaceutical composition may be useful for treating and/or preventing a proliferative disease such as cancer, benign neoplasms, angiogenesis, inflammatory diseases, autoinflammatory diseases, and autoimmune diseases.

Another aspect of the invention relates to methods of inhibiting the activity of Ras in a biological sample or subject. In certain embodiments, the method involves the inhibition of K-Ras. In certain embodiments, the method involves the inhibition of K-Ras G12C mutation.

In another aspect, the present invention provides methods for treating and/or preventing proliferative diseases. Exemplary proliferative diseases include cancer (e.g., leukemia, melanoma, multiple myeloma), benign neoplasm, angiogenesis, inflammatory diseases, autoinflammatory diseases, and autoimmune diseases.

In another aspect, the present invention provides kits comprising a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (I)-(II), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment of proliferative diseases, inflammatory diseases, autoimmune diseases, autoinflammatory diseases, and metabolic diseases. In certain embodiments, the kits described herein further include instructions for administering the compound of Formula (I), or the pharmaceutically acceptable salt, solvate, hydrate, polymorph, co-crystal, tautomer, stereoisomer, isotopically labeled derivative, or prodrug thereof, or the pharmaceutical composition thereof. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

The details of certain embodiments of the invention are set forth herein. Other features, objects, and advantages of the invention will be apparent from the Detailed Description, Figures, Examples, and Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non aromatic cyclic hydrocarbon group having from 3 to 10 ring carbon atoms ("C$_{3-10}$ carbocyclyl") and zero heteroatoms in the nonaromatic ring system. In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocyclic" refers to a radical of a 3- to 14-membered nonaromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$ heteroalkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$ heteroalkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$ heteroalkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)^+X^-$, —$NH_3^+X^-$, —$N(OC_{1-6}$ alkyl$)(C_{1-6}$ alkyl), —$N(OH)(C_{1-6}$ alkyl), —NH(OH), —SH, —$SC_{1-6}$ alkyl, —$SS(C_{1-6}$ alkyl), —C(=O)($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=O)$NH_2$, —C(=O)N($C_{1-6}$ alkyl$)_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl$)_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl$)_2$, —C(=NH)NH($C_{1-6}$ alkyl), —C(=NH)$NH_2$, —OC(=NH)N($C_{1-6}$ alkyl$)_2$, —OC(NH)NH($C_{1-6}$ alkyl), —OC(NH)$NH_2$, —NHC(NH)N($C_{1-6}$ alkyl$)_2$, —NHC(=NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl$)_3$, —OSi($C_{1-6}$ alkyl$)_3$—C(=S)N($C_{1-6}$ alkyl$)_2$, C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl$)_2$, —OP(=O)($C_{1-6}$ alkyl$)_2$, —OP(=O)(O$C_{1-6}$ alkyl$)_2$, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., $F^-$, $Cr^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb})_2$, —OC(=O)$SR^{aa}$, —OC(=O)$R^{aa}$, —$OCO_2R^{aa}$, —OC(=O)N($R^{bb})_2$, —OC(=$NR^{bb}$)$R^{aa}$, —OC(=$NR^{bb}$)$OR^{aa}$, —OC(=$NR^{bb}$)N($R^{bb})_2$, —OS(=O)$R^{aa}$, —$OSO_2R^{aa}$, —OSi($R^{aa})_3$, —OP($R^{cc})_2$, —OP($R^{cc})_3$, —OP(=O)$_2R^{aa}$, —OP(=O)($R^{aa})_2$, —OP(=O)(O$R^{cc})_2$, —OP(=O)$_2$N($R^{bb})_2$, and —OP(=O)(N$R^{bb})_2$, wherein $R^{aa}$, $R^{bb}$, and $R^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —S=$SR^{cc}$, —SC(=S)$SR^{aa}$, —SC(=O)$SR^{aa}$, —SC(=O)$OR^{aa}$, and —SC(=O)$R^{aa}$, wherein $R^{aa}$ and $R^{cc}$ are as defined herein.

As used herein, the term, "amino" refers to the group —$NH_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb})_2$, —NHC(=$NR^{bb}$)N($R^{bb})_2$, —$NHSO_2R^{aa}$, —NHP(=O)(O$R^{cc})_2$, and —NHP(=O)(N$R^{bb})_2$, wherein $R^{aa}$, $R^{bb}$ and $R^{cc}$ are as defined herein, and wherein $R^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb})_2$, —$NR^{bb}$C(=O)$R^{aa}$, —$NR^{bb}CO_2R^{aa}$, —$NR^{bb}$C(=O)N($R^{bb})_2$, —$NR^{bb}$C(=$NR^{bb}$)N($R^{bb})_2$, —$NR^{bb}SO_2R^{aa}$, —$NR^{bb}$P(=O)(O$R^{cc})_2$, and —$NR^{bb}$P(=O)(N$R^{bb})_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N($R^{bb})_3$ and —N($R^{bb})_3^+X^-$, wherein $R^{bb}$ and $X^-$ are as defined herein.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb})_2$, —OC(=O)$SR^{aa}$, —OC(=O)$R^{aa}$, —$OCO_2R^{aa}$, —OC(=O)N($R^{bb})_2$, —OC(=$NR^{bb}$)$R^{aa}$, —OC(=$NR^{bb}$)$OR^{aa}$, —OC(=$NR^{bb}$)N($R^{bb})_2$, —OS(=O)$R^{aa}$, —$OSO_2R^{aa}$, —OSi($R^{aa})_3$, —OP($R^{cc})_2$, —OP($R^{cc})_3$, —OP(=O)$_2R^{aa}$, —OP(=O)($R^{aa})_2$, —OP(=O)(O$R^{cc})_2$, —OP(=O)$_2$N($R^{bb})_2$, and —OP(=O)(N$R^{bb})_2$, wherein $R^{aa}$, $R^{bb}$, and $R^{cc}$ are as defined herein. In the case wherein "substituted hydroxyl" is a ligand $L_1$ or $L_2$, "substituted hydroxyl" also refers to the group ($R^{aa})_2$O, wherein $R^{aa}$ is as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —S=$SR^{cc}$, —SC(=S)$SR^{aa}$, —SC(=O)$SR^{aa}$, —SC(=O)$OR^{aa}$, and —SC(=O)$R^{aa}$, wherein $R^{aa}$ and $R^{cc}$ are as defined herein.

As used herein, the term, "amino" refers to the group —$NH_2$.

As used herein, the term "monosubstituted amino" refers to an amino group wherein the nitrogen atom directly attached to the parent molecule, or coordinated to an iron atom, is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb})_2$, —NHC(=$NR^{bb}$)N($R^{bb})_2$, —$NHSO_2R^{aa}$, —NHP(=O)(O$R^{cc})_2$, and —NHP(=O)(N$R^{bb})_2$, wherein $R^{aa}$, $R^{bb}$ and $R^{cc}$ are as defined herein, and wherein $R^{bb}$ of the group —NH($R^{bb}$) is not hydrogen.

As used herein, the term "disubstituted amino" refers to an amino group wherein the nitrogen atom directly attached to the parent molecule, or coordinated to an iron atom, is substituted with two groups other than hydrogen, and includes groups selected from —N($R^{bb}$)$_2$, —$NR^{bb}$C(=O) $R^{aa}$, —$NR^{bb}$CO$_2R^{aa}$, —$NR^{bb}$C(=O)N($R^{bb}$)$_2$, —$NR^{bb}$C(=$NR^{bb}$)N($R^{bb}$)$_2$, —$NR^{bb}$SO$_2R^{aa}$, —$NR^{bb}$P(=O)(O$R^{cc}$)$_2$, and —$NR^{bb}$P(=O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule, or coordinated to an iron atom, is substituted with three groups, and includes groups selected from —N($R^{bb}$)$_3$ and —N($R^{bb}$)$_3^+$X$^-$, wherein $R^{bb}$ and X$^-$ are as defined herein.

As used herein, the term "sulfonyl" refers to a group selected from —SO$_2$N($R^{bb}$)$_2$, —SO$_2R^{aa}$, and —SO$_2$O$R^{aa}$, wherein $R^{aa}$ and $R^{bb}$ are as defined herein.

As used herein, the term "sulfinyl" refers to the group —S(=O)$R^{aa}$, wherein $R^{aa}$ is as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—CO$_2$H), aldehydes (—CHO), esters (—CO$_2R^{aa}$, —C(=O)S$R^{aa}$, —C(=S)S$R^{aa}$), amides (—C(=O)N($R^{bb}$)$_2$, —C(=O)N$R^{bb}$SO$_2R^{aa}$, —C(=S)N($R^{bb}$)$_2$), and imines (—C(=N$R^{bb}$)$R^{aa}$, —C(=N$R^{bb}$)O$R^{aa}$), —C(=N$R^{bb}$)N($R^{bb}$)$_2$), wherein $R^{aa}$ and $R^{bb}$ are as defined herein.

As used herein, the term "oxo" refers to the group =O, and the term "thiooxo" refers to the group =S.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —$C_{1-10}$ alkyl (e.g., aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(phydroxyphenyl)propanamide, 3-(o-nitrophenyl)propanamide, 2-methyl-2-(onitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-pmethoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, trip-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

As used herein, the term "salt" refers to any and all salts.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, the term "tautomer" refers to particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive. As used herein, a "leaving group" is an art understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502). Exemplary leaving groups include, but are not limited to, halo (e.g., chloro, bromo, iodo) and sulfonyl substituted hydroxyl groups (e.g., tosyl, mesyl, besyl).

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formulae (I)-(II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

As used herein, the term "tautomer" includes two or more interconvertable forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable minor images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I), which have cleavable groups and become by solvolysis or under physiological conditions the compounds of Formula (I)-(II) which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formulae (I)-(II) may be preferred in certain instances.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other nonhuman animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A nonhuman animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formulae (I)-(II) refers to an amount sufficient to elicit a desired biological response, i.e., treating the condition. As will be appreciated by those of ordinary skill in this art, the effective amount of a compound of Formulae (I)-(III) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor. In treating macular degeneration, an effective amount of an inventive compound may improve sight, reduce the risk of vision loss, or prevent central vision loss from worsening.

A "therapeutically effective amount" of a compound of Formulae (I)-(II) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formulae (I)-(II) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm (Stedman's Medical Dictionary, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and growth of new blood vessels. Normal angiogenesis occurs in the body of a healthy subject during wound healing and for restoring blood flow to tissues after injury. The body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can result in new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

As used herein, an "autoimmune disease" refers to a disease arising from an inappropriate immune response in the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppressants, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/ polymyositis, anti-phospholipid antibody syndrome, scleroderma, pemphigus vulgaris, ANCA-associated vasculitis (e.g., Wegener's granulomatosis, microscopic poly-angiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multi-system inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

A "protein" or "peptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

As used herein "inhibition", "inhibiting", "inhibit" and "inhibitor", and the like, refer to the ability of a compound to reduce, slow, halt, or prevent the activity of a particular biological process involving Ras in a cell relative to vehicle.

As used herein, the term "Ras" represents any member of the Ras family of proteins or mutants thereof. Ras family proteins include, but are not limited to, HRAS, KRAS and NRAS, as well as other members of this subfamily as well: DIRAS1; DIRAS2; DIRAS3; ERAS; GEM; MRAS; NKI-RAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; RRAS2 (Wennerberg et al., *The Ras superfamily at a glance, J. Cell. Sci.*, 2005, 118 (Pt 5), 843-846). In certain embodiments, Ras is a mutant Ras. In certain embodiments, Ras is a substantially similar or a homologous form of the Ras family proteins. In certain embodiments, Ras is Ras is a substantially similar or a homologous form of a mutant Ras.

BRIEF DESCRIPTION OF THE DRAWINGS

FIG. 3 demonstrates exclusive covalent labeling of the GN-site of G12C K-Ras (cysteine residue 12).

FIG. 8 shows cellular activities of Example 21 and Example 22.

DETAILED DESCRIPTION OF CERTAIN EMBODIMENTS OF THE INVENTION

Figure 1:
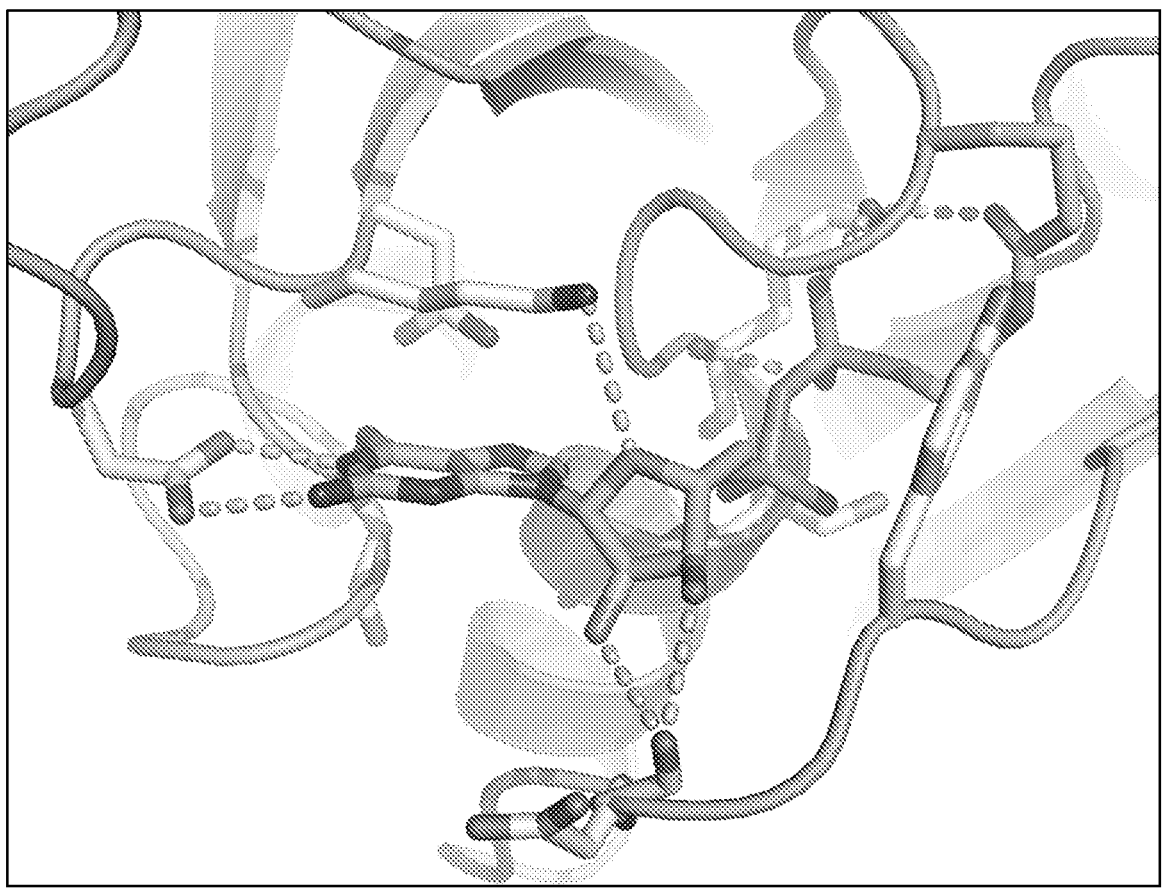
FIG. 1 is a binding model of Compound 1.
Figure 1:
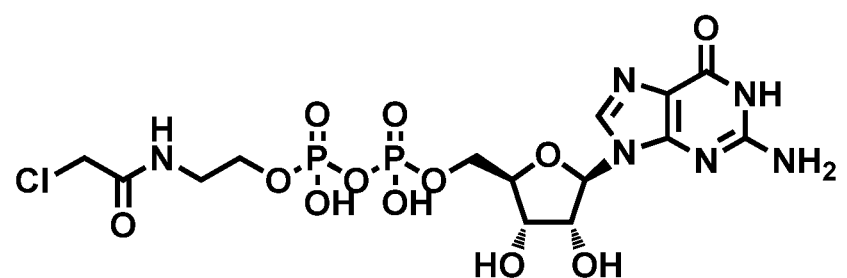
Figure 2:
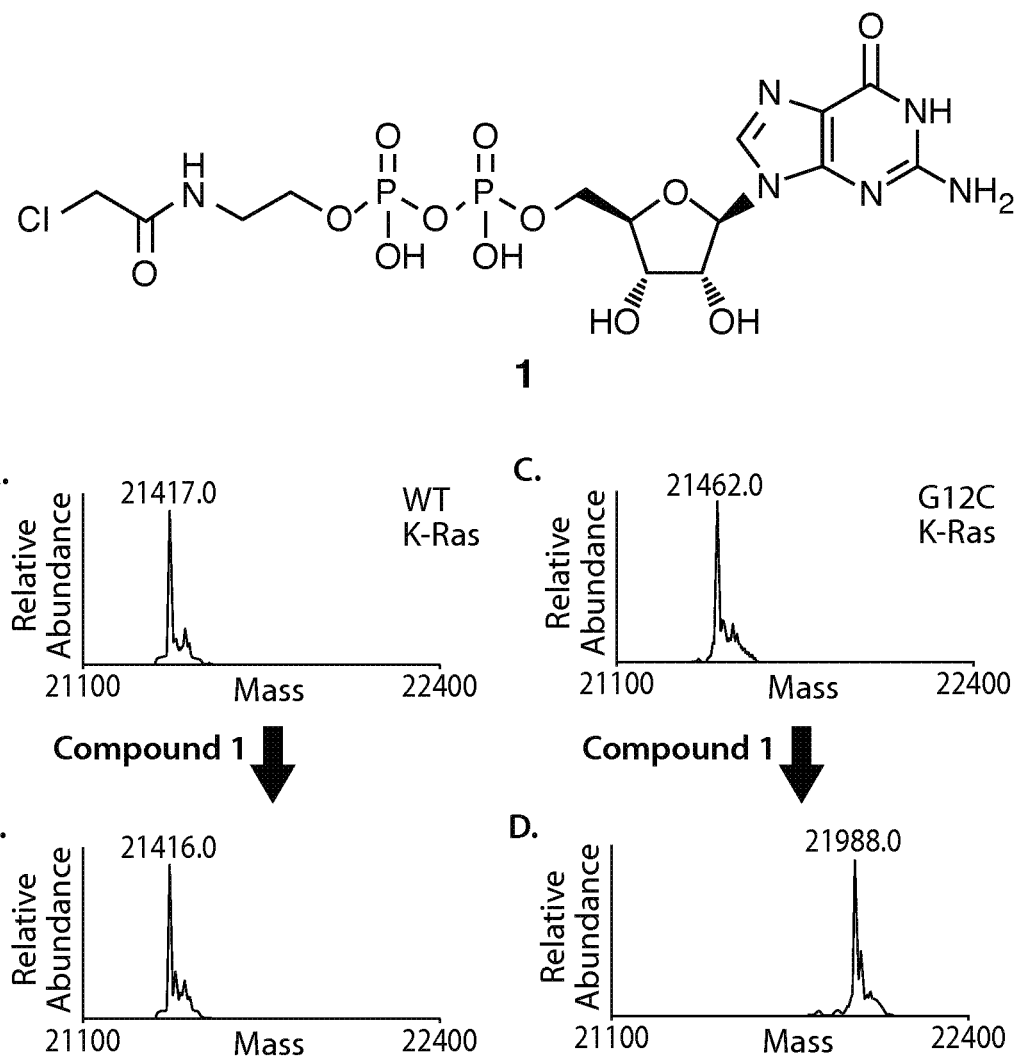
FIG. 2 shows the electrospray ionization mass spectrometry analysis of wild K-Ras (A & B) and K-Ras mutant G12C (C &D) incubated with Compound 1 respectively.
Figure 3:
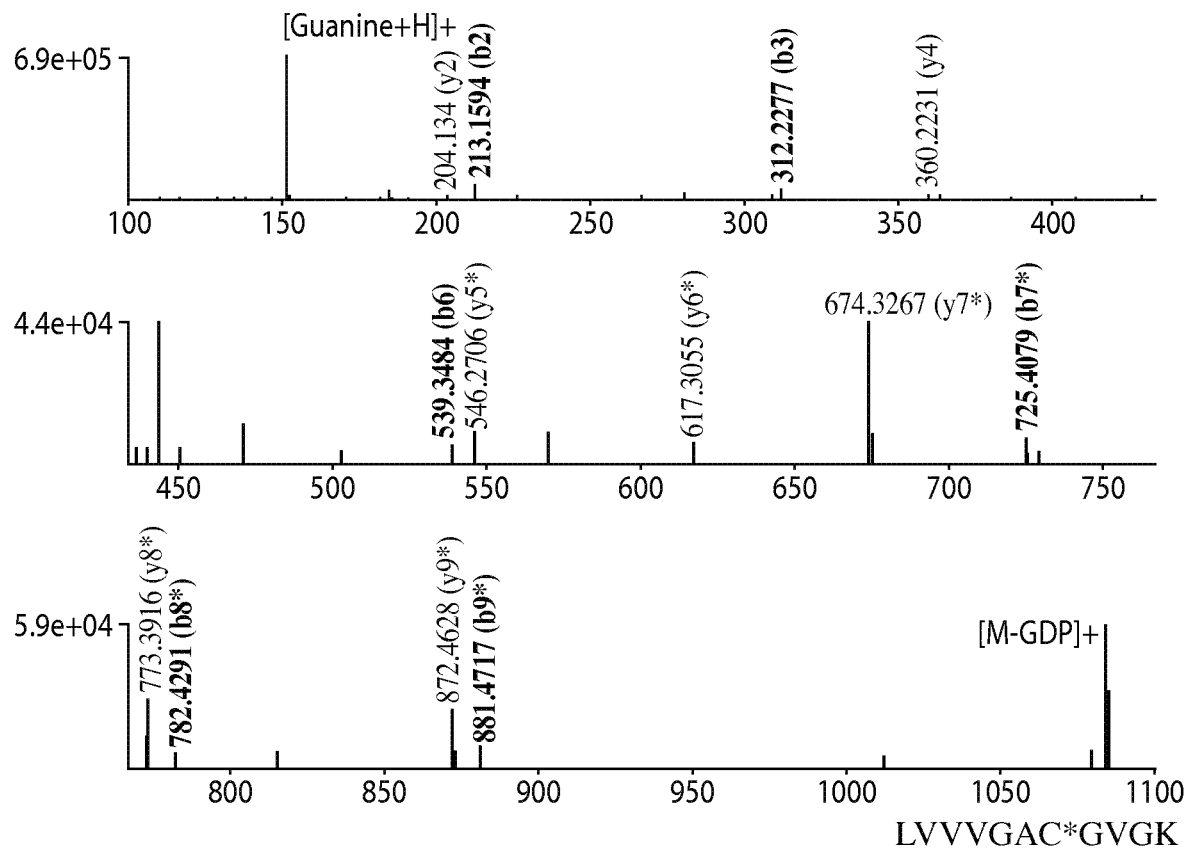
FIG. 3 shows higher energy collisional dissociation (HCD) MS/MS spectrum of Compound 1 modified G12C K-Ras peptide (residues 6-16). Compound 1 modified G12C K-Ras peptide was subject to proteolytic digestion and analyzed by nanoLC/MS. Ions of type b and y are shown in blue and red, respectively, and localize the modification to C12. "*" means loss of GDP.
Figure 4A:
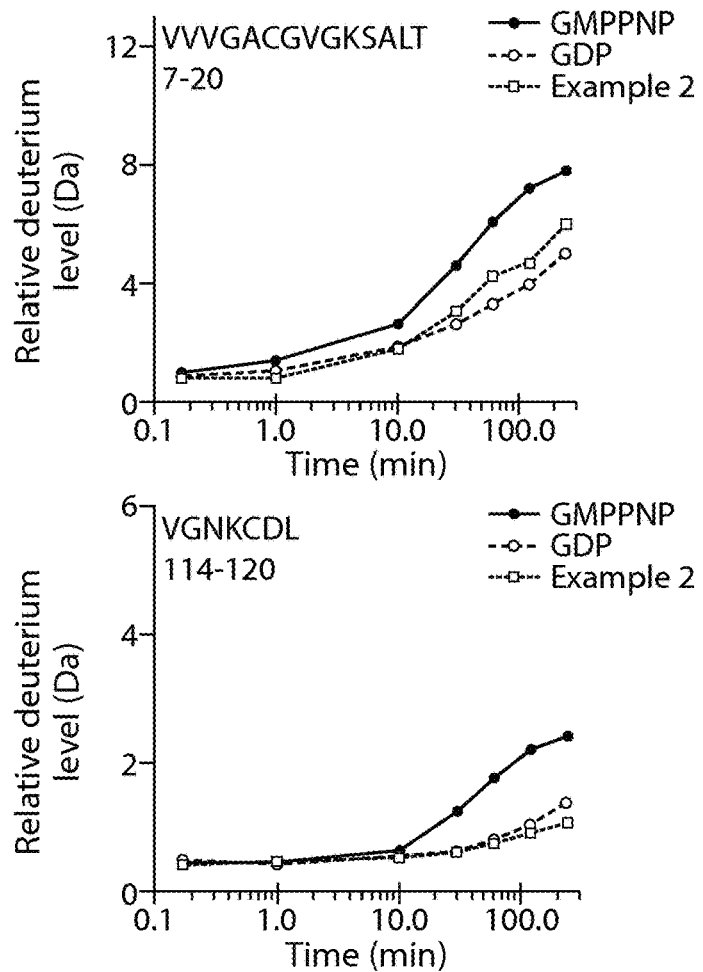
FIG. 4 shows hydrogen deuterium exchange in RasG12C bound to GMPPNP, GDP, and Compound 1. GMPPNP is a non-hydrolyzable GTP mimic. (A) Relative deuterium uptake curves for two key peptides (top: residues 7-20, VVVGACGVGKSALT; bottom: residues 114-120, VGNKCDL) showing differences in deuterium incorporation. Both residues 7-20 and 114-120 show significantly more deuterium incorporation in the active state (GMPPNP-bound) compared to the other states. (B) Location of the two regions (residues 25-38 and 132-138) on PDB file 4Q21.16. Both residues 7-20 and 114-120 with significant differences in deuteration comprise portions of the nucleotide binding pocket with residues 7-20 in close proximity to the phosphate groups and residues 114-120 adjacent to the guanosine moiety.
Figure 4B:
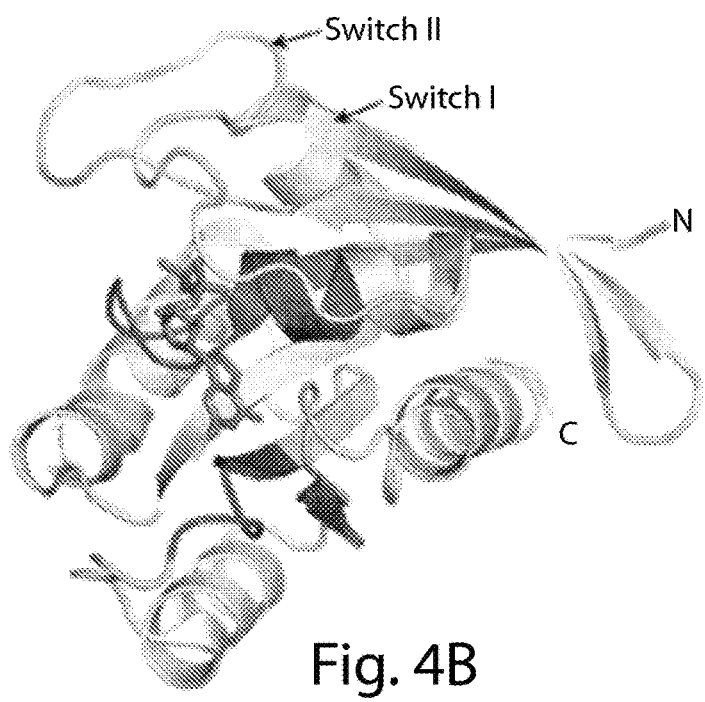
Figure 5:
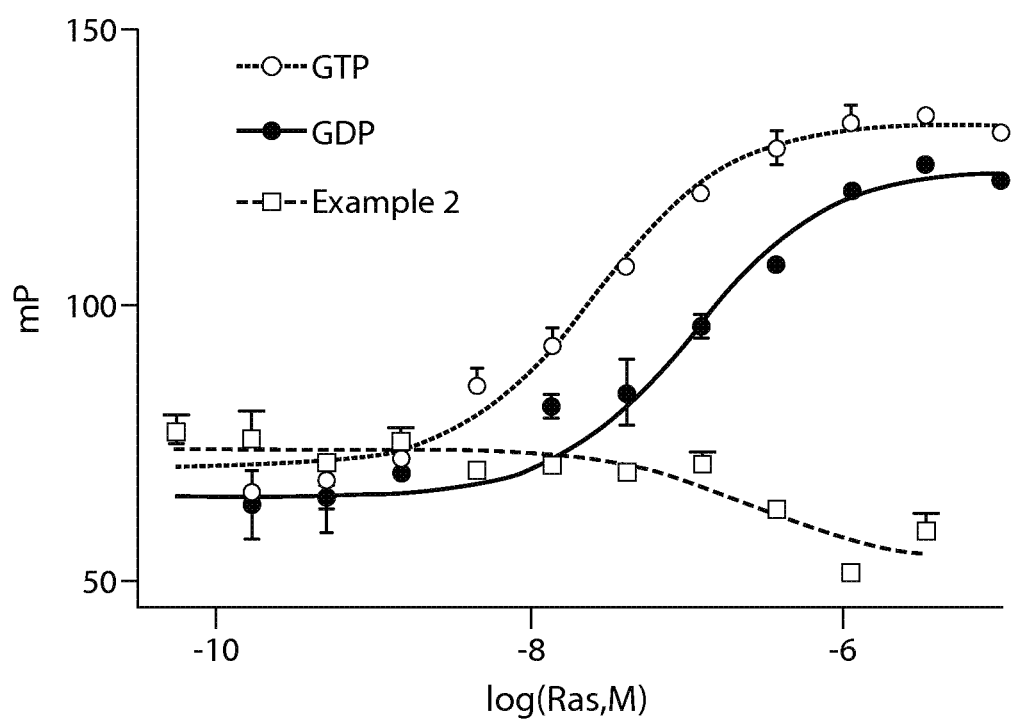
FIG. 5 shows fluorescence polarization assay confirming that Compound 1 addition renders K-Ras G12C biochemically inactive. GTP bound K-Ras G12C has a higher affinity for RBD than the GDP bound form. Compound 1 bound K-Ras G12C does not productively interact with RBD. Examination of a homology model of the RBD:Ras complex (based on PDB ID 1C1Y) revealed that a solvent exposed cysteine sits on the face of RBD opposite the Ras binding side. Oregon green (OG) fluorescent dye was coupled to this cysteine in RBD using maleimide chemistry resulting in covalent addition of one OG, as verified by chromatography and mass spectrometry. When combined with increasing concentrations of recombinant K-Ras a concentration dependent increase in FP was observed suggesting binding of Ras to RBD.
Figure 6:
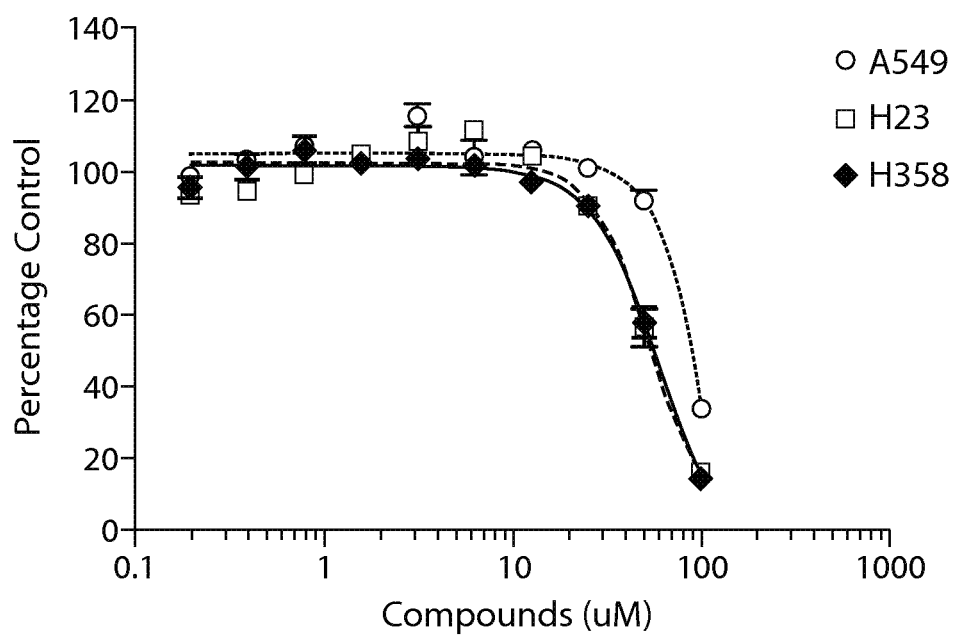
FIG. 6 shows cellular activities of Example 15.
Figure 7:
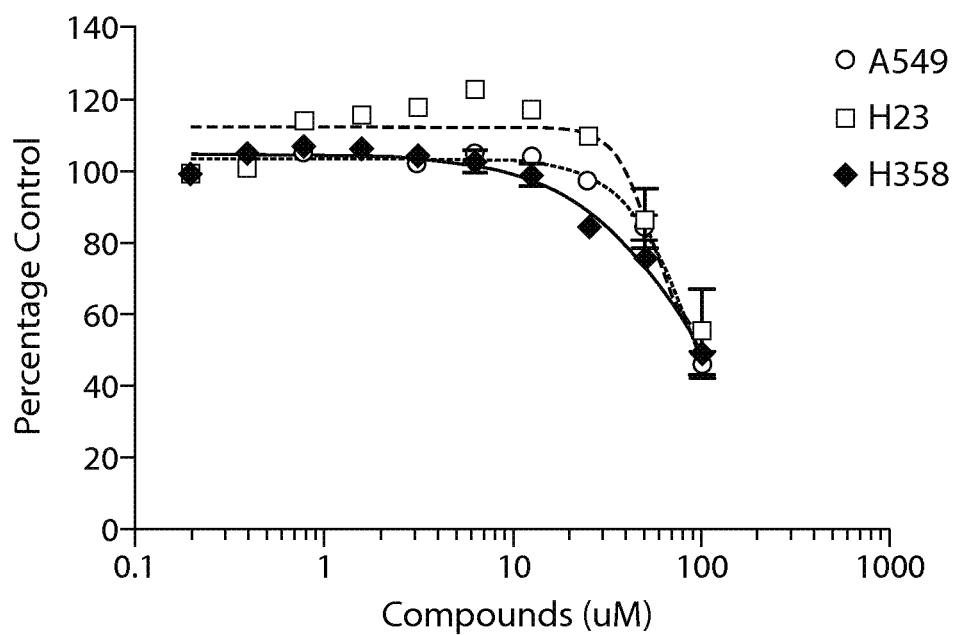
FIG. 7 shows cellular activities of Example 16.
Figure 9:
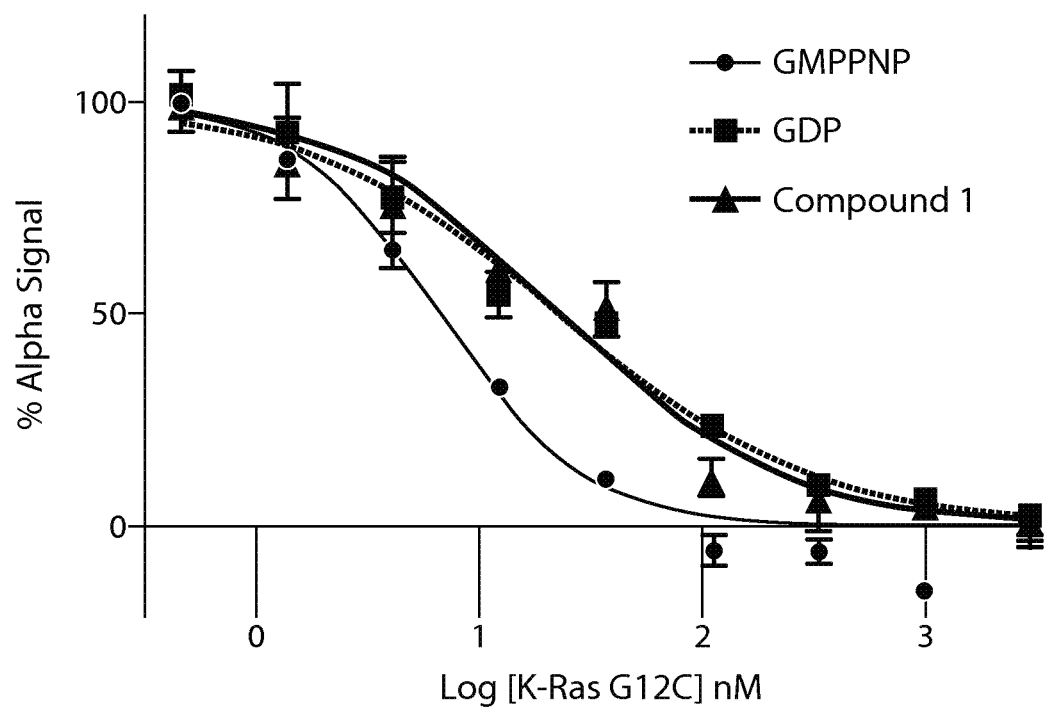
FIG. 9 shows exemplary results of a fluorescence polarization assay of compound 1.
Figure 10:
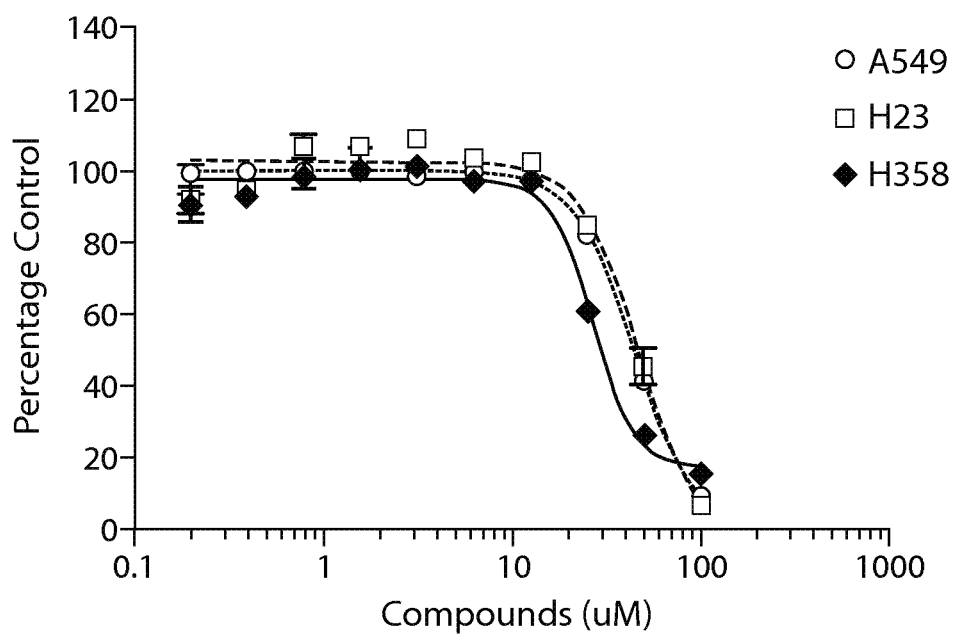
FIG. 10 shows exemplary cellular activities of Example 3. Addition of Example 3 at a 1:10 molar ratio to G12C K-Ras prior to the assay appeared to prevent binding, consistent with the notion that Example 3 stabilizes an inactive conformation of K-Ras that is unable to bind to the RBD protein. This allowed the testing of multiple nucleotides for their ability to induce Ras:Raf binding. The GDP:Ras complex had a lower affinity for RBD ($EC_{50}$ of 108 nM; 95% CI, 55-214 nM), than the GTP:Ras complex ($EC_{50}$ of 26 nM; 95% CI, 19-34 nM).

The present invention provides compounds of Formulae (I)-(II), which inhibit the activity of Ras, for the prevention and/or treatment of a proliferative disease. In certain embodiments, the inventive compounds inhibit the activity of K-Ras. In certain embodiments, the inventive compounds inhibit the activity of the K-Ras mutant G12C. The present invention further provides methods of using the compounds described herein, e.g., as biological probes to study the inhibition of the activity of Ras (e.g., K-Ras (e.g., K-Ras G12C)), and as therapeutics, e.g., in the prevention and/or treatment of diseases associated with the overactivation of Ras and/or aberrant activity of Ras (e.g., K-Ras (e.g., K-Ras G12C)). Also provided are methods of using compounds of Formulae (I)-(II) to treat and/or prevent proliferative diseases. Exemplary proliferative diseases include, but are not limited to, cancers, benign neoplasms, diseases associated with angiogenesis, inflammatory diseases, autoinflammatory diseases, and autoimmune diseases. In certain embodiments, the disease is cancer. Exemplary cancers include, but are not limited to, lung cancer, large bowl cancer, pancreas cancer, biliary tract cancer, or endometrial cancer.

Compounds

As generally described above, provided herein are compounds of Formulae (I)-(II). In certain embodiments, the present disclosure provides compounds of Formula (I):

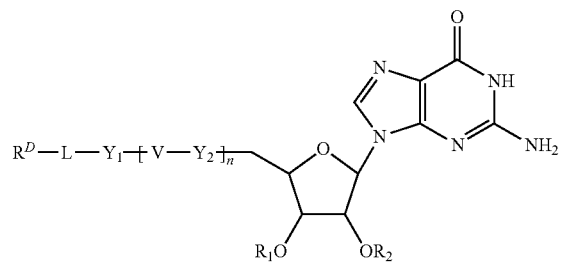

and pharmaceutically acceptable salts, solvates, hydrates, polymorphs, co-crystals, tautomers, stereoisomers, isotopically labeled derivatives, and prodrugs thereof, wherein:

wherein:

each of $R_1$ and $R_2$ is independently hydrogen, optionally substituted alkyl, or an oxygen protecting group, or $R_1$ and $R_2$ are taken together with their intervening atoms to form an optionally substituted heterocyclic ring;

L is a bond, optionally substituted $C_{1-6}$ alkylene, —O—, —S—, or —NR$^N$—;

each instance of $Y_1$ and $Y_2$ is independently —O—, —S—, —NR$^N$—, —C(R$^C$)$_2$—;

each instance of V is independently —C(=O)—, —SO$_2$—, or

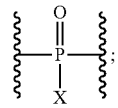

each instance of X is independently hydrogen, —OR$^O$, or —NR$^{N1}$R$^{N2}$;

each instance of R$^N$, R$^{N1}$, and R$^{N2}$ is independently hydrogen, optionally substituted alkyl, or a nitrogen protecting group; or R$^{N1}$ and R$^{N2}$ are taken together with their intervening atoms to form an optionally substituted heterocyclic ring;

each instance of R$^O$ is independently hydrogen, optionally substituted alkyl, optionally substituted aryl, or an oxygen protecting group;

each instance of R$^C$ is independently hydrogen, halogen, or optionally substituted alkyl;

n is 1, 2, or 3; and

R$^D$ is any one of Formulae (i-1)-(i-40):

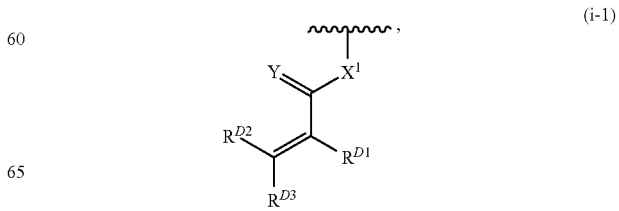

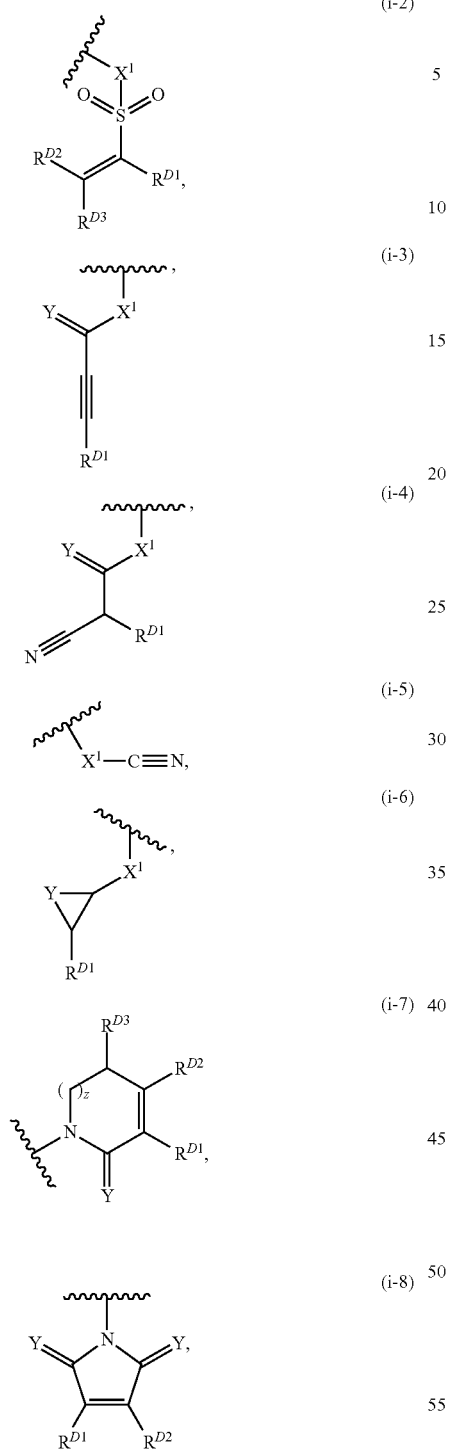
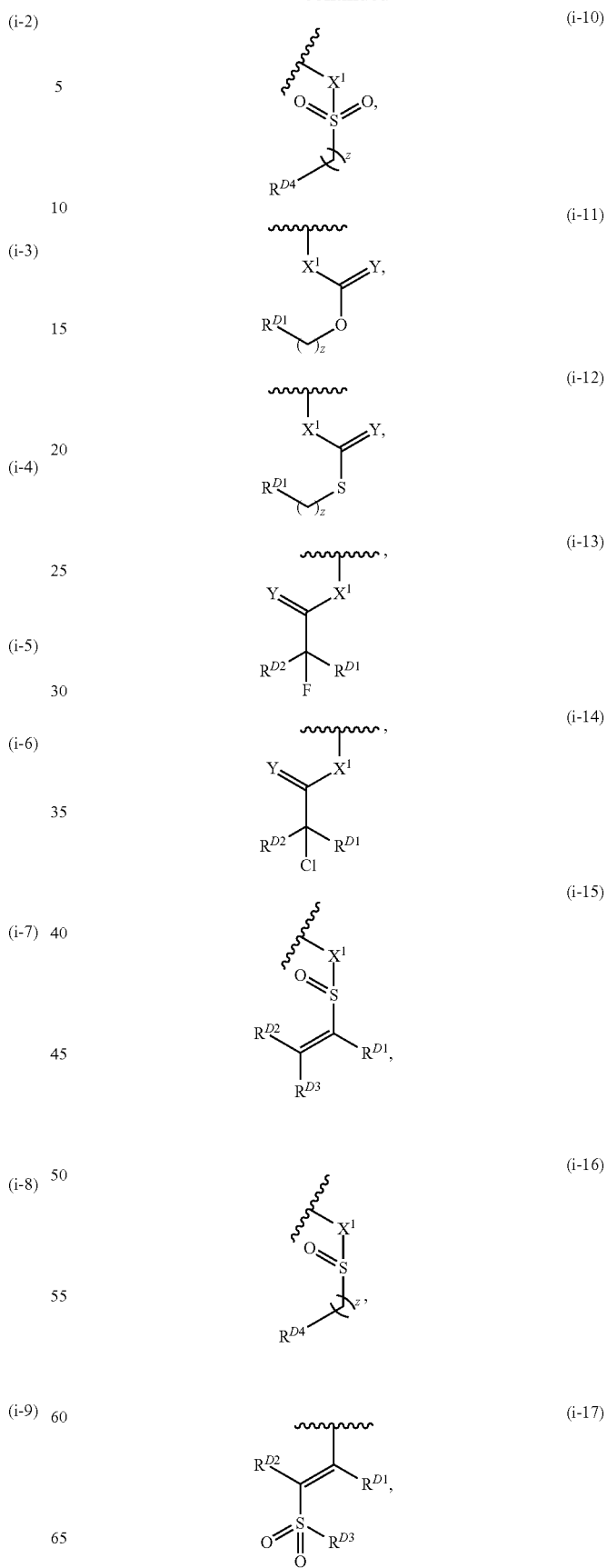

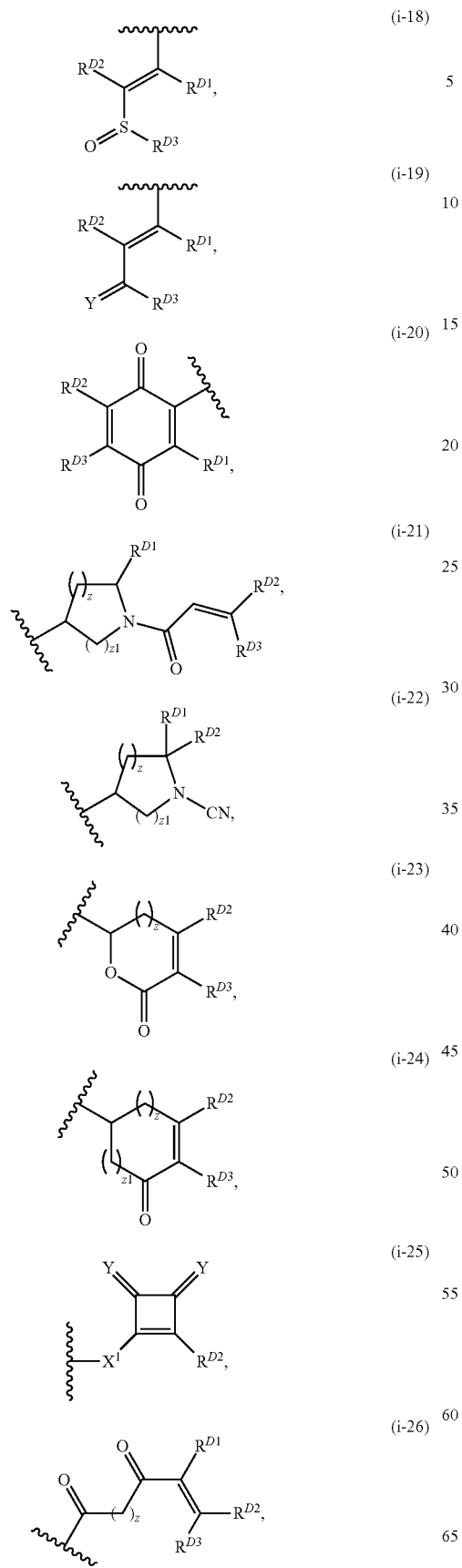
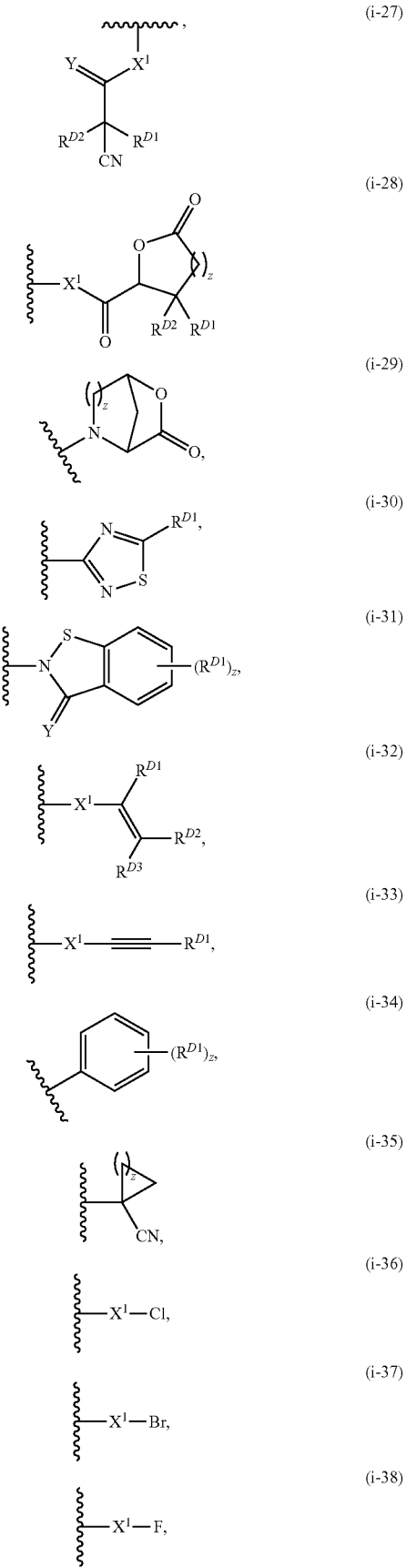

-continued

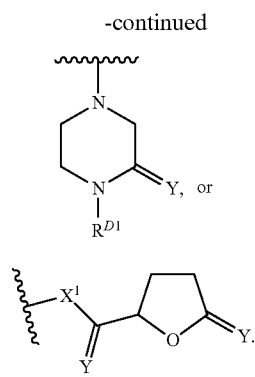

(i-39)

(i-40)

wherein:

each instance of $R^{D1}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, or —C(=NR$^{D1a}$)SR$^{D1a}$, or —C(=NR$^{D1a}$)N(R$^{D1a}$)$_2$, wherein each occurrence of $R^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D1a}$ groups are joined to form an substituted or unsubstituted heterocyclic ring;

each instance of $R^{D2}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, and —C(=NR$^{D2a}$)N(R$^{D2a}$)$_2$, wherein each occurrence of $R^{D2a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two $R^{D2a}$ groups are joined to form an substituted or unsubstituted heterocyclic ring;

each instance of $R^{D3}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)R$^{D3a}$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, or —C(=NR$^{D3a}$)N(R$^{D3a}$)$_2$ wherein each occurrence of $R^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D3a}$ groups are joined to form an substituted or unsubstituted heterocyclic ring;

optionally $R^{D1}$ and $R^{D3}$, or $R^{D2}$ and $R^{D3}$, or $R^{D1}$ and $R^{D2}$ are joined to form an substituted or unsubstituted carbocyclic or substituted or unsubstituted heterocyclic ring;

$R^{D4}$ is a leaving group selected from the group consisting of —Br, —Cl, —I, and —OS(=O)$_w$R$^{D4a}$, wherein w is 1 or 2, and $R^{D4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of $X^1$ is independently a bond, —C(=O)—, —SO$_2$—, NR$^{D5}$, optionally substituted alkylene, or optionally substituted heteroarylene, wherein $R^{D5}$ is hydrogen, $C_{1-6}$ alkyl, or a nitrogen protecting group;

each instance of Y is independently O, S, or NR$^{D6}$, wherein $R^{D6}$ is hydrogen, $C_{1-6}$ alkyl, or a nitrogen protecting group; and each instance of z and $z_1$ is independently 0, 1, 2, 3, 4, 5, or 6, as valency permits.

In certain embodiments, the present disclosure provides compounds of Formula (II):

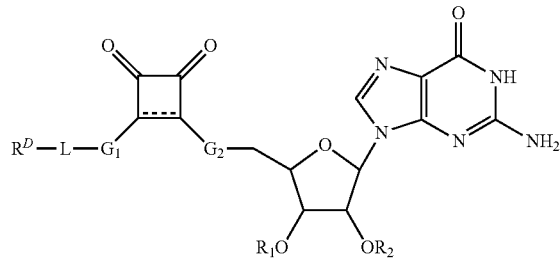

(II)

or a pharmaceutically acceptable salt thereof,
wherein:

---- represents a single bond or a double bond;

each of $R_1$ and $R_2$ is independently hydrogen, optionally substituted alkyl, or an oxygen protecting group, or $R_1$ and $R_2$ are taken together with their intervening atoms to form an optionally substituted heterocyclic ring;

L is a bond, optionally substituted $C_{1-6}$ alkylene, —O—, —S—, or —NR$^N$—;

each instance of $G_1$ and $G_2$ is independently —O—, —S—, —NR$^N$—, —C(R$^C$)$_2$—;

each instance of $R^N$ is independently hydrogen, optionally substituted alkyl, or a nitrogen protecting group; or $R^{N1}$ and $R^{N1}$ are taken together with their intervening atoms to form an optionally substituted heterocyclic ring;

each instance of $R^C$ is independently hydrogen, halogen, or optionally substituted alkyl; and $R^D$ is any one of Formulae (i-1)-(i-40):
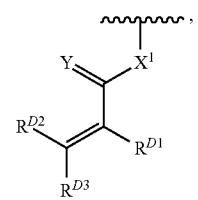
(i-1)
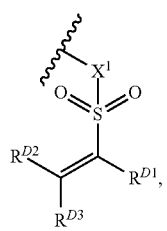
(i-2)
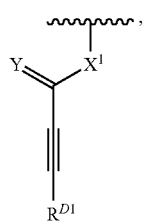
(i-3)
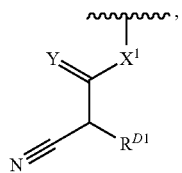
(i-4)
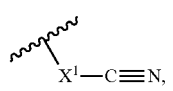
(i-5)
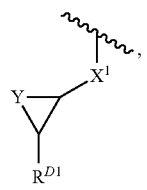
(i-6)
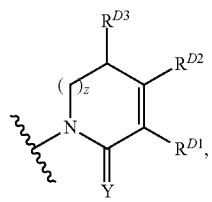
(i-7)
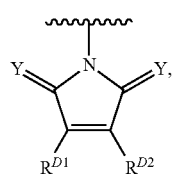
(i-8)
-continued
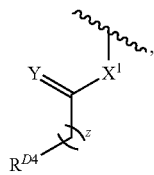
(i-9)
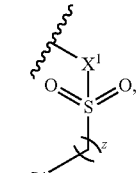
(i-10)
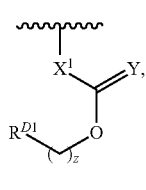
(i-11)
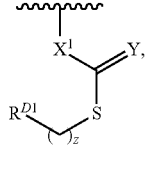
(i-12)
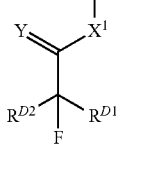
(i-13)
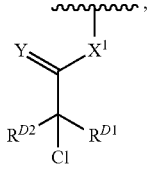
(i-14)
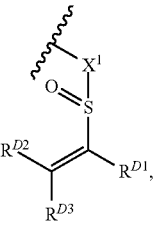
(i-15)
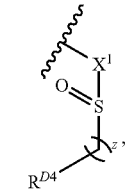
(i-16)

-continued
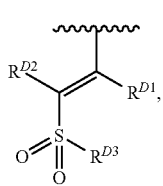 (i-17)
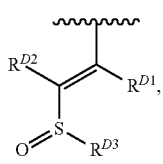 (i-18)
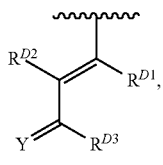 (i-19)
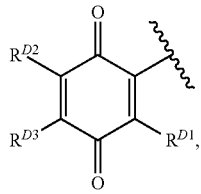 (i-20)
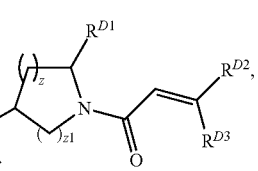 (i-21)
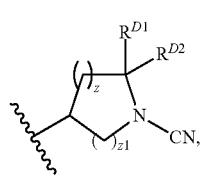 (i-22)
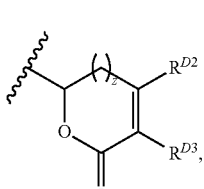 (i-23)
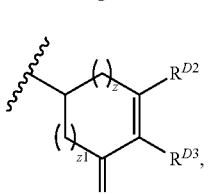 (i-24)
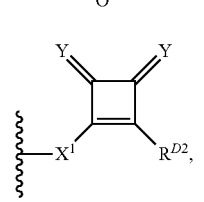 (i-25)
-continued
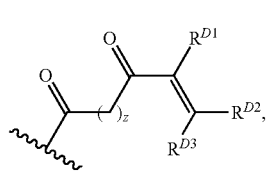 (i-26)
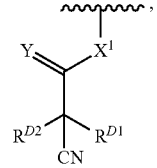 (i-27)
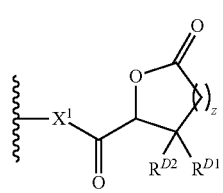 (i-28)
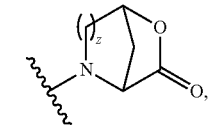 (i-29)
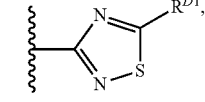 (i-30)
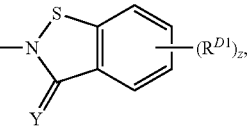 (i-31)
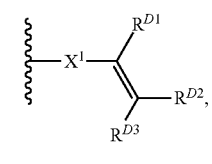 (i-32)
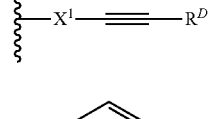 (i-33)
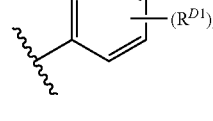 (i-34)
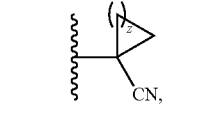 (i-35)
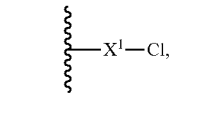 (i-36)

-continued

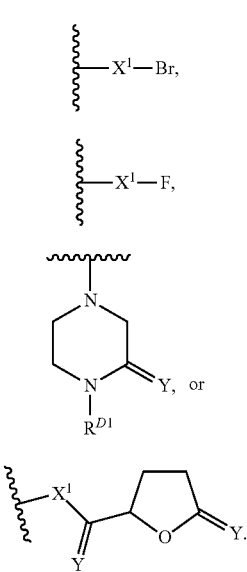

wherein:
each instance of $R^{D1}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)R$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, or —C(=NR$^{D1a}$)N(R$^{D1a}$)$_2$, wherein each occurrence of $R^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D1a}$ groups are joined to form an substituted or unsubstituted heterocyclic ring;

each instance of $R^{D2}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D2a}$, —N(R$^{D2a}$)$^2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, and —C(=NR$^{D2a}$)N(R$^{D2a}$)$_2$, wherein each occurrence of $R^{D2a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two $R^{D2a}$ groups are joined to form an substituted or unsubstituted heterocyclic ring;

each instance of $R^{D3}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)R$^{D3a}$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, or —C(=NR$^{D3a}$)N(R$^{D3a}$)$_2$ wherein each occurrence of $R^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D3a}$ groups are joined to form an substituted or unsubstituted heterocyclic ring;

optionally $R^{D1}$ and $R^{D3}$, or $R^{D2}$ and $R^{D3}$, or $R^{D1}$ and $R^{D2}$ are joined to form an substituted or unsubstituted carbocyclic or substituted or unsubstituted heterocyclic ring;

$R^{D4}$ is a leaving group selected from the group consisting of —Br, —Cl, —I, and —OS(=O)$_w$R$^{D4a}$, wherein w is 1 or 2, and $R^{D4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of $X^1$ is independently a bond, —C(=O)—, —SO$_2$—, NR$^{D5}$, optionally substituted alkylene, or optionally substituted heteroarylene, wherein $R^{D5}$ is hydrogen, C$_{1-6}$ alkyl, or a nitrogen protecting group;

each instance of Y is independently O, S, or NR$^{D6}$, wherein $R^{D6}$ is hydrogen, C$_{1-6}$ alkyl, or a nitrogen protecting group; and each instance of z and $z_1$ is independently 0, 1, 2, 3, 4, 5, or 6, as valency permits.

As generally defined above, n is 1, 2, or 3. In certain embodiments, n is 1. In certain embodiments, n is 2. In certain embodiments, n is 3.

As generally defined above, $Y_1$ is independently —O—, —S—, —NR$^N$—, or —C(R$^C$)$_2$—. In certain embodiments, $Y_2$ is —O—. In certain embodiments, $Y_1$ is —S—. In certain embodiments, $Y_1$ is —NR$^N$—. In certain embodiments, $Y_1$ is —NH—. In certain embodiments, $Y_1$ is —N(CH$_3$)—. In certain embodiments, $Y_1$ is —N(C$_2$H$_5$)—. In certain embodiments, $Y_1$ is —C(R$^C$)$_2$—. In certain embodiments, $Y_1$ is —CH$_2$—. In certain embodiments, $Y_1$ is —CF$_2$—.

As generally defined above, $Y_2$ is independently —O—, —S—, —NR$^N$—, or —C(R$^C$)$_2$—. In certain embodiments, $Y_2$ is —O—. In certain embodiments, $Y_2$ is —S—. In certain embodiments, $Y_2$ is —NR$^N$—. In certain embodiments, $Y_2$ is —NH—. In certain embodiments, $Y_2$ is —N(CH$_3$)—. In certain embodiments, $Y_2$ is —N(C$_2$H$_5$)—. In certain embodiments, $Y_2$ is —C(R$^C$)$_2$—. In certain embodiments, $Y_2$ is —CH$_2$—. In certain embodiments, $Y_2$ is —CF$_2$—.

As generally defined above, each instance of $G_1$ is independently —O—, —S—, —NR$^N$—, —C(R$^C$)$_2$—. In certain embodiments, $G_1$ is —O—. In certain embodiments, $G_1$ is —S—. In certain embodiments, $G_1$ is —NR$^N$—. In certain embodiments, $G_1$ is —NH—. In certain embodiments, $G_1$ is —N(CH$_3$). In certain embodiments, $G_1$ is —N(C$_2$H$_5$)—. In certain embodiments, $G_1$ is —CH$_2$—. In certain embodiments, $G_1$ is —CF$_2$—.

As generally defined above, each instance of $G_2$ is independently —O—, —S—, —NR$^N$—, —C(R$^C$)$_2$—. In certain embodiments, $G_2$ is —O—. In certain embodiments, $G_2$ is —S—. In certain embodiments, $G_2$ is —NR$^N$—. In certain embodiments, $G_2$ is —NH—. In certain embodiments, $G_2$ is —N(CH$_3$)—. In certain embodiments, G$_2$ is —N(C$_2$H$_5$)—. In certain embodiments, G$_2$ is —CH$_2$—. In certain embodiments, G$_2$ is —CF$_2$—.

As used herein, R$^N$ is independently hydrogen, optionally substituted alkyl, or a nitrogen protecting group. In certain embodiments, R$^N$ is hydrogen. In certain embodiments, R$^N$ is optionally substituted C$_{1-6}$ alkyl. In certain embodiments, R$^N$ is substituted C$_{1-6}$ alkyl. In certain embodiments, R$^N$ is unsubstituted C$_{1-6}$ alkyl. In certain embodiments, R$^N$ is methyl, ethyl, propyl, butyl, or pentyl. In certain embodiments, R$^N$ is isopropyl, isobutyl, or isoamyl. In certain embodiments, R$^N$ is isobutyl. In certain embodiments, R$^N$ is tert-butyl. In certain embodiments, R$^N$ is a nitrogen protecting group as defined herein.

As used herein, R$^C$ is independently hydrogen, halogen, or optionally substituted alkyl. In certain embodiments, R$^C$ is hydrogen. In certain embodiments, R$^C$ is halogen. In certain embodiments, R$^C$ is F. In certain embodiments, R$^C$ is Cl. In certain embodiments, R$^C$ is Br. In certain embodiments, R$^C$ is I. In certain embodiments, R$^C$ is optionally substituted C$_{1-6}$ alkyl. In certain embodiments, R$^C$ is substituted C$_{1-6}$ alkyl. In certain embodiments, R$^C$ is unsubstituted C$_{1-6}$ alkyl. In certain embodiments, R$^C$ is methyl, ethyl, propyl, butyl, or pentyl. In certain embodiments, R$^C$ is isopropyl, isobutyl, or isoamyl. In certain embodiments, R$^C$ is isobutyl. In certain embodiments, R$^C$ is tert-butyl.

As generally defined above, V is —C(=O), —SO$_2$—, or

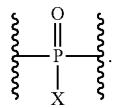

In certain embodiments, V is —C(=O)—. In certain embodiments, V is —SO$_2$—. In certain embodiments, V is

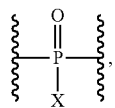

wherein X is as defined herein. In certain embodiments, n is 1 and V is

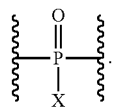

In certain embodiments, n is 1 and V is —SO$_2$—. In certain embodiments, n is 1 and V is —C(=O)—. In certain embodiments, n is 2 and V is

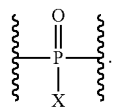

In certain embodiments, n is 2 and V is —SO$_2$—. In certain embodiments, n is 2 and V is —C(=O)—. In certain embodiments, n is 3 and V is —SO$_2$—. In certain embodiments, n is 3 and V is —C(=O)—. In certain embodiments, n is 3 and V is

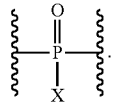

As generally defined above, X is independently hydrogen, —OR$^O$, or —NR$^{N1}$R$^{N2}$, wherein each instance of R$^{N1}$, and R$^{N2}$ is independently hydrogen, optionally substituted alkyl, or a nitrogen protecting group; or R$^{N1}$ and R$^{N2}$ are taken together with their intervening atoms to form an optionally substituted heterocyclic ring; and each instance of R$^O$ is independently hydrogen, optionally substituted alkyl, or an oxygen protecting group. In certain embodiments, X is

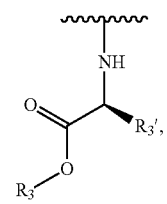

wherein R$_3$ and R$_3$' are as defined herein. In certain embodiments, X is

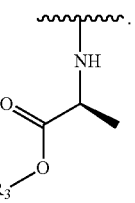

In certain embodiments, X is —OR$^O$. In certain embodiments, R$^O$ is hydrogen and X is —OH. In certain embodiments, R$^O$ is optionally substituted C$_{1-20}$ alkyl. In certain embodiments, R$^O$ is substituted C$_{1-20}$ alkyl. In certain embodiments, R$^O$ is unsubstituted C$_{1-20}$ alkyl. In certain embodiments, R$^O$ is methyl, ethyl, propyl, butyl, or pentyl. In certain embodiments, R$^O$ is isopropyl, isobutyl, or isoamyl. In certain embodiments, R$^O$ is isobutyl. In certain embodiments, R$^O$ is tert-butyl. In certain embodiments, R$^O$ is of the formula

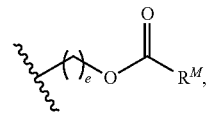

wherein e is 1, 2, 3, 4, 5, 6, 7, 8, 9, or 10; and R$^M$ is optionally substituted alkyl or optionally substituted aryl. In certain embodiments, e is 1. In certain embodiments, e is 2. In certain embodiments, e is 3. In certain embodiments, e is 4. In certain embodiments, e is 5. In certain embodiments, e is 6. In certain embodiments, e is 7. In certain embodiments, e is 8. In certain embodiments, e is 9. In certain embodiments, e is 10. In certain embodiments, $R^M$ is optionally substituted $C_{1-6}$ alkyl. In certain embodiments, $R^M$ is substituted $C_{1-6}$ alkyl. In certain embodiments, $R^M$ is unsubstituted $C_{1-6}$ alkyl. In certain embodiments, $R^M$ is methyl, ethyl, propyl, butyl, or pentyl. In certain embodiments, $R^M$ is isopropyl, isobutyl, or isoamyl. In certain embodiments, $R^M$ is isobutyl. In certain embodiments, $R^M$ is tert-butyl. In certain embodiments, $R^O$ is optionally substituted aryl. In certain embodiments, $R^O$ is phenyl. In certain embodiments, $R^O$ is substituted aryl. In certain embodiments, $R^O$ is of the formula

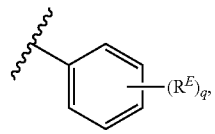

wherein q is 0, 1, 2, 3, 4, or 5; and each instance of $R^E$ is independently selected from the group consisting of halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —C(=O)N(R$^B$)N(R$^B$)$_2$, —OC(=O)R$^A$, —OC(=O)N(R$^B$)$_2$, —NR$^B$C(=O)R$^A$, —NR$^B$C(=O)N(R$^B$)$_2$, —NR$^B$C(=O)N(R$^B$)N(R$^B$)$_2$, —NR$^B$C(=O)OR$^A$, —SC(=O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —OS(=O)$_2$R$^A$, —SO$_2$R$^A$, —NR$^B$SO$_2$R$^A$, and —SO$_2$N(R$^B$)$_2$; wherein each R$^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl; and each R$^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^B$ groups are taken together with their intervening atoms to form an optionally substituted heterocyclic ring.

As generally defined herein, q is 0, 1, 2, 3, 4, or 5. In certain embodiments, q is 0. In certain embodiments, q is 1 and $R^O$ is of the formula

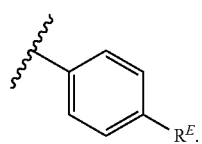

In certain embodiments, q is 1 and $R^O$ is of the formula

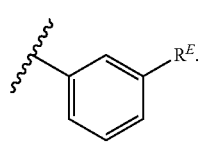

In certain embodiments, q is 1 and $R^O$ is of the formula

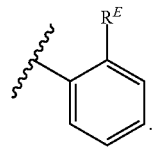

In certain embodiments, q is 2 and $R^O$ is of the formula

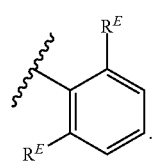

In certain embodiments, q is 2 and $R^O$ is of the formula

In certain embodiments, q is 2 and $R^O$ is of the formula

In certain embodiments, In certain embodiments, q is 2 and $R^O$ is of the formula In certain embodiments, In certain embodiments, q is 2 and $R^O$ is of the formula

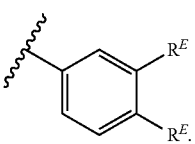

In certain embodiments, In certain embodiments, q is 2 and $R^O$ is of the formula

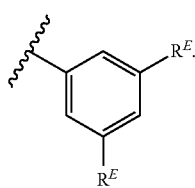

In certain embodiments, q is 3 and $R^O$ is of the formula

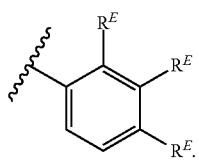

In certain embodiments, q is 3 and $R^O$ is of the formula

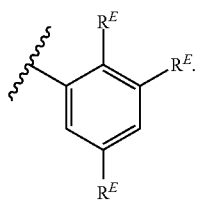

In certain embodiments, q is 3 and $R^O$ is of the formula

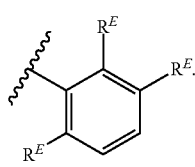

In certain embodiments, q is 3 and $R^O$ is of the formula

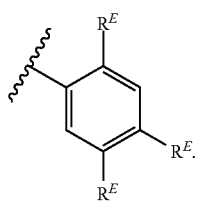

In certain embodiments, q is 3 and $R^O$ is of the formula

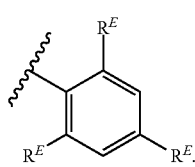

In certain embodiments, q is 4 and $R^O$ is of the formula

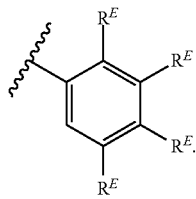

In certain embodiments, q is 4 and $R^O$ is of the formula

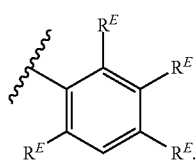

In certain embodiments, q is 4 and $R^O$ is of the formula

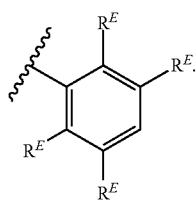

In certain embodiments, q is 5 and $R^O$ is of the formula

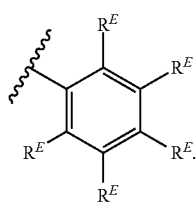

In certain embodiments, $R^E$ is optionally substituted $C_{1-6}$ alkyl, optionally substituted $C_{2-6}$ alkenyl, optionally substituted $C_{2-6}$ alkynyl, or optionally substituted $C_{3-6}$ carbocyclyl. In certain embodiments, $R^E$ is optionally substituted $C_{1-6}$ alkyl. In certain embodiments, $R^E$ is substituted $C_{1-6}$ alkyl. In certain embodiments, $R^E$ is methyl, ethyl, propyl, butyl, or pentyl. In certain embodiments, $R^E$ is isopropyl, isobutyl, or isoamyl. In certain embodiments, $R^E$ is isobutyl. In certain embodiments, $R^E$ is tert-butyl. In certain embodiments, $R^E$ is —N($R^B$)$_2$. In certain embodiments, $R^E$ is —NH$R^B$. In certain embodiments, $R^E$ is —NH$R^B$, wherein $R^B$ is hydrogen or optionally substituted $C_{1-6}$ alkyl. In certain embodiments, $R^E$ is —NH$_2$. In certain embodiments, $R^E$ is —O$R^A$. In certain embodiments, $R^E$ is —OH. In certain embodiments, $R^E$ is —O$R^A$, wherein $R^A$ is optionally substituted alkyl, optionally substituted alkenyl, optionally substituted alkynyl, or optionally substituted carbocyclyl. In certain embodiments, $R^E$ is —O-isobutylenyl. In certain embodiments, $R^E$ is —O$R^A$, wherein $R^A$ is optionally substituted $C_{1-6}$ alkyl. In certain embodiments, $R^E$ is —O$R^A$, wherein $R^A$ is unsubstituted $C_{1-6}$ alkyl. In certain embodiments, $R^E$ is —O-methyl, —O-ethyl, —O-propyl, —O-isopropyl, —O-isobutyl, or —O-isoamyl.

In certain embodiments, X is —NR$^{N1}$R$^{N2}$. In certain embodiments, R$^{N1}$ is hydrogen. In certain embodiments, R$^{N1}$ is of the formula:

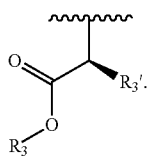

In certain embodiments, R$^{N1}$ is of the formula:

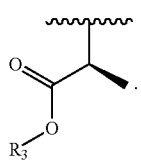

In certain embodiments, R$^{N2}$ is hydrogen. In certain embodiments, R$^{N2}$ is of the formula:

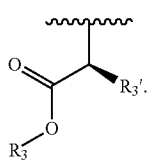

In certain embodiments, R$^{N2}$ is of the formula:

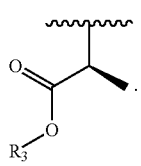

As used herein, each instance of R$_3$' is independently hydrogen, optionally substituted alkyl, optionally substituted carbocyclyl, optionally substituted heteroalkyl, or optionally substituted aralkyl. In certain embodiments, R$_3$' is hydrogen. In certain embodiments, R$_3$' is substituted C$_{1-20}$ alkyl. In certain embodiments, R$_3$' is unsubstituted C$_{1-20}$ alkyl. In certain embodiments, R$_3$' is methyl, ethyl, propyl, butyl, or pentyl. In certain embodiments, R$_3$' is isopropyl, isobutyl, or isoamyl. In certain embodiments, R$_3$' is isobutyl. In certain embodiments, R$_3$' is tert-butyl. In certain embodiments, R$_3$' is optionally substituted —CH$_2$-phenyl. In certain embodiments, R$_3$' is unsubstituted —CH$_2$-phenyl. In certain embodiments, R$_3$' is optionally substituted —(CH$_2$)$_2$-phenyl. In certain embodiments, R$_3$' is optionally substituted —(CH$_2$)$_3$-phenyl. In certain embodiments, R$_3$' is optionally substituted —(CH$_2$)$_4$-phenyl. In certain embodiments, R$_3$' is optionally substituted —(CH$_2$)$_5$-phenyl. In certain embodiments, R$_3$' is optionally substituted —(CH$_2$)$_6$-phenyl. In certain embodiments, R$_3$' is optionally substituted heteroalkyl. In certain embodiments, R$_3$' is —(CH$_2$)$_s$—W—(CH$_2$)$_{s1}$—, wherein W is O, S or NH; each instance of s and s1 is independently 0, 1, 2, 3, 4, 5, or 6. In certain embodiments, R$_3$' is —(CH$_2$)$_s$—O—(CH$_2$)$_{s1}$—. In certain embodiments, R$_3$ is —(CH$_2$)$_s$—S—(CH$_2$)$_{s1}$—. In certain embodiments, R$_3$ is —(CH$_2$)$_s$—NH—(CH$_2$)$_{s1}$—. In certain embodiments, s is 0. In certain embodiments, s is 1. In certain embodiments, s is 2. In certain embodiments, s is 3. In certain embodiments, s is 4. In certain embodiments, s is 5. In certain embodiments, s is 6. In certain embodiments, s1 is 0. In certain embodiments, s1 is 1. In certain embodiments, s1 is 2. In certain embodiments, s1 is 3. In certain embodiments, s1 is 4. In certain embodiments, s1 is 5. In certain embodiments, s1 is 6.

As generally defined herein, R$_3$ is optionally substituted alkyl, optionally substituted heteroalkyl, optionally substituted aralkyl, or optionally substituted carbocyclyl. In certain embodiments, R$_3$ is optionally substituted C$_{1-20}$ alkyl. In certain embodiments, R$_3$ is substituted methyl. In certain embodiments, R$_3$ is unsubstituted methyl. In certain embodiments, R$_3$ is substituted ethyl. In certain embodiments, R$_3$ is unsubstituted ethyl. In certain embodiments, R$_3$ is substituted n-propyl. In certain embodiments, R$_3$ is unsubstituted n-propyl. In certain embodiments, R$_3$ is substituted isopropyl. In certain embodiments, R$_3$ is unsubstituted isopropyl. In certain embodiments, R$_3$ is —(CH$_2$)$_{12}$CH$_3$. In certain embodiments, R$_3$ is —(CH$_2$)$_{11}$CH$_3$. In certain embodiments, R$_3$ is —(CH$_2$)$_{10}$CH$_3$. In certain embodiments, R$_3$ is —(CH$_2$)$_9$CH$_3$. In certain embodiments, R$_3$ is —(CH$_2$)$_8$CH$_3$. In certain embodiments, R$_3$ is —(CH$_2$)$_7$CH$_3$. In certain embodiments, R$_3$ is —(CH$_2$)$_6$CH$_3$. In certain embodiments, R$_3$ is —(CH$_2$)$_5$CH$_3$. In certain embodiments, R$_3$ is —(CH$_2$)$_4$CH$_3$. In certain embodiments, R$_3$ is —(CH$_2$)$_3$CH$_3$. In certain embodiments, R$_3$ is of the formula:

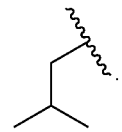

In certain embodiments, R$_3$ is of the formula

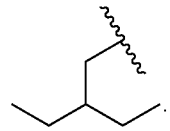 [SMILES: *CC(CC)CC]

In certain embodiments, R$_3$ is of the formula:

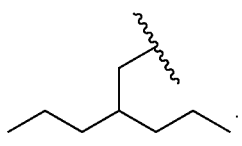 [SMILES: *CC(CCC)CCC]

In certain embodiments, R$_3$ is of the formula:

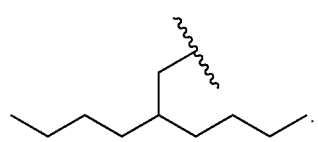 [SMILES: *CC(CCCC)CCCC]

In certain embodiments, $R_3$ is of the formula:

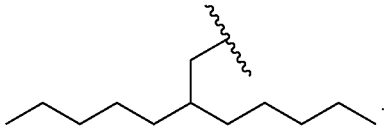 [SMILES: *CC(CCCCC)CCCCC]

In certain embodiments, $R_3$ is optionally substituted heteroalkyl. In certain embodiments, $R_3$ is optionally substituted —$CH_2$-phenyl. In certain embodiments, $R_3$ is unsubstituted —$CH_2$-phenyl. In certain embodiments, $R_3$ is optionally substituted —$(CH_2)_2$-phenyl. In certain embodiments, $R_3$ is optionally substituted —$(CH_2)_3$-phenyl. In certain embodiments, $R_3$ is optionally substituted —$(CH_2)_4$-phenyl. In certain embodiments, $R_3$ is optionally substituted —$(CH_2)_5$-phenyl. In certain embodiments, $R_3$ is optionally substituted —$(CH_2)_6$-phenyl. In certain embodiments, $R_3$ is optionally substituted heteroalkyl. In certain embodiments, $R_3$ is —$(CH_2)_s$—W—$(CH_2)_{s1}$—, wherein W is O, S or NH; each of s and s1 is independently 0, 1, 2, 3, 4, 5, or 6. In certain embodiments, $R_3$ is —$(CH_2)_s$—O—$(CH_2)_{s1}$—. In certain embodiments, $R_3$ is —$(CH_2)_s$—S—$(CH_2)_{s1}$—. In certain embodiments, $R_3$ is —$(CH_2)_s$—NH—$(CH_2)_{s1}$—. In certain embodiments, $R_3$ is optionally substituted carbocyclyl. In certain embodiments, $R_3$ is optionally substituted $C_{1-10}$ carbocyclyl. In certain embodiments, $R_3$ is optionally substituted cyclopropyl, cyclobutyl, cyclopentyl, cyclohexyl, cycloheptyl, or cyclooctyl.

As generally defined, L is a bond, optionally substituted $C_{1-6}$ alkylene, —O— or —$NR^N$—. In certain embodiments, L is a bond. In certain embodiments, L is —O—. In certain embodiments, L is —$NR^N$—. In certain embodiments, L is —NH—. In certain embodiments, L is $C_{1-6}$ alkylene. In certain embodiments, L is —$(CH_2)_m$—, wherein m is 1, 2, 3, 4, 5, 6, 7, or 8. In certain embodiments, m is 1. In certain embodiments, m is 2. In certain embodiments, m is 3. In certain embodiments, m is 4. In certain embodiments, m is 5. In certain embodiments, m is 6. In certain embodiments, m is 7. In certain embodiments, m is 8.

As defined herein, $R_1$ is independently hydrogen, optionally substituted alkyl, or an oxygen protecting group. In certain embodiments, $R_1$ is hydrogen. In certain embodiments, $R_1$ is optionally substituted alkyl. In certain embodiments, $R_1$ is optionally substituted $C_{1-6}$ alkyl. In certain embodiments, $R_1$ is unsubstituted methyl. In certain embodiments, $R_1$ is substituted methyl. In certain embodiments, $R_1$ is unsubstituted ethyl. In certain embodiments, $R_1$ is substituted ethyl. In certain embodiments, $R_1$ is an oxygen protecting group as defined herein. In certain embodiments, $R_1$ is acyl. In certain embodiments, $R_1$ is acetyl.

As defined herein, $R_2$ is independently hydrogen, optionally substituted alkyl, or an oxygen protecting group. In certain embodiments, $R_2$ is hydrogen. In certain embodiments, $R_2$ is optionally substituted alkyl. In certain embodiments, $R_2$ is optionally substituted $C_{1-6}$ alkyl. In certain embodiments, $R_2$ is unsubstituted methyl. In certain embodiments, $R_2$ is substituted methyl. In certain embodiments, $R_2$ is unsubstituted ethyl. In certain embodiments, $R_2$ is substituted ethyl. In certain embodiments, $R_2$ is an oxygen protecting group as define herein. In certain embodiments, $R_2$ is acyl. In certain embodiments, $R_2$ is acetyl.

In certain embodiments, $R_1$ and $R_2$ are taken together with their intervening atoms to form a heterocyclic ring of Formula (i):

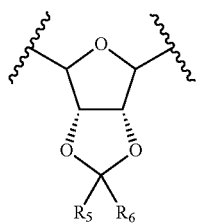

(i)

wherein
each of $R_5$ and $R_6$ is independently hydrogen or optionally substituted $C_{1-6}$ alkyl. In certain embodiments, $R_5$ is unsubstituted methyl. In certain embodiments, $R_5$ is substituted methyl. In certain embodiments, $R_5$ is unsubstituted ethyl. In certain embodiments, $R_5$ is substituted ethyl. In certain embodiments, $R_6$ is unsubstituted methyl. In certain embodiments, $R_6$ is substituted methyl. In certain embodiments, $R_6$ is unsubstituted ethyl. In certain embodiments, $R_6$ is substituted ethyl. In certain embodiments, $R_5$ and $R_6$ are unsubstituted methyl. In certain embodiments, $R_5$ and $R_6$ are substituted methyl. In certain embodiments, $R_5$ and $R_6$ are unsubstituted ethyl. In certain embodiments, $R_5$ and $R_6$ are substituted ethyl.

As generally defined, $R^D$ is any one of Formulae (i-1)-(i-40):

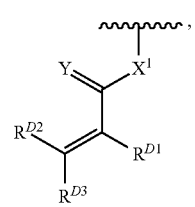

(i-1)

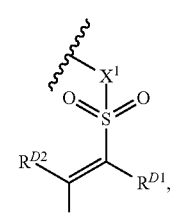

(i-2)

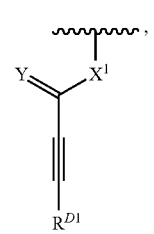

(i-3)

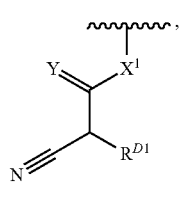

(i-4)

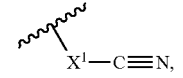

(i-5)

-continued
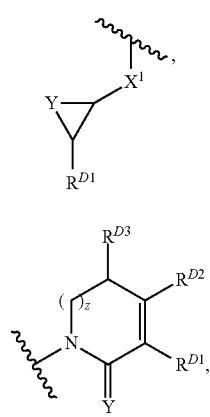 (i-6)
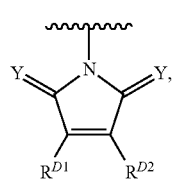 (i-7)
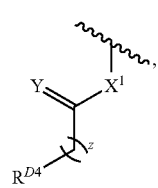 (i-8)
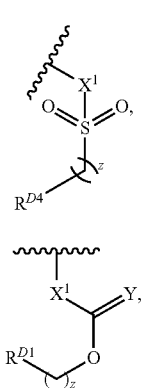 (i-9)
(i-10)
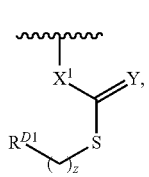 (i-11)
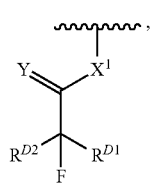 (i-12)
(i-13)
-continued
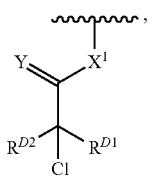 (i-14)
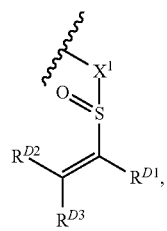 (i-15)
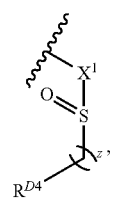 (i-16)
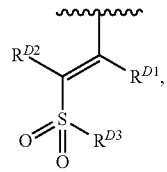 (i-17)
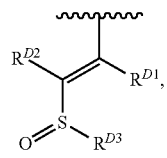 (i-18)
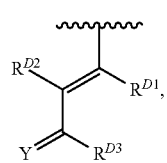 (i-19)
(i-20)
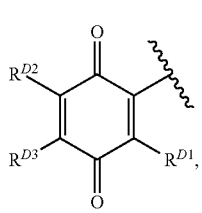 (i-21)

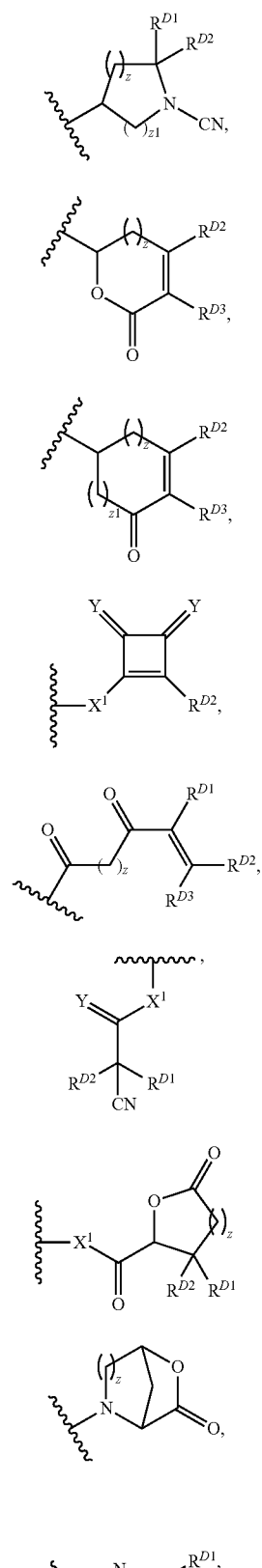

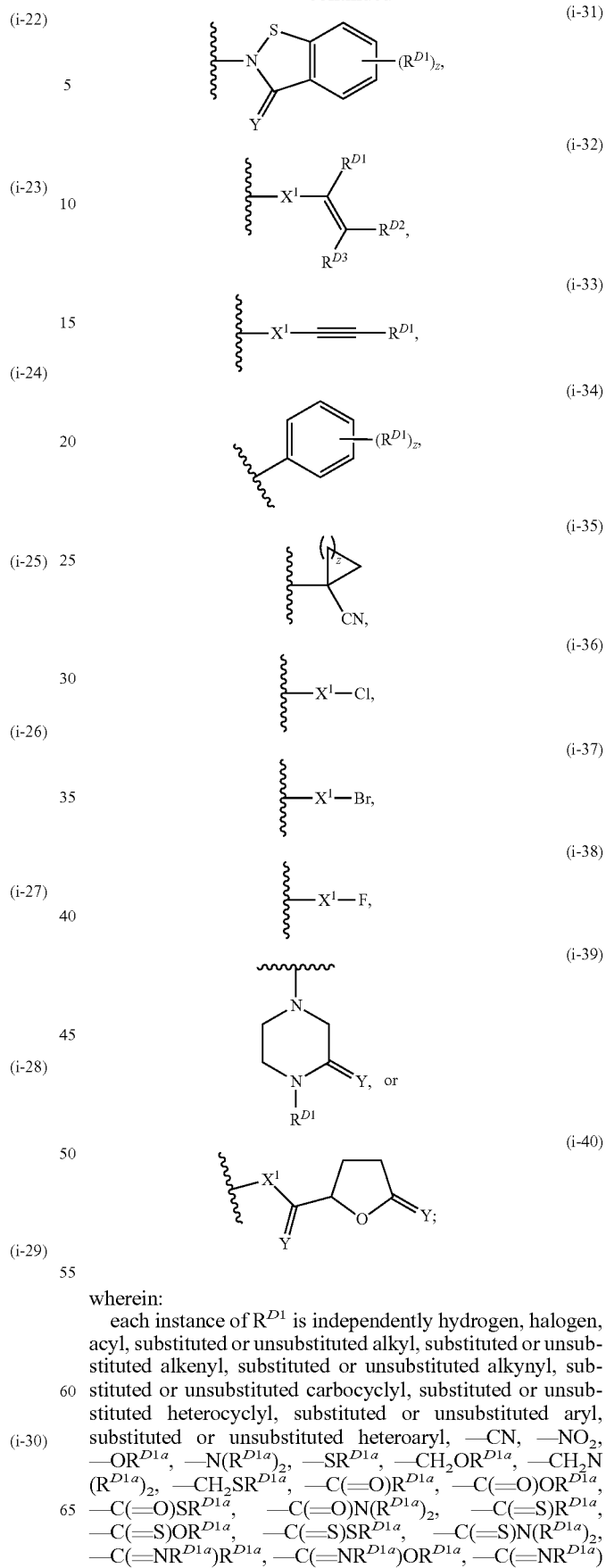

wherein:
each instance of $R^{D1}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)

$SR^{D1a}$, or $—C(=NR^{D1a})N(R^{D1a})_2$, wherein each occurrence of $R^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D1a}$ groups are joined to form an substituted or unsubstituted heterocyclic ring;

each instance of $R^{D2}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $—CN$, $—NO_2$, $—OR^{D2a}$, $—N(R^{D2a})_2$, $—SR^{D2a}$, $—CH_2OR^{D2a}$, $—CH_2N(R^{D2a})_2$, $—CH_2SR^{D2a}$, $—C(=O)R^{D2a}$, $—C(=O)OR^{D2a}$, $—C(=O)SR^{D2a}$, $—C(=O)N(R^{D2a})_2$, $—C(=S)R^{D2a}$, $—C(=S)OR^{D2a}$, $—C(=S)SR^{D2a}$, $—C(=S)N(R^{D2a})_2$, $—C(=NR^{D2a})R^{D2a}$, $—C(=NR^{D2a})OR^{D2a}$, $—C(=NR^{D2a})SR^{D2a}$, and $—C(=NR^{D2a})N(R^{D2a})_2$, wherein each occurrence of $R^{D2a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two $R^{D2a}$ groups are joined to form an substituted or unsubstituted heterocyclic ring;

each instance of $R^{D3}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $—OR^{D3a}$, $—N(R^{D3a})_2$, $—SR^{D3a}$, $—CH_2OR^{D3a}$, $—CH_2N(R^{D3a})_2$, $—CH_2SR^{D3a}$, $—C(=O)R^{D3a}$, $—C(=O)OR^{D3a}$, $—C(=O)SR^{D3a}$, $—C(=O)N(R^{D3a})_2$, $—C(=S)R^{D3a}$, $—C(=S)OR^{D3a}$, $—C(=S)SR^{D3a}$, $—C(=S)N(R^{D3a})_2$, $—C(=NR^{D3a})R^{D3a}$, $—C(=NR^{D3a})OR^{D3a}$, $—C(=NR^{D3a})SR^{D3a}$, or $—C(=NR^{D3a})N(R^{D3a})_2$ wherein each occurrence of $R^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D3a}$ groups are joined to form an substituted or unsubstituted heterocyclic ring;

optionally $R^{D1}$ and $R^{D3}$, or $R^{D2}$ and $R^{D3}$, or $R^{D1}$ and $R^{D2}$ are joined to form an substituted or unsubstituted carbocyclic or substituted or unsubstituted heterocyclic ring;

$R^{D4}$ is a leaving group selected from the group consisting of $—Br$, $—Cl$, $—I$, and $—OS(=O)_wR^{D4a}$, wherein w is 1 or 2, and $R^{D4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of $X^1$ is independently a bond, $—C(=O)—$, $—SO_2—$, $—NR^{D5}—$, optionally substituted alkylene, or optionally substituted heteroarylene, wherein $R^{D5}$ is hydrogen, $C_{1-6}$ alkyl, or a nitrogen protecting group;

each instance of Y is independently O, S, or $NR^{D6}$, wherein $R^{D6}$ is hydrogen, $C_{1-6}$ alkyl, or a nitrogen protecting group; and each instance of z and $z_1$ is independently 0, 1, 2, 3, 4, 5, or 6, as valency permits.

In certain embodiments, $R^D$ is a group of Formula (i-1), (i-3), or (i-20):

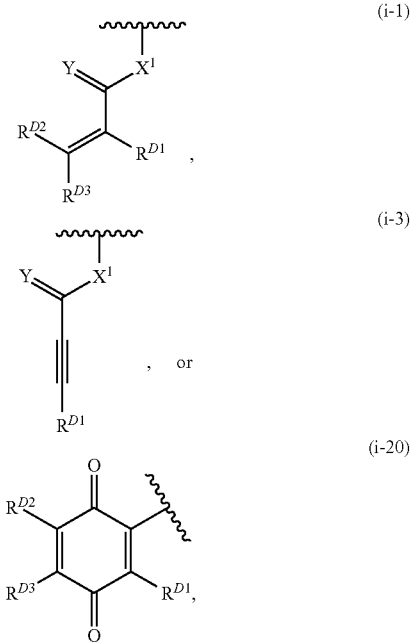

wherein each instance of $X^1$ is bond or $NR^{D5}$, Y is independently O, S, or $NR^{D6}$, and $R^{D1}$, $R^{D2}$, and $R^{D3}$ are as defined herein. In certain embodiments, $X^1$ is a bond. In certain embodiments, $X^1$ is $NR^{D5}$. In certain embodiments, Y is O. In certain embodiments, $R^{D1}$ is hydrogen. In certain embodiments, $R^{D1}$ is $—CN$. In certain embodiments, $R^{D2}$ is hydrogen. In certain embodiments, $R^{D3}$ is hydrogen. In certain embodiments, $R^{D2}$ is $—CH_2N(R^{D2a})_2$, and $R^{D3}$ is hydrogen. In certain embodiments, $R^{D2}$ is $—CH_2N(R^{D3a})_2$, and $R^{D3}$ is hydrogen. In certain embodiments, $R^{D2}$ and $R^{D3}$ are hydrogen. In certain embodiments, $R^{D1}$, $R^{D2}$ and $R^{D3}$ are hydrogen.

In certain embodiments, $R^D$ is a group of Formula (i-19), (i-17), or (i-18):

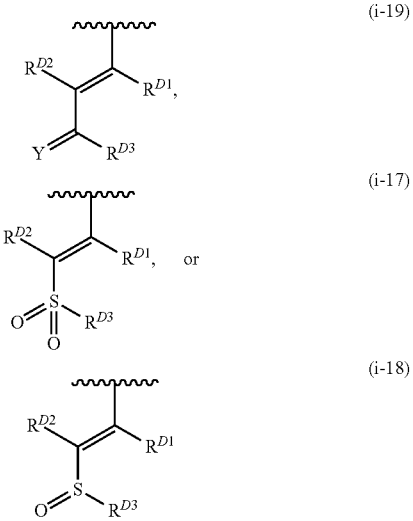

wherein Y is independently O, S, or NR$^{D6}$; and R$^{D1}$, R$^{D2}$, and R$^{D3}$ are as defined herein. In certain embodiments, Y is O. In certain embodiments, R$^{D1}$ is hydrogen. In certain embodiments, R$^{D2}$ is hydrogen. In certain embodiments, R$^{D2}$ is CN. In certain embodiments, R$^{D3}$ is substituted or unsubstituted alkyl.

In certain embodiments, R$^D$ is a group of Formula (i-7) or (i-8):

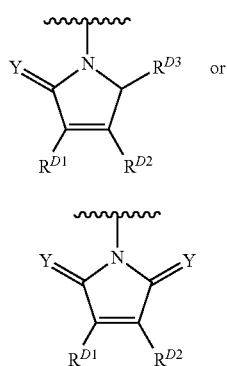

(i-7)

(i-8)

wherein Y is independently O, S, or NR$^{D6}$; and R$^{D1}$, R$^{D2}$, and R$^{D3}$ are as defined herein. In certain embodiments, Y is O. In certain embodiments, R$^{D1}$ is hydrogen. In certain embodiments, R$^{D2}$ is hydrogen. In certain embodiments, R$^{D3}$ is hydrogen.

In certain embodiments, R$^D$ is a group of Formula (i-13) or (i-14):

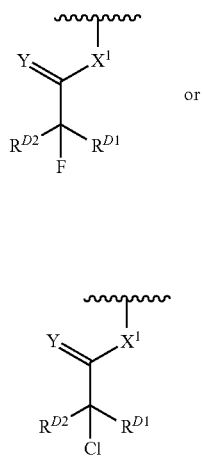

(i-13)

(i-14)

wherein each instance of X$^1$ is bond or NR$^{D5}$; Y is independently O, S, or NR$^{D6}$; and R$^{D1}$ and R$^{D2}$ are as defined herein. In certain embodiments, X$^1$ is a bond. In certain embodiments, X$^1$ is NR$^{D5}$. In certain embodiments, Y is O. In certain embodiments, R$^{D1}$ is hydrogen. In certain embodiments, R$^{D1}$ is halogen, e.g., —F or —Cl. In certain embodiments, R$^{D2}$ is hydrogen. In certain embodiments, R$^{D2}$ is halogen, e.g., —F or —Cl.

In certain embodiments, R$^D$ is a group of Formula (i-11) or (i-12):

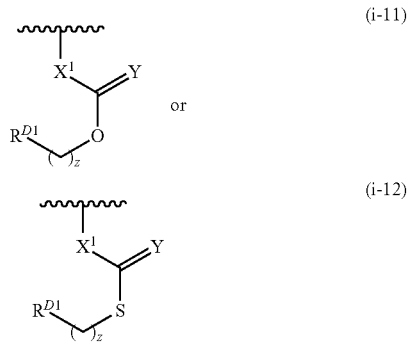

(i-11)

(i-12)

wherein each instance of X$^1$ is bond or NR$^{D5}$; Y is independently O, S, or NR$^{D6}$; z is 0, 1, 2, 3, 4, 5, or 6; and R$^{D1}$ is as defined herein. In certain embodiments, X$^1$ is a bond. In certain embodiments, X$^1$ is NR$^{D5}$. In certain embodiments, Y is O. In certain embodiments z is 0 or 1. In certain embodiments, R$^{D1}$ is substituted or unsubstituted alkyl.

In certain embodiments, R$^D$ is a group of Formula (i-10), (i-16), or (i-9):

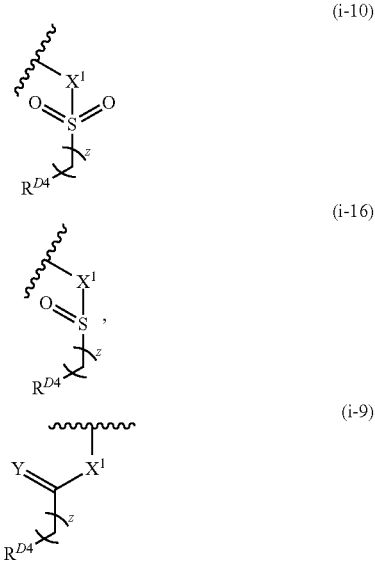

(i-10)

(i-16)

(i-9)

wherein each instance of X$^1$ is bond or NR$^{D5}$; Y is independently O, S, or NR$^{D6}$; z is 0, 1, 2, 3, 4, 5, or 6; and R$^{D4}$ is a leaving group selected from the group consisting of —Br, —Cl, —I, and —OS(=O)$_w$R$^{D4a}$, wherein w is 1 or 2. In certain embodiments, X$^1$ is a bond. In certain embodiments, X$^1$ is NR$^{D5}$. In certain embodiments, Y is O. In certain embodiments, z is 0. In certain embodiments, z is 1.

In certain embodiments, R$^D$ is a group of Formula (i-4) or (i-5):

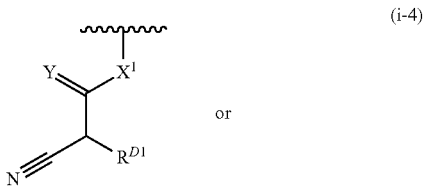

(i-4)

-continued

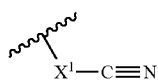
(i-5)

wherein each instance of $X^1$ is bond or $NR^{D5}$; and $R^{D1}$ is as defined herein. In certain embodiments, $X^1$ is a bond. In certain embodiments, $X^1$ is $NR^{D5}$. In certain embodiments, $R^{D1}$ is hydrogen.

In certain embodiments, $R^D$ is a group of Formula (i-6):

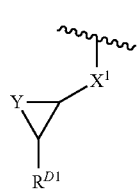
(i-6)

wherein each instance of $X^1$ is bond or $NR^{D5}$; Y is independently O, S, or $NR^{D6}$; and $R^{D1}$ is as defined herein. In certain embodiments, $X^1$ is a bond. In certain embodiments, $X^1$ is $NR^{D5}$. In certain embodiments, Y is O. In certain embodiments, $R^{D1}$ is hydrogen.

In certain embodiments, $R^D$ is a group of Formula (i-21)-(i-32), (i-39) and (i-40), wherein each instance of $X^1$ is independently a bond, —C(=O)—, —SO$_2$—, —NR$^{D5}$—, optionally substituted alkylene, or optionally substituted heteroarylene, wherein $R^{D5}$ is hydrogen, $C_{1-6}$ alkyl, or a nitrogen protecting group; Y is independently O, S, or $NR^{D6}$; and $R^{D1}$, $R^{D2}$, and $R^{D3}$ are as defined herein. In certain embodiments, $X^1$ is a bond. In certain embodiments, $X^1$ is —C(=O)—. In certain embodiments, $X^1$ is —SO$_2$—. In certain embodiments, $X^1$ is —NR$^{D5}$. In certain embodiments, $X^1$ is optionally substituted alkylene. In certain embodiments, $X^1$ is substituted alkylene. In certain embodiments, $X^1$ is unsubstituted alkylene. In certain embodiments, Y is O. In certain embodiments, Y is S. In certain embodiments, Y is $NR^{D6}$. In certain embodiments, $R^{D1}$ is hydrogen. In certain embodiments, $R^{D2}$ is hydrogen. In certain embodiments, $R^{D2}$ is —CN. In certain embodiments, $R^{D3}$ is substituted or unsubstituted alkyl.

In certain embodiments, $R^D$ is a group of Formulae (i-33) and (i-36)-(i-38), wherein each instance of $X^1$ is independently a bond, —C(=O)—, —SO$_2$—, —NR$^{D5}$, optionally substituted alkylene, or optionally substituted heteroarylene, wherein $R^{D5}$ is hydrogen, $C_{1-6}$ alkyl, or a nitrogen protecting group; and $R^{D1}$ is as defined herein. In certain embodiments, $X^1$ is optionally substituted heteroarylene. In certain embodiments, $X^1$ is optionally substituted heteroarylene. In certain embodiments, $X^1$ is optionally substituted five-membered heteroarylene. In certain embodiments, $X^1$ is optionally substituted five-membered heteroarylene with at least one S, O, and N. In certain embodiments, $X^1$ is optionally substituted six-membered heteroarylene. In certain embodiments, $X^1$ is optionally substituted six-membered heteroarylene with at least one S, O, and N.

In certain embodiments, $R^D$ is a group of Formula (i-34), wherein each instance of z and $R^{D1}$ are as defined herein. In certain embodiments, $R^{D1}$ is halogen. In certain embodiments, $R^{D1}$ is F. In certain embodiments, $R^{D1}$ is Cl. In certain embodiments, $R^{D1}$ is Br. In certain embodiments, $R^{D1}$ is I In certain embodiments, $R^{D1}$ is CN. In certain embodiments, $R^{D1}$ is NO$_2$.

As used herein, each of z and z1 is independently 0, 1, 2, 3, 4, 5, or 6, as valency permits. In certain embodiments, z is 0. In certain embodiments, z is 1. In certain embodiments, z is 2. In certain embodiments, z is 3. In certain embodiments, z is 4. In certain embodiments, z is 5. In certain embodiments, z is 6. In certain embodiments, z1 is 0. In certain embodiments, z1 is 1. In certain embodiments, z1 is 2. In certain embodiments, z1 is 3. In certain embodiments, z1 is 4. In certain embodiments, z1 is 5. In certain embodiments, z1 is 6.

In certain embodiments, $R^D$ is

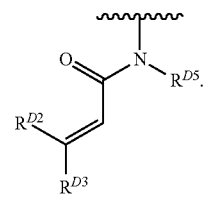

In certain embodiments, $R^D$ is

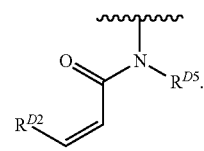

In certain embodiments, $R^D$ is

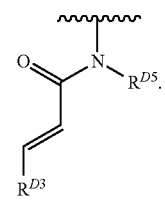

In certain embodiments, $R^D$ is

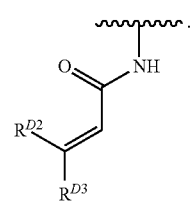

In certain embodiments, $R^D$ is

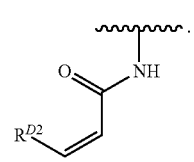

In certain embodiments, $R^D$ is

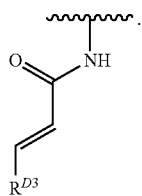

In certain embodiments, $R^D$ is

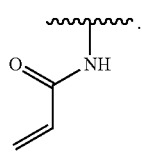 [SMILES: *NC(=O)C=C]

In certain embodiments, $R^D$ is

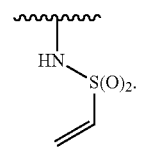

In certain embodiments, $R^D$ is

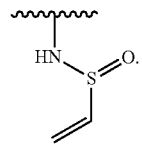

In certain embodiments, $R^D$ is

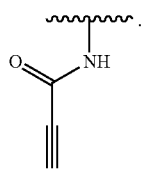

In certain embodiments, $R^D$ is

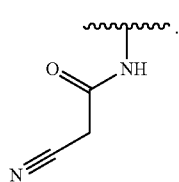

In certain embodiments, $R^D$ is

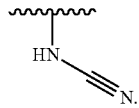 [SMILES: *NC#N]

In certain embodiments, $R^D$ is

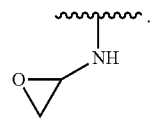

In certain embodiments, $R^D$ is

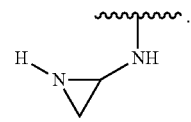

In certain embodiments, $R^D$ is

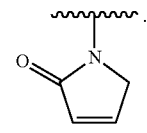

In certain embodiments, $R^D$ is

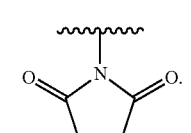

In certain embodiments, $R^D$ is

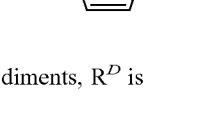

In certain embodiments, $R^D$ is

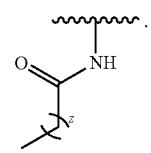

In certain embodiments, $R^D$ is

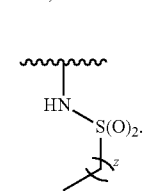

In certain embodiments, $R^D$ is
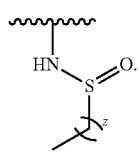
In certain embodiments, $R^D$ is
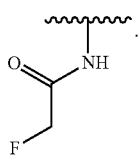
In certain embodiments, $R^D$ is
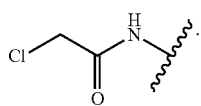
In certain embodiments, $R^D$ is
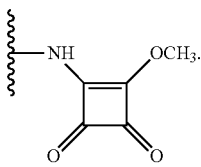 [SMILES: *Nc1c(OC)c(=O)c1=O]
In certain embodiments, $R^D$ is
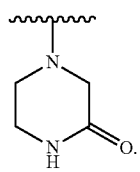 [SMILES: *N1CCNC(=O)C1]
In certain embodiments, $R^D$ is selected from one of the following formulae:
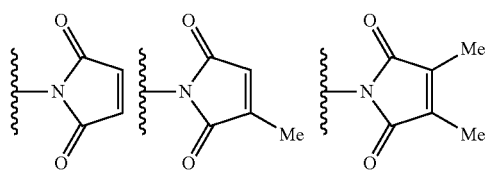
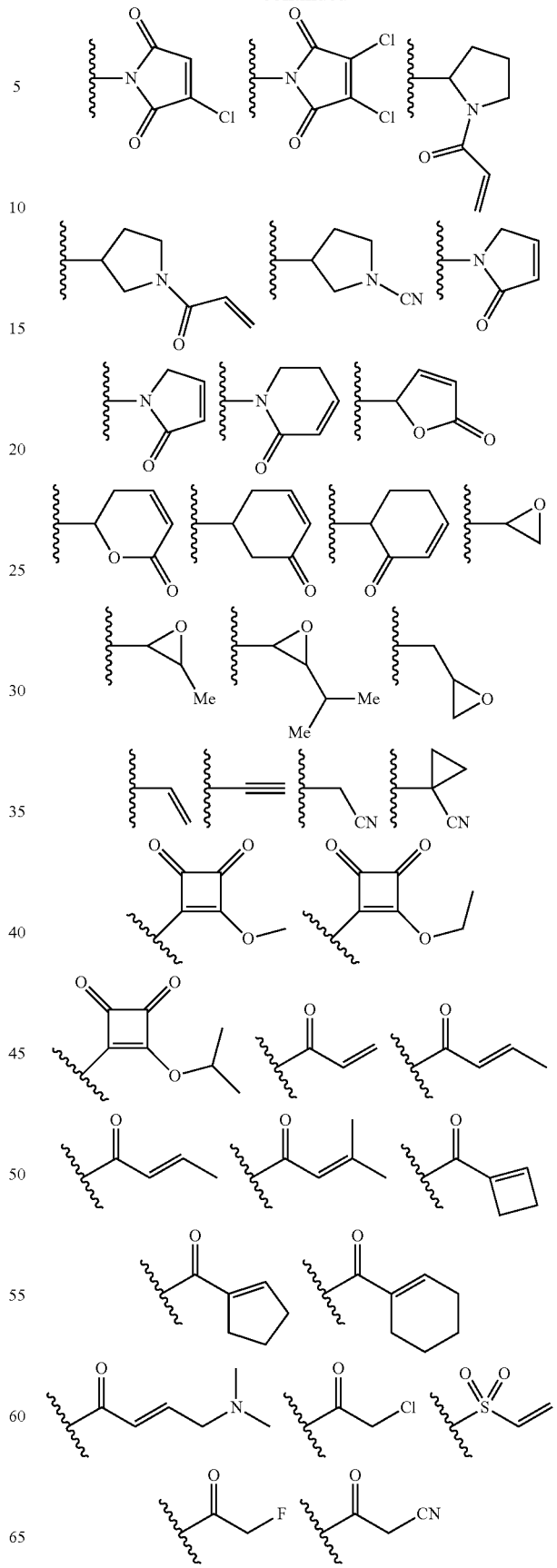

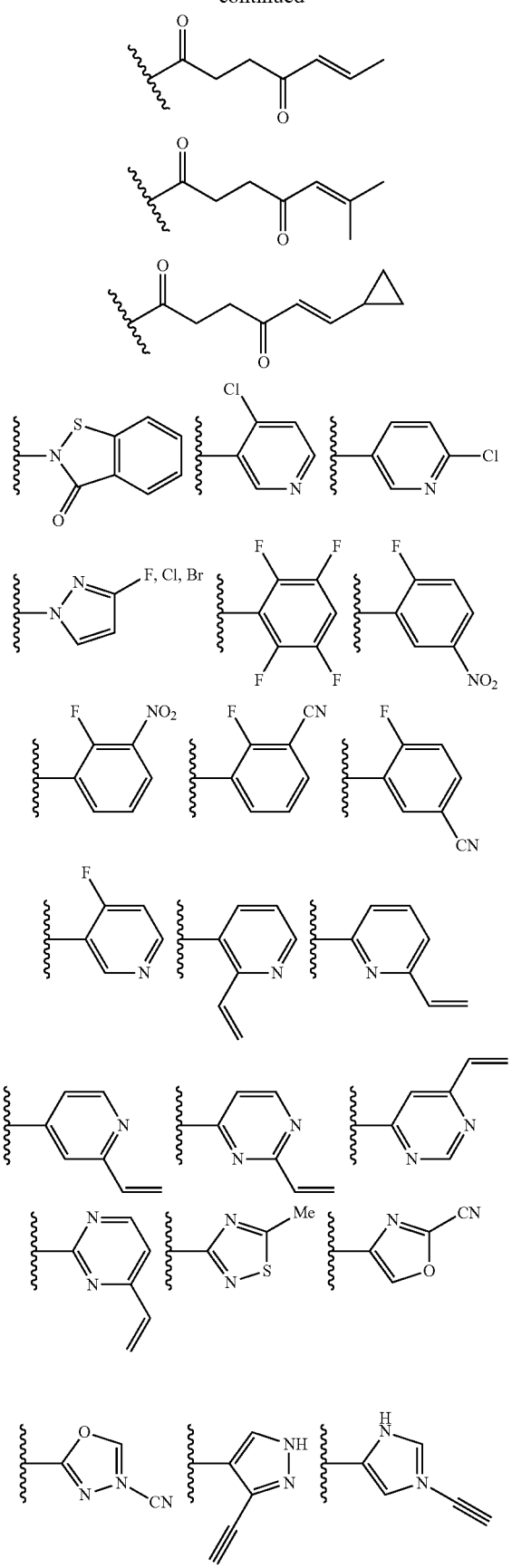
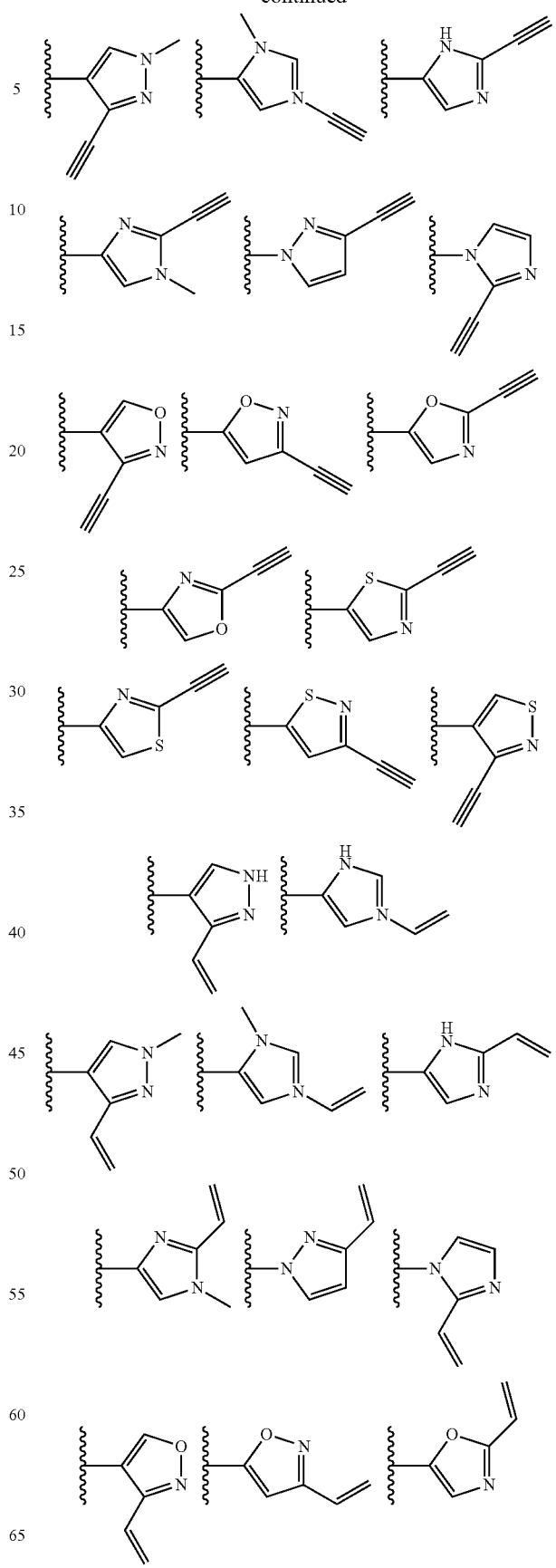

-continued

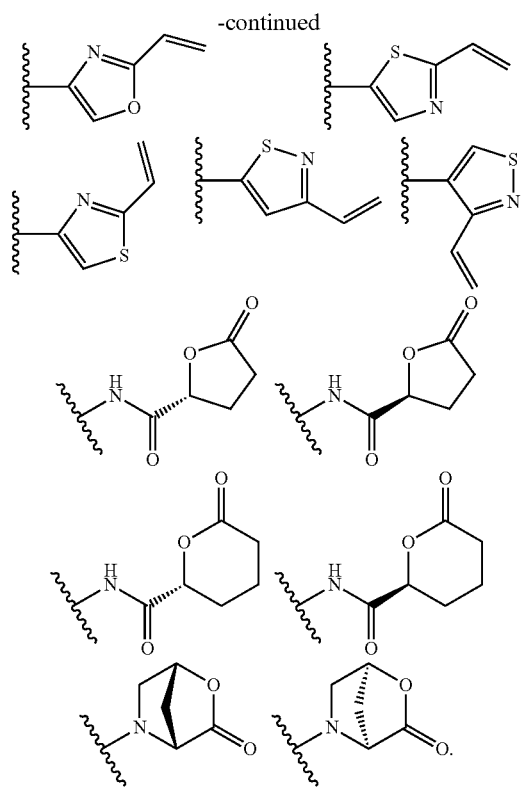

In certain embodiments, the compound of Formula (I) is of Formula (I-a):

(I-a)

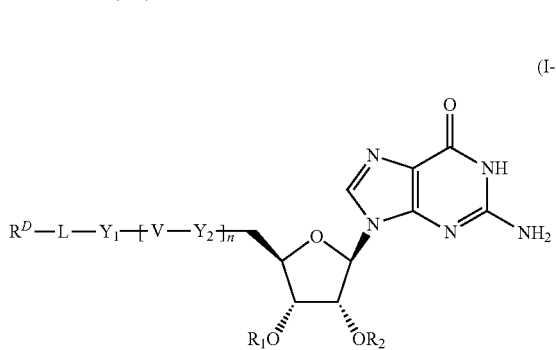

or a pharmaceutically acceptable salt thereof, wherein $Y_1$, V, $Y_2$, $R^D$, L, $R_1$, $R_2$, and n are as defined herein.

In certain embodiments, the compound of Formula (I) is of the Formula (I-b):

(I-b)

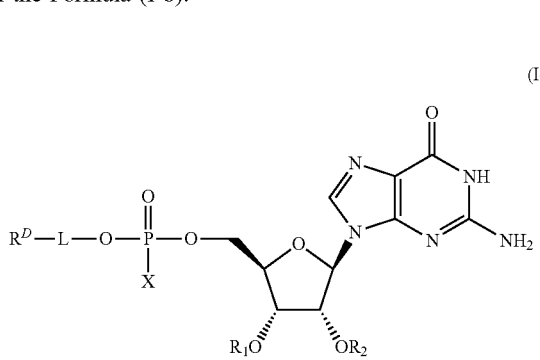

or a pharmaceutically acceptable salt thereof, wherein $Y_1$, V, $Y_2$, $R^D$, L, $R_1$, $R_2$, and n are as defined herein.

In certain embodiments, the compound of Formula (I) is of the Formula (I-b1):

(I-b1)

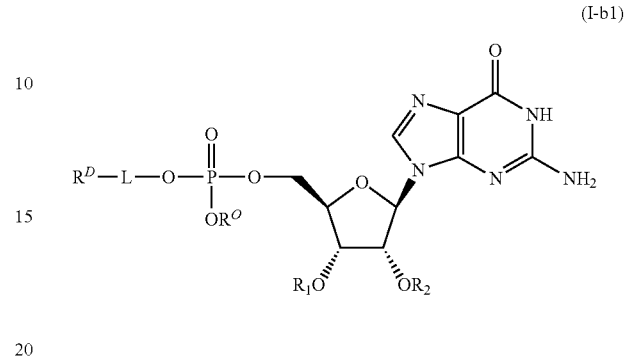

or a pharmaceutically acceptable salt thereof, wherein $R^O$, $R^D$, $R_1$, $R_2$, and L are as defined herein.

In certain embodiments, the compound of Formula (I) is of the Formula (I-c):

(I-c)

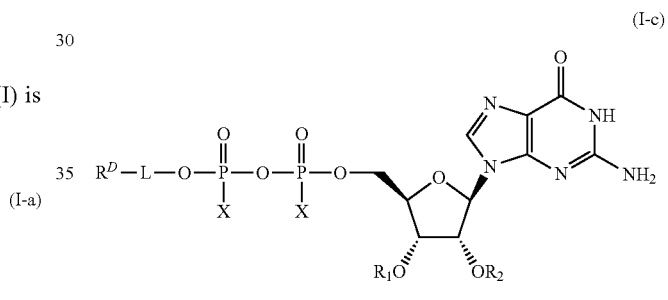

or a pharmaceutically acceptable salt thereof, wherein X, $R^D$, $R_1$, $R_2$, and L are as defined herein.

In certain embodiments, the compound of Formula (I) is of the Formula (I-c1):

(I-c1)

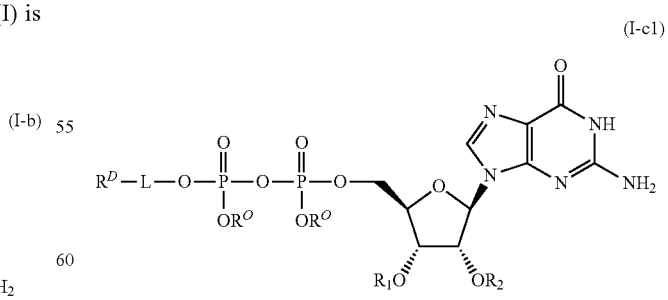

or a pharmaceutically acceptable salt thereof, wherein $R^O$, $R^D$, $R_1$, $R_2$, and L are as defined herein.

In certain embodiments, the compound of Formula (I) is of the Formula (I-c2):

(I-c2)

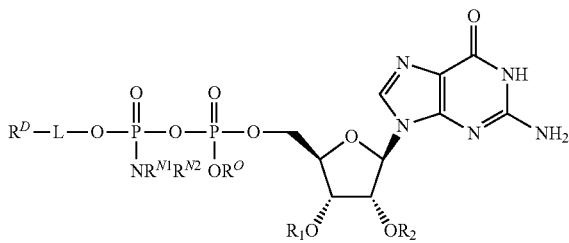

or a pharmaceutically acceptable salt thereof, wherein $R^{N1}$, $R^{N2}$, $R^O$, $R^D$, $R_1$, $R_2$, and L are as defined herein.

In certain embodiments, the compound of Formula (I) is of the Formula (I-c2-1):

(I-c2-1)

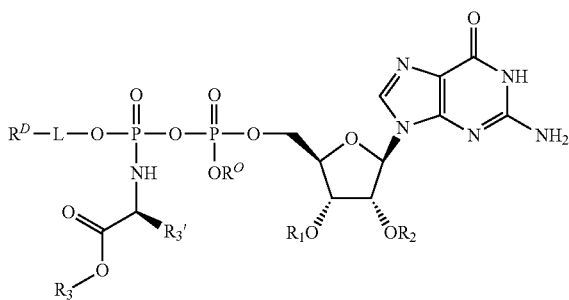

or a pharmaceutically acceptable salt thereof, wherein $R_3$, $R_3'$, $R^O$, $R^D$, $R_1$, $R_2$, and L are as defined herein.

In certain embodiments, the compound of Formula (I) is of the Formula (I-d):

(I-d)

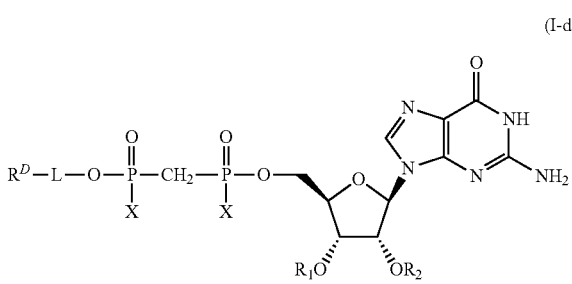

or a pharmaceutically acceptable salt thereof, wherein X, $R^D$, $R_1$, $R_2$, and L are as defined herein.

In certain embodiments, the compound of Formula (I) is of the Formula (I-d1):

(I-d1)

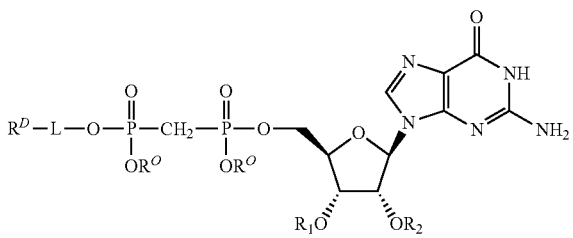

or a pharmaceutically acceptable salt thereof, wherein $R^O$, $R^D$, $R_1$, $R_2$, and L are as defined herein.

In certain embodiments, the compound of Formula (I) is of the Formula (I-d2):

(I-d2)

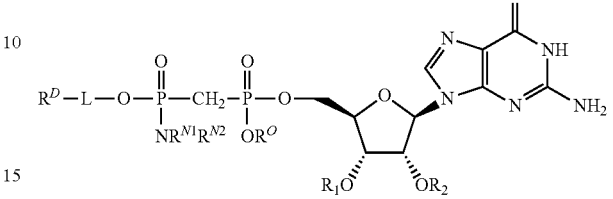

or a pharmaceutically acceptable salt thereof, wherein $R^{N1}$, $R^{N2}$, $R^O$, $R^D$, $R_1$, $R_2$, and L are as defined herein.

In certain embodiments, the compound of Formula (I) is of the Formula (I-e):

(I-e)

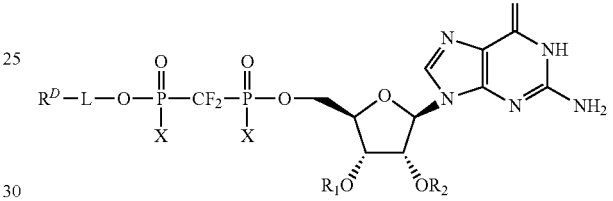

or a pharmaceutically acceptable salt thereof, wherein X, $R^D$, $R_1$, $R_2$, and L are as defined herein.

In certain embodiments, the compound of Formula (I) is of the Formula (I-e1):

(I-e1)

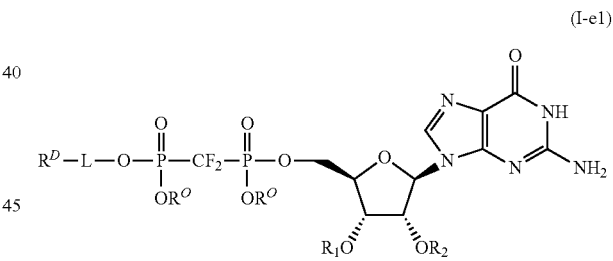

or a pharmaceutically acceptable salt thereof, wherein $R^O$, $R^D$, $R_1$, $R_2$, and L are as defined herein.

In certain embodiments, the compound of Formula (I) is of the Formula (I-e2):

(I-e2)

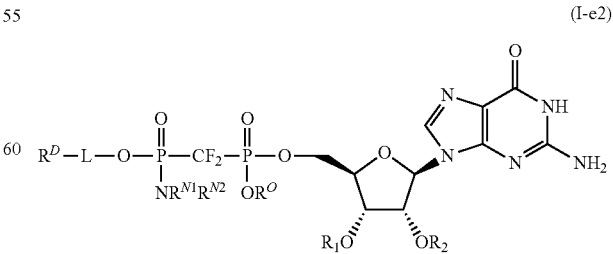

or a pharmaceutically acceptable salt thereof, wherein $R^{N1}$, $R^{N2}$, $R^O$, $R^D$, $R_1$, $R_2$, and L are as defined herein.

In certain embodiments, the compound of Formula (I) is of the Formula (I-f):

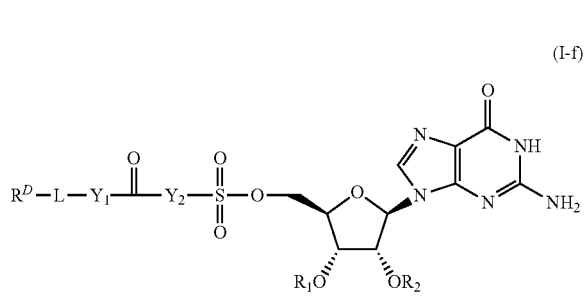

(I-f)

or a pharmaceutically acceptable salt thereof, wherein $Y_1$, $Y_2$, $R^D$, $R_1$, $R_2$, and L are as defined herein.

In certain embodiments, the compound of Formula (I) is of the Formula (I-f1):

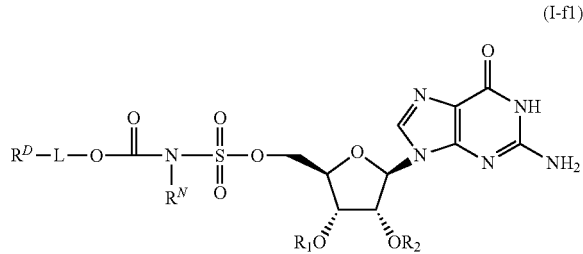

(I-f1)

or a pharmaceutically acceptable salt thereof, wherein $R^N$, $R^D$, $R_1$, $R_2$, and L are as defined herein.

In certain embodiments, the compound of Formula (II):

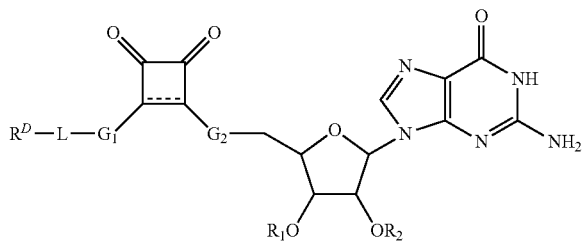

(II)

or a pharmaceutically acceptable salt thereof, wherein $G_1$, $G_2$, $R^D$, $R_1$, $R_2$, and L are as defined herein.

In certain embodiments, the compound of Formula (II-a):

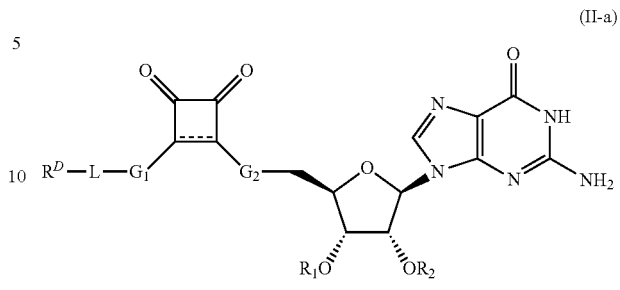

(II-a)

or a pharmaceutically acceptable salt thereof, wherein $G_1$, $G_2$, $R^D$, $R_1$, $R_2$, and L are as defined herein.

In certain embodiments, the compound of Formula (II-a1):

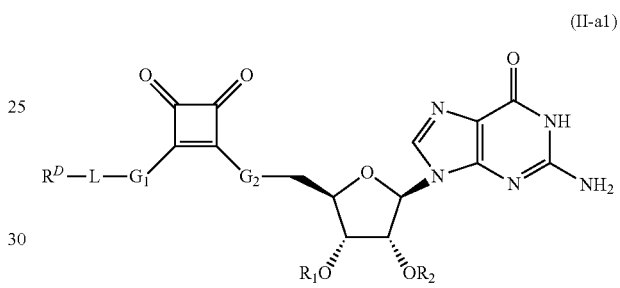

(II-a1)

or a pharmaceutically acceptable salt thereof, wherein $G_1$, $G_2$, $R^D$, $R_1$, $R_2$, and L are as defined herein.

In certain embodiments, the compound of Formula (II-a2):

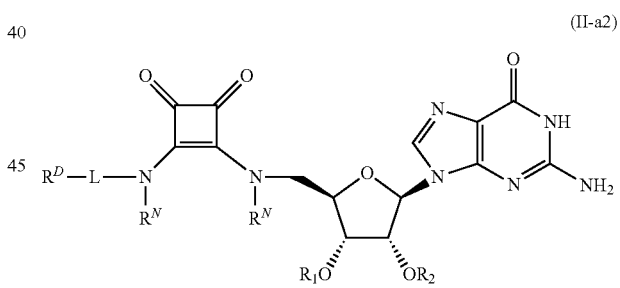

(II-a2)

or a pharmaceutically acceptable salt thereof, wherein $R^N$, $R^D$, $R_1$, $R_2$, and L are as defined herein.

Exemplary compounds of Formulae (I)-(II) include, but are not limited to:

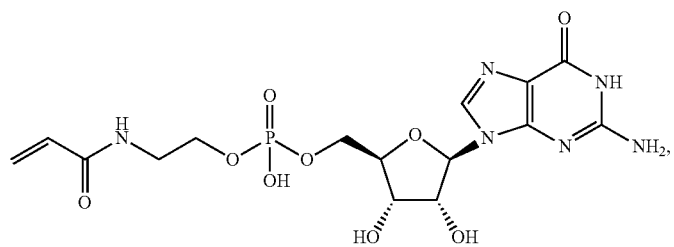 [SMILES: C=CC(=O)NCCOP(=O)(O)OC[C@H]1O[C@@H](n2cnc3c(=O)[nH]c(N)nc32)[C@H](O)[C@@H]1O]

-continued
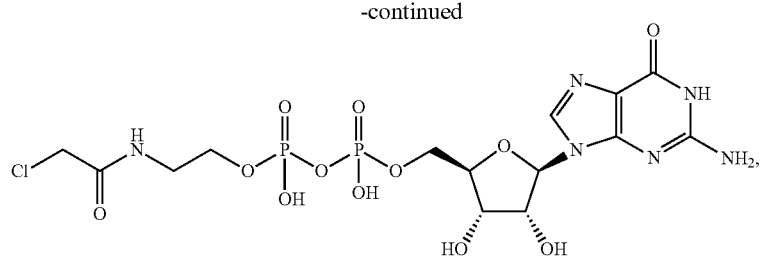
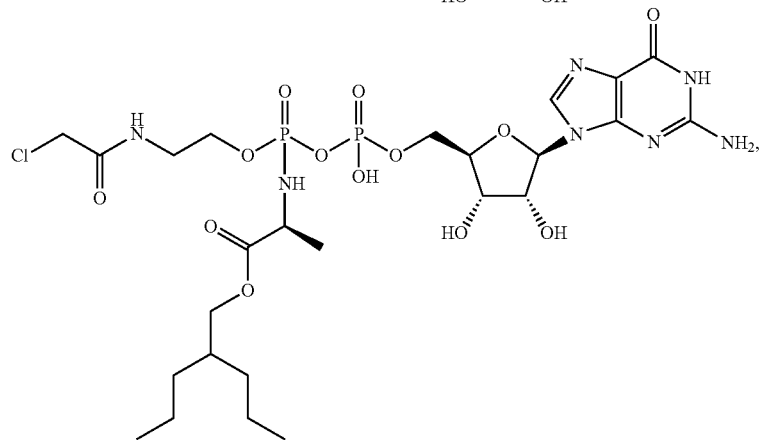
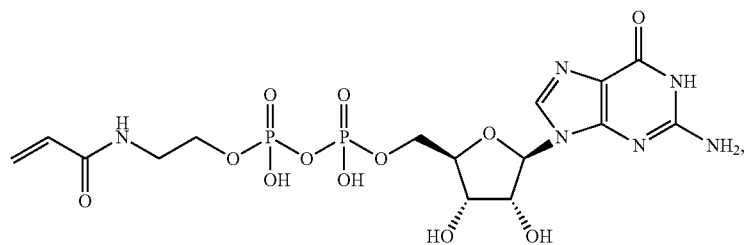
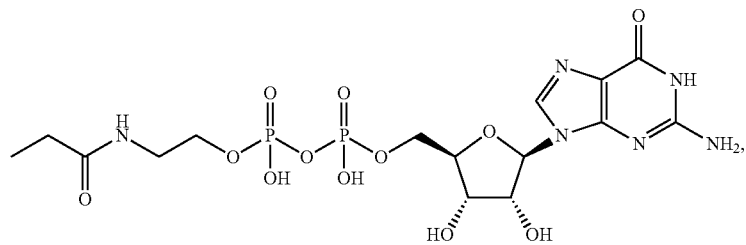
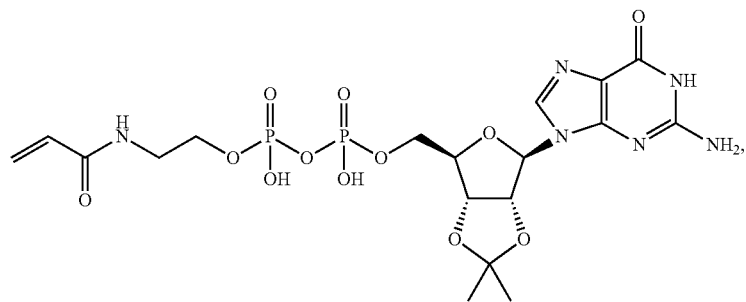

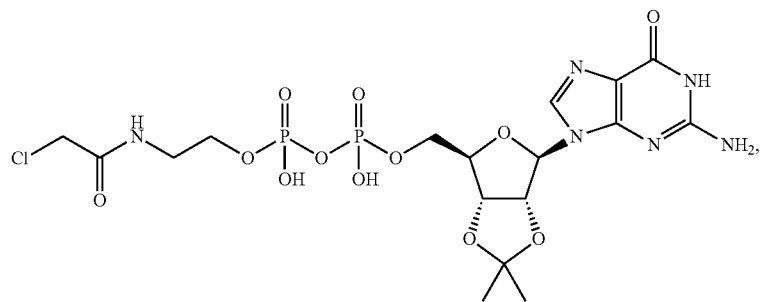
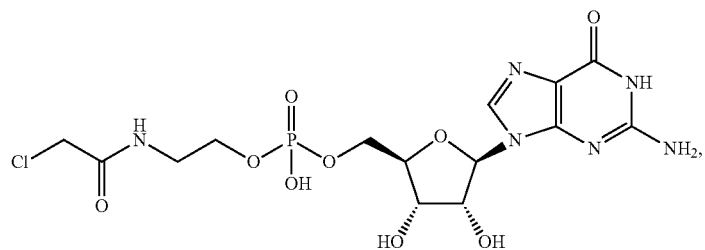
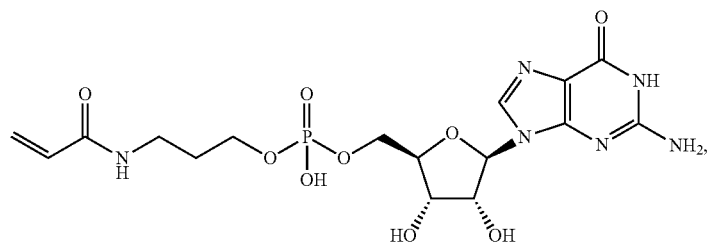
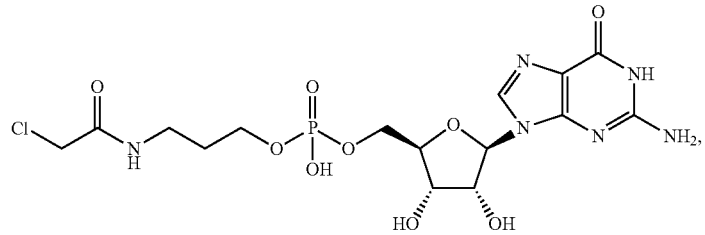
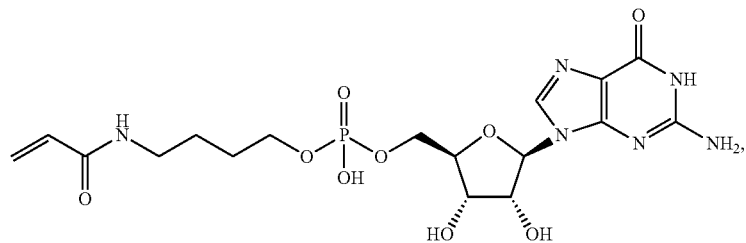
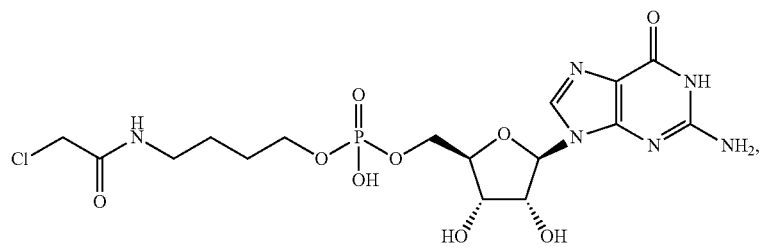

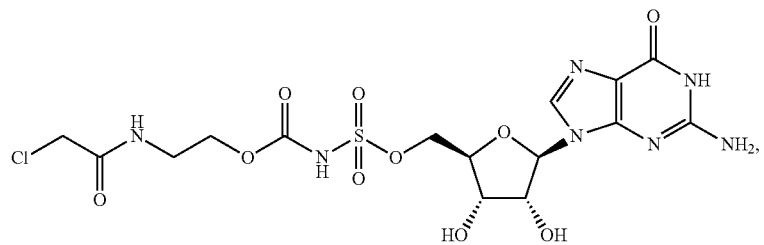
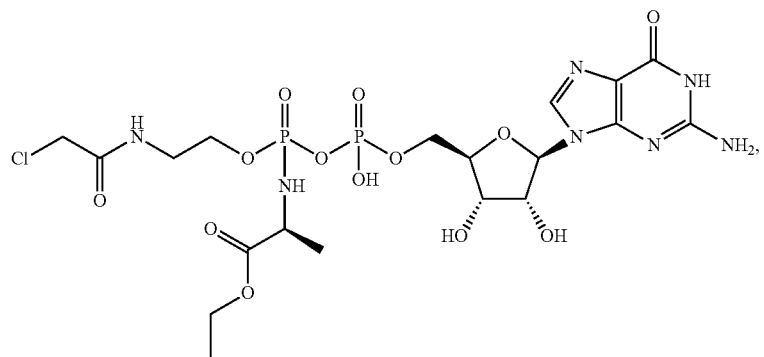
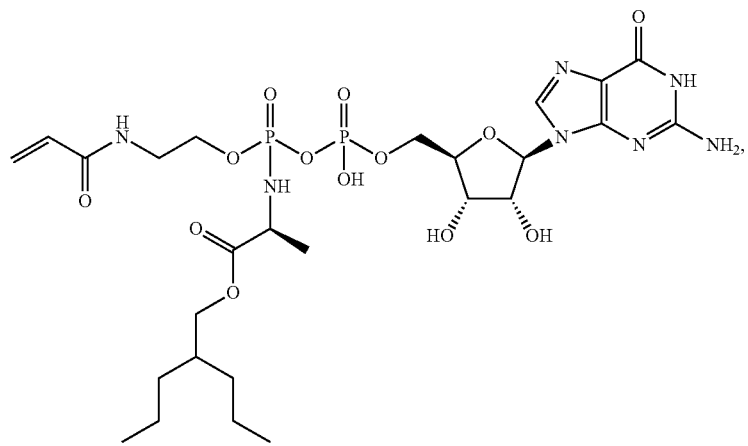
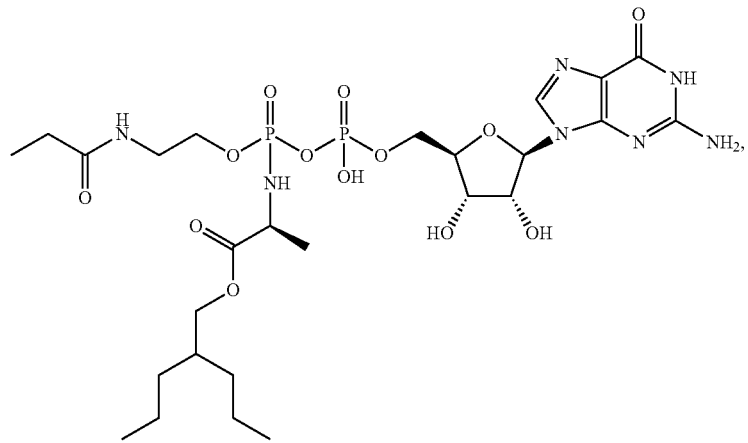

-continued
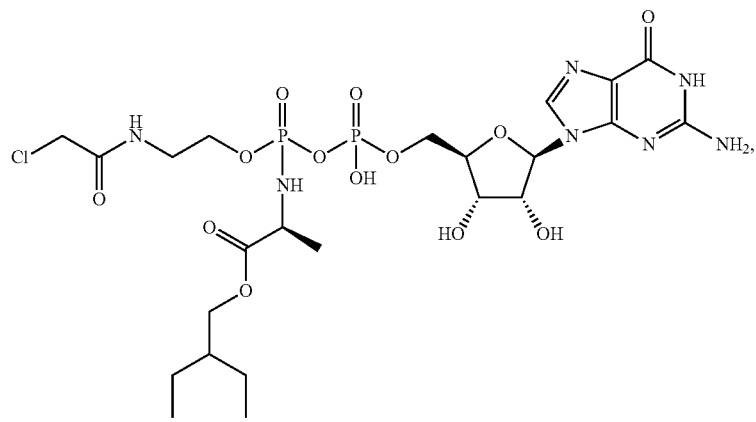
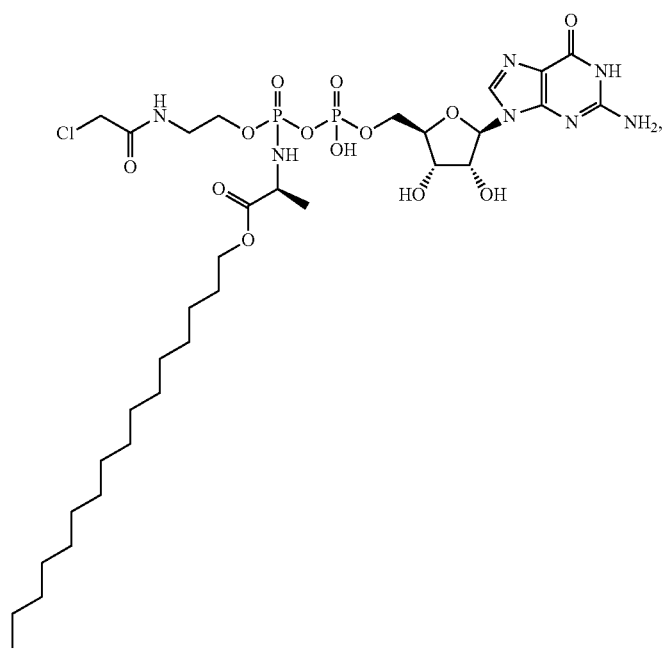
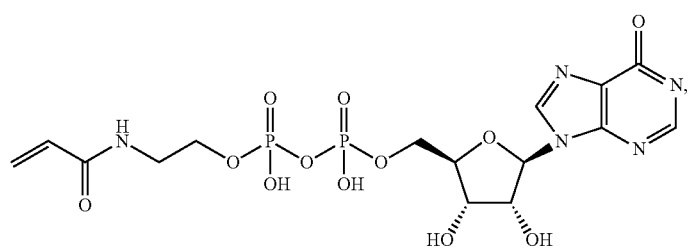
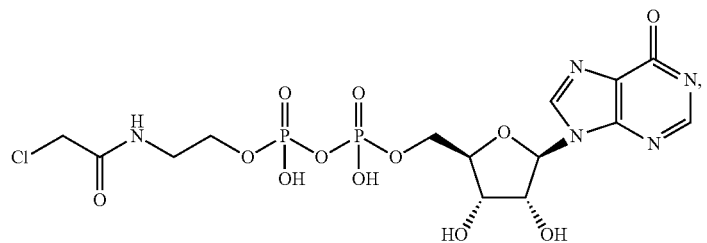

-continued
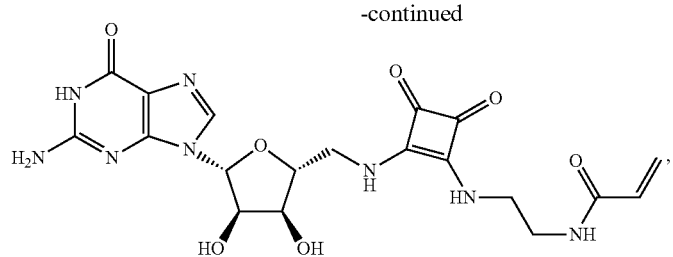
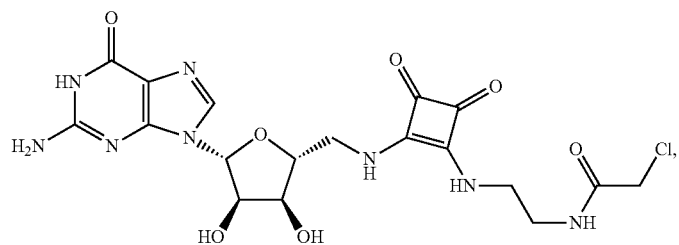
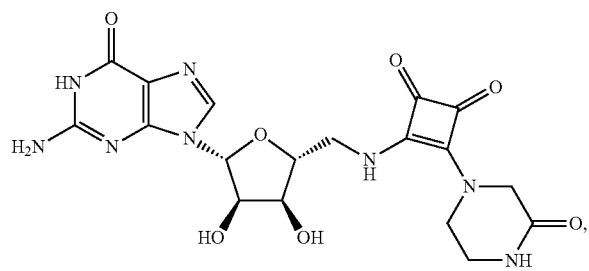
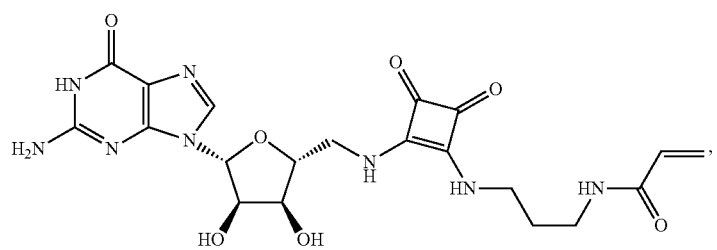
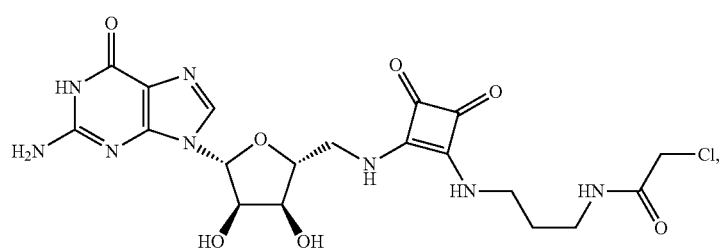

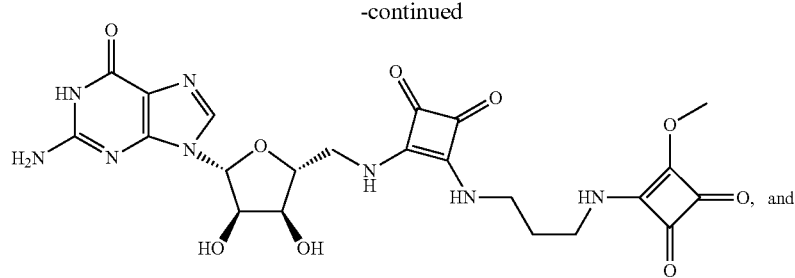

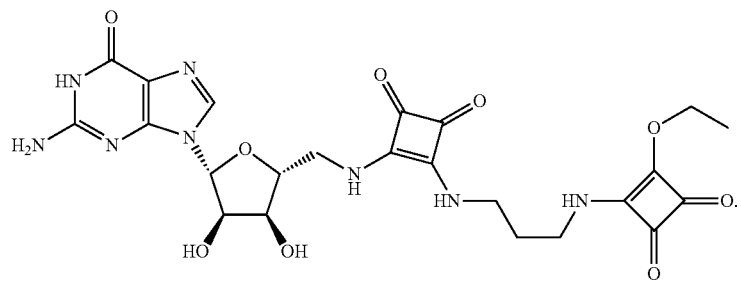

Additional exemplary compounds of Formulae (I)-(II) include, but are not limited to:

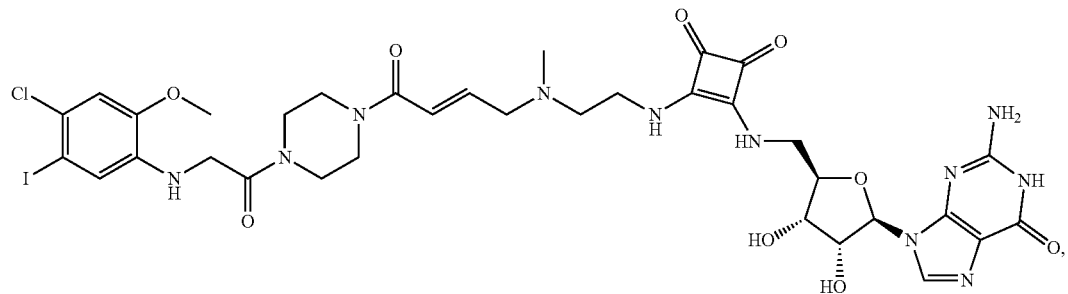

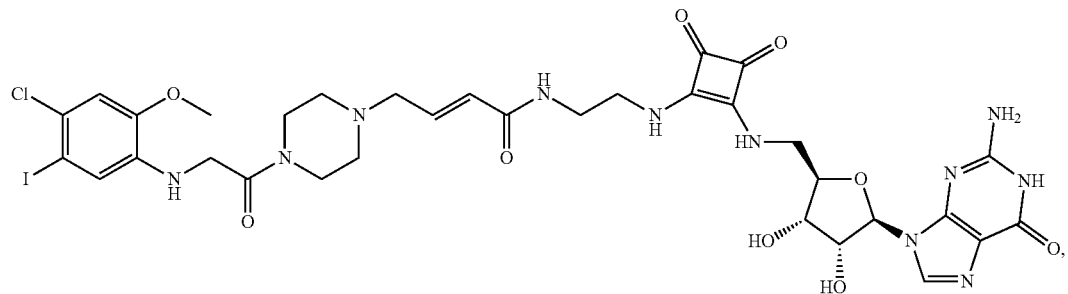

and pharmaceutically acceptable salts, solvates, hydrates, polymorphs, co-crystals, tautomers, stereoisomers, isotopically labeled derivatives, and prodrugs thereof.

Synthetic Methods

In some embodiments, compounds described herein can be prepared using methods shown in Schemes 1-4. Details of the synthetic procedures are described in the Examples below.

Scheme 1
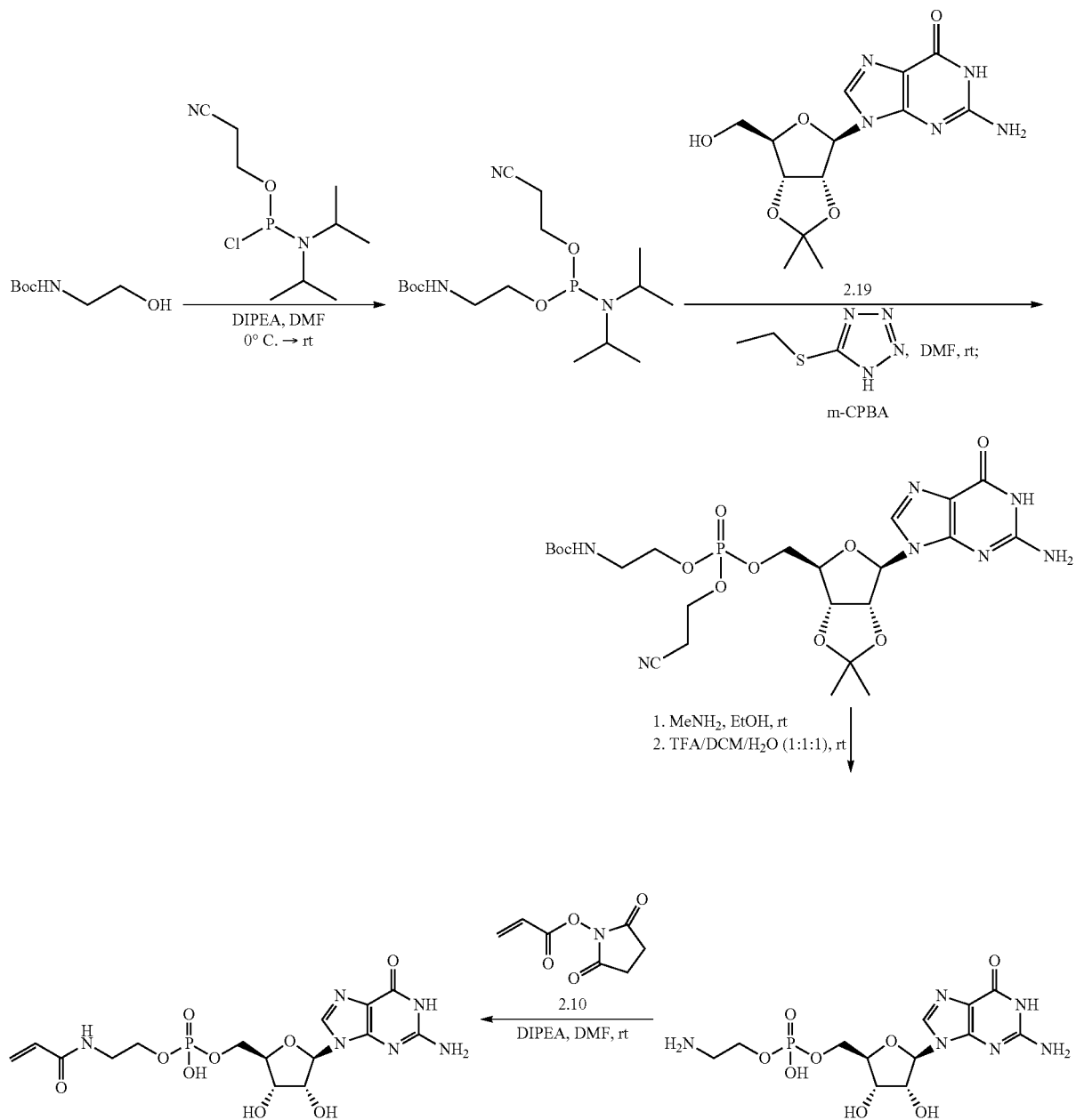
Scheme 2
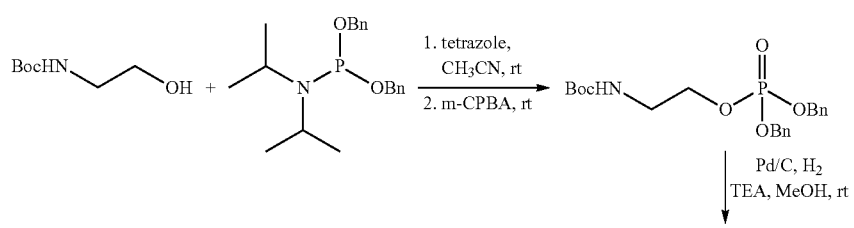

105
106
-continued
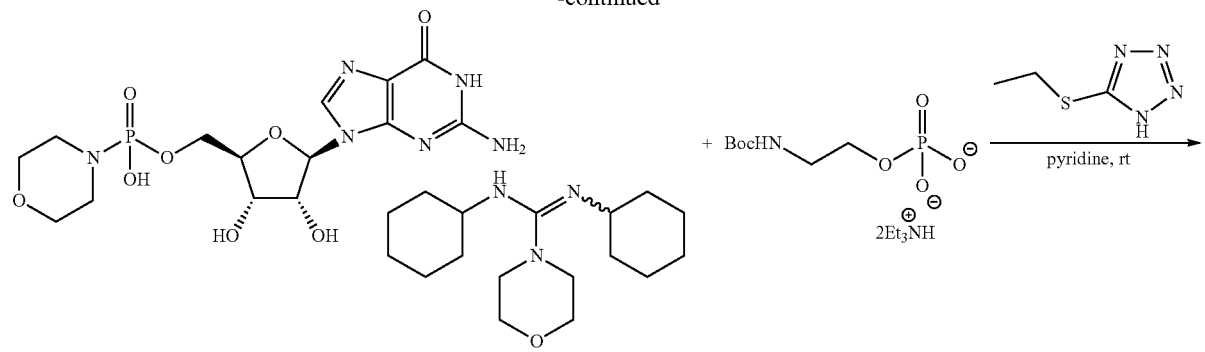
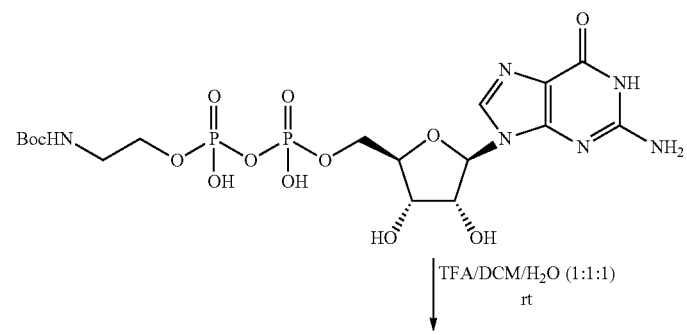
TFA/DCM/H$_2$O (1:1:1)
rt
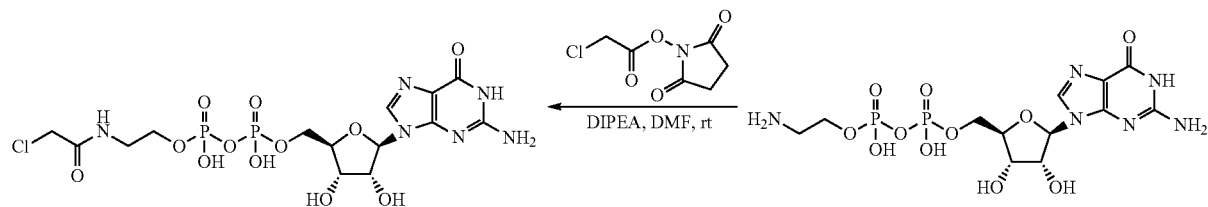
Scheme 3
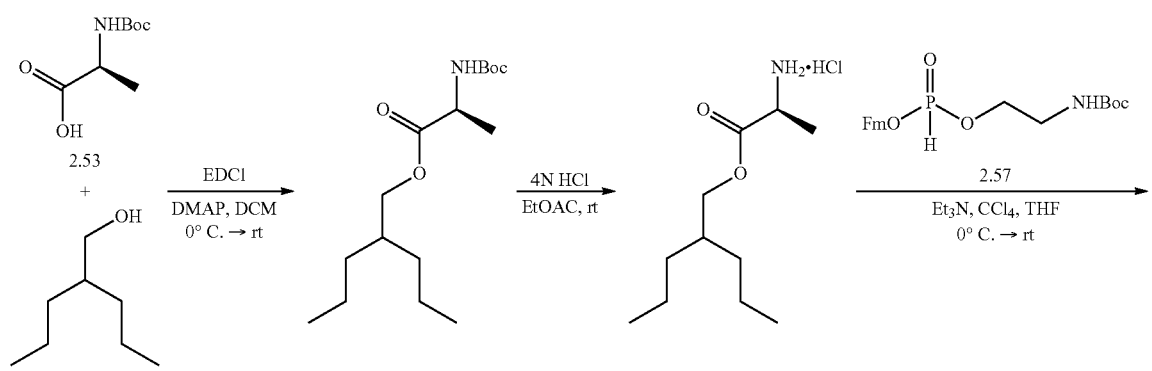

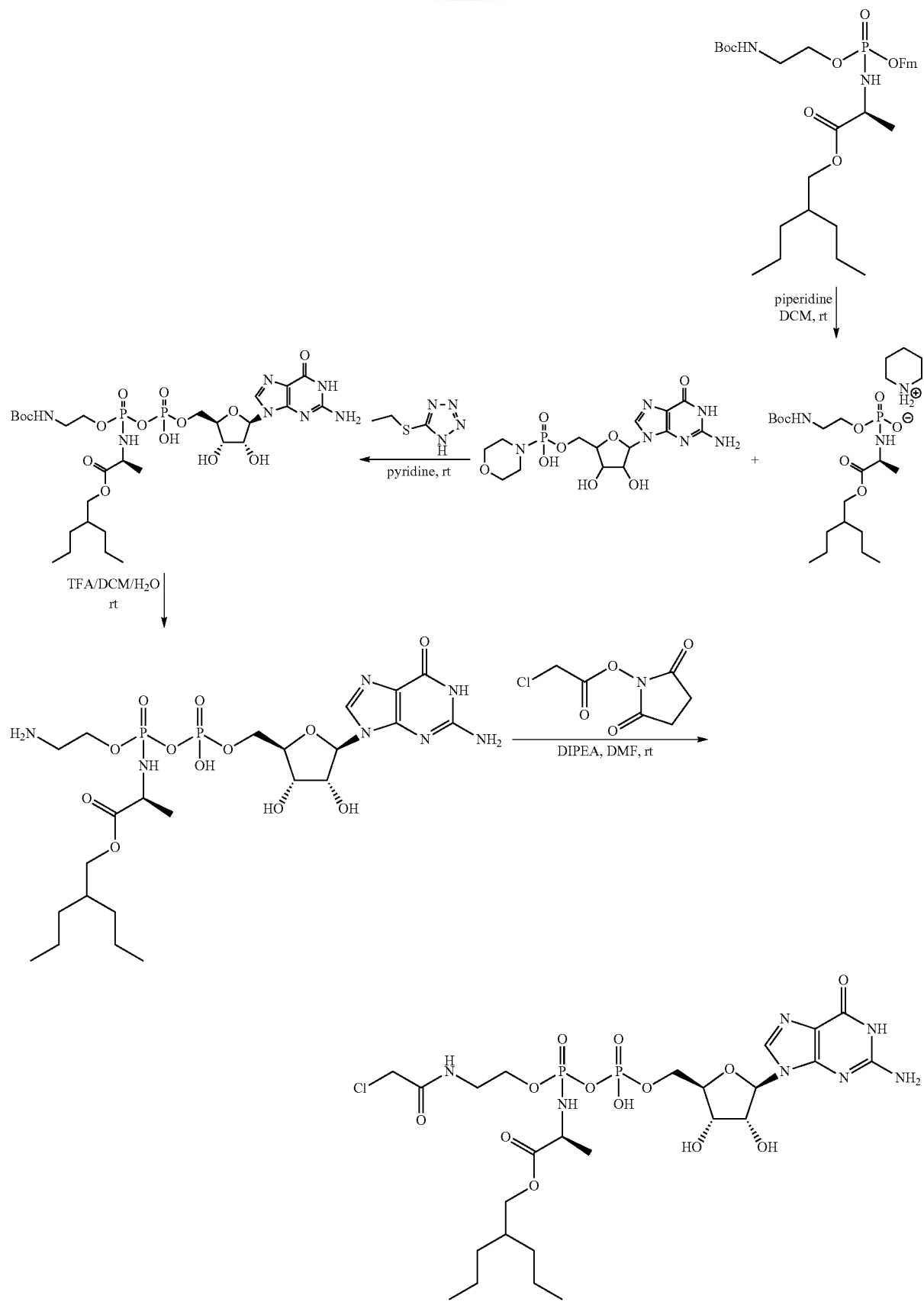

Scheme 4

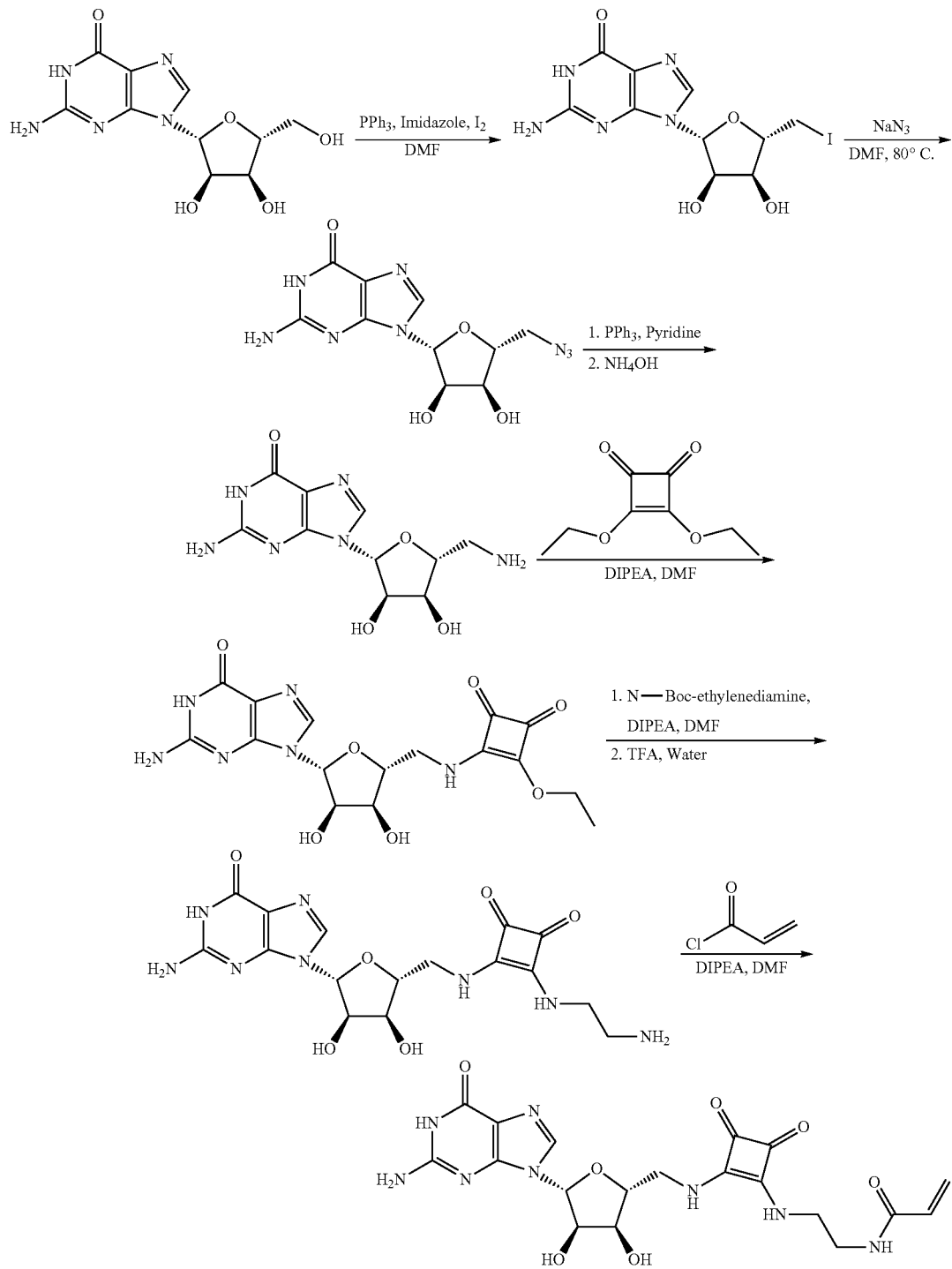

Pharmaceutical Compositions, Kits, and Administration

The present invention provides pharmaceutical compositions comprising a compound of Formula (I) or (II), or a pharmaceutically acceptable salt, solvate, hydrate, polymorph, co-crystal, tautomer, stereoisomer, isotopically labeled derivative, or prodrug thereof, as described herein, and optionally a pharmaceutically acceptable excipient. In certain embodiments, the pharmaceutical composition of the invention comprises a compound of Formula (I) or (II), or a pharmaceutically acceptable salt thereof, and optionally a pharmaceutically acceptable excipient. In certain embodiments, the compound of Formula (I) or (II), or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) or (II) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, and prodrug thereof, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, polymorph, co-crystal, tautomer, stereoisomer, isotopically labeled derivative, and prodrug thereof, or a pharmaceutical composition thereof, to a subject to prevent and/or treat a proliferative disease.

Methods of Treatment and Uses

The present invention also provides methods of using the compounds of Formula (I) or a pharmaceutically acceptable salt, solvate, hydrate, polymorph, co-crystal, tautomer, stereoisomer, isotopically labeled derivative, and prodrug thereof, or a pharmaceutical composition thereof, for the treatment or prevention of a proliferative disease such as cancer (e.g. lung cancer, large bowel cancer, pancreas cancer, biliary tract cancer, or endometrial cancer), benign neoplasm, angiogenesis, inflammatory disease, autoinflammatory disease, or autoimmune disease in a subject.

The proliferative disease to be treated or prevented using the compounds of Formula (I) may be associated with overactivity of Ras or aberrant signaling of Ras. In certain embodiments, the overactivity of Ras or aberrant signaling of Ras is due to a Ras mutation. In certain embodiments, the Ras protein is K-Ras. In certain embodiments, the Ras protein is K-Ras G12C. In certain embodiments, the compounds of Formula (I) or (II) target the guanine nucleotide (GN) binding site of Ras. In certain embodiments, the compound of Formula (I) or (II) forms a covalent bond with cysteine 12 in the GN binding pocket. In certain embodiments, the compound of Formula (I) forms a covalent bond with lysine 16 in the GN binding pocket. In certain embodiments, the covalent binding of the compound of Formula (I) or (II) in the GN binding pocket prevents further nucleotide exchange to activate Ras, thus keeping Ras in an inactive state.

In some embodiments, compounds described here are useful in treating proliferative diseases such as cancer, inflammatory diseases, autoimmune diseases, and autoinflammatory diseases.

In some embodiments, a provided compound is useful in treating a cancer. In some embodiments, a provided compound is useful to delay the onset of, slow the progression of, or ameliorate the symptoms of cancer. In some embodiments, a provided compound is administered in combination with other compounds, drugs, or therapeutics to treat cancer.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), nonsmall cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, a provided compound is useful in treating lung cancer. In some embodiments, a provided compound is useful in treating lung cancer. In some embodiments, a provided compound is useful in treating large bowel cancer. In some embodiments, a provided compound is useful in treating pancreas cancer. In some embodiments, a provided compound is useful in treating biliary tract cancer or endometrial cancer.

In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a cancer cell. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

The present invention also provides methods of inhibiting cell growth in a biological sample or subject.

In still another aspect, the present invention provides methods of inducing apoptosis of a cell in a biological sample or a subject.

In still another aspect, the present invention provides methods of inhibiting Ras activity or Ras signaling in a biological sample or a subject.

In certain embodiments, the methods described herein include administering to a subject or contacting a biological sample with an effective amount of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound of Formula (I), or a pharmaceutically acceptable salt thereof, or a pharmaceutical composition thereof.

In certain embodiments, the compound is administered in combination with one or more additional pharmaceutical agents described herein. In certain embodiments, the additional pharmaceutical agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin aminopterin, and hexamethyl melamine.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

EXAMPLES

In order that the invention described herein may be more fully understood, the following examples are set forth. It should be understood that these examples are for illustrative purposes only and are not to be construed as limiting this invention in any manner.

Commercially available reagents and solvents were used without further purification. All reactions were monitored by thin layer chromatography (TLC) with 0.25 mm E. Merck pre-coated silica gel plates (60 $F_{254}$) and/or Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ C18 column (4.6×50 mm, 5 μm particle size): Method A; solvent gradient=99% A at 0 min, 0% A at 5 min; Method B; solvent gradient=99% A at 0 min, 50% A at 5 min solvent A=0.035% TFA in Water; solvent B=0.035% TFA in MeOH; flow rate: 2.5 mL/min. Purification of reaction products was carried out by flash chromatography using CombiFlash® Rf with Teledyne Isco RediSep® Rf High Performance Gold or Silicycle SiliaSep™ High Performance columns (4 g, 12 g, or 24 g) and Waters LCMS system using SunFire™ Prep C18 column (19×50 mm, 5 μm particle size): solvent gradient=100% A at 0 min, 20% A at 6 min; solvent A=0.035% TFA in Water; solvent B=0.035% TFA in MeOH; flow rate: 25 mL/min. The purity of all compounds was over 95% and was analyzed with Waters LCMS system. $^1$H NMR spectra were obtained using a Varian Inova-500 or 600 (500 or 600 MHz for $^1$H NMR) spectrometer. Chemical shifts are reported relative to chloroform (δ=7.26) for ¹H NMR or dimethyl sulfoxide (δ=2.50) for ¹H. Data are reported as (br=broad, s=singlet, d=doublet, t=triplet, q=quartet, m=multiplet).
Compounds
Example 1
2-acrylamidoethyl(((2R,3S,4R,5R)-5-(2-amino-6-oxo-1H-purin-9(6H)-yl)-3,4-dihydroxytetrahydrofuran-2-yl)methyl) hydrogen phosphate
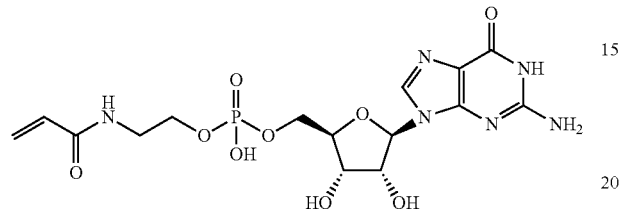
Scheme 1.
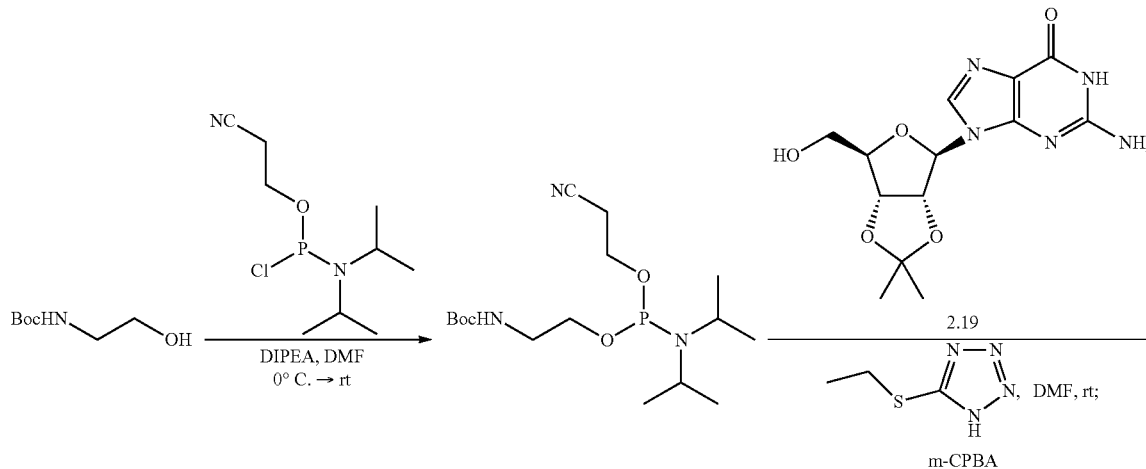
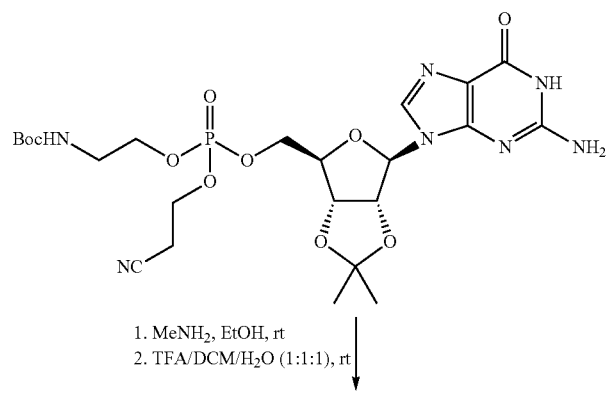
1. MeNH₂, EtOH, rt
2. TFA/DCM/H₂O (1:1:1), rt

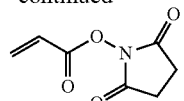
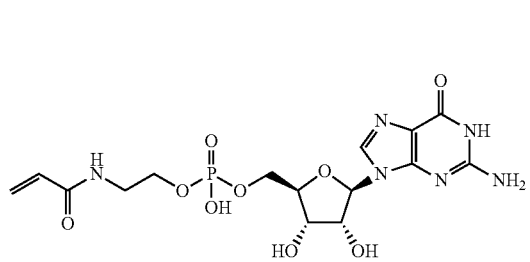
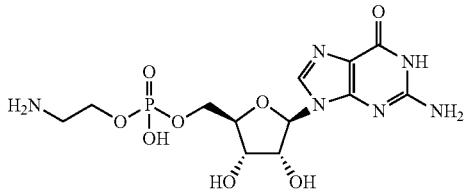

Step 1. tert-butyl(2-(((((3aR,4R,6R,6aR)-6-(2-amino-6-oxo-1H-purin-9(6H)-yl)-2,2-dimethyltetrahydrofuro[3,4-d][1,3]dioxol-4-yl)methoxy)(2-cyanoethoxy)phosphoryl)oxy)ethyl)carbamate

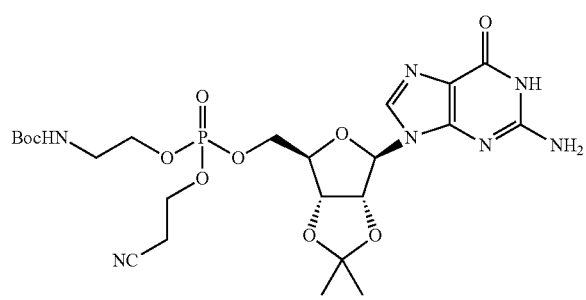 [SMILES: CC(C)(C)OC(=O)NCCOP(=O)(OCCC#N)OC[C@H]1O[C@@H](n2cnc3c(=O)[nH]c(N)nc32)[C@@H]2OC(C)(C)O[C@@H]21]

To a solution of tert-butyl(2-hydroxyethyl)carbamate (45.0 µL, 0.29 mmol) in DMF (2 mL) were added DIPEA (152.0 µL, 0.87 mmol) and 3-((chloro(diisopropylamino)phosphino)oxy)propanenitrile (97.3 µL, 0.44 mmol) at 0° C. The reaction mixture was warmed up to ambient temperature and stirred for 1 h. 2',3'-O-Isopropylideneguanosine (70.5 mg, 0.22 mmol) and 5-(ethylthio)-tetrazole (113.2 mg, 0.87 mmol) were added to the mixture that was stirred for another 1 h. Subsequently, m-CPBA (70%, 53.7 mg, 0.22 mmol) was added, and the mixture was stirred for 1 h. The mixture was diluted with DMSO (1 mL), and directly purified by preparative reverse-phase HPLC (methanol/water gradient) to provide tert-butyl(2-(((((3aR,4R,6R,6aR)-6-(2-amino-6-oxo-1H-purin-9(6H)-yl)-2,2-dimethyltetrahydrofuro[3,4-d][1,3]dioxol-4-yl)methoxy)(2-cyanoethoxy)phosphoryl)oxy)ethyl)carbamate. MS m/z: 600.34 (M+1).

Step 2. ((2R,3S,4R,5R)-5-(2-amino-6-oxo-1H-purin-9(6H)-yl)-3,4-dihydroxytetrahydrofuran-2-yl)methyl (2-aminoethyl)hydrogen phosphate

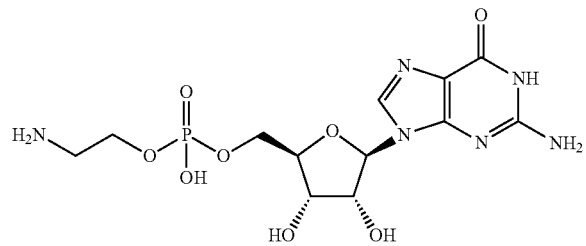 [SMILES: NCCOP(=O)(O)OC[C@H]1O[C@@H](n2cnc3c(=O)[nH]c(N)nc32)[C@H](O)[C@@H]1O]

tert-butyl(2-(((((3aR,4R,6R,6aR)-6-(2-amino-6-oxo-1H-purin-9(6H)-yl)-2,2-dimethyltetrahydrofuro[3,4-d][1,3]dioxol-4-yl)methoxy)(2-cyanoethoxy)phosphoryl)oxy)ethyl)carbamate (15.7 mg, 0.022 mmol) was dissolved in a 33% ethanol solution of methylamine (1 mL) at ambient temperature. The reaction mixture was stirred at ambient temperature for 20 min, and concentrated in vacuo. Then, the residue was suspended in dichloromethane (1 mL), water (1 mL), and trifluoroacetic acid (1 mL), and the mixture was stirred at ambient temperature for 1 h. It was directly purified by preparative reverse-phase HPLC (methanol/water gradient) to provide ((2R,3S,4R,5R)-5-(2-amino-6-oxo-1H-purin-9(6H)-yl)-3,4-dihydroxytetrahydrofuran-2-yl)methyl(2-aminoethyl)hydrogen phosphate. MS m/z: 407.47 (M+1).

Step 3. 2-acrylamidoethyl(((2R,3S,4R,5R)-5-(2-amino-6-oxo-1H-purin-9(6H)-yl)-3,4-dihydroxytetrahydrofuran-2-yl)methyl)hydrogen phosphate

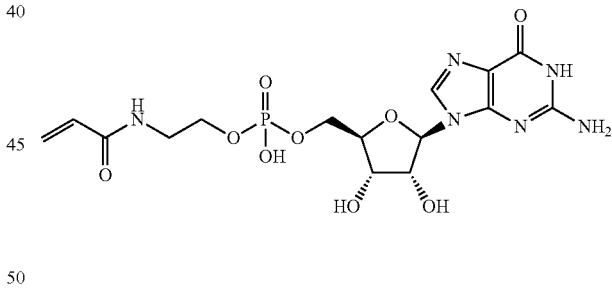

To a solution of ((2R,3S,4R,5R)-5-(2-amino-6-oxo-1H-purin-9(6H)-yl)-3,4-dihydroxytetrahydrofuran-2-yl)methyl (2-aminoethyl)hydrogen phosphate (25.0 mg, 0.05 mmol) in DMF (1 mL) were added DIPEA (43.3 µL, 0.25 mmol) and 2,5-dioxopyrrolidin-1-yl acrylate (12.6 mg, 0.75 mmol) at ambient temperature. The reaction mixture was stirred at ambient temperature for 1 h. It was diluted with water (10 mL) and washed with dichloromethane (10 mL, twice). The aqueous layer was concentrated in vacuo, diluted with water (1 mL), and directly purified by preparative reverse-phase HPLC (methanol/water gradient) to provide 2-acrylamidoethyl(((2R,3S,4R,5R)-5-(2-amino-6-oxo-1H-purin-9(6H)-yl)-3,4-dihydroxytetrahydrofuran-2-yl)methyl)hydrogen phosphate. MS m/z: 461.39 (M+1).

Example 2
(2-chloroacetamido)-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(hydroxy)phosphoryl)oxy)ethane
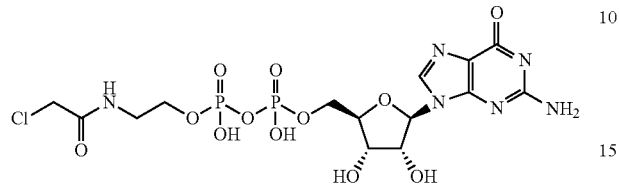
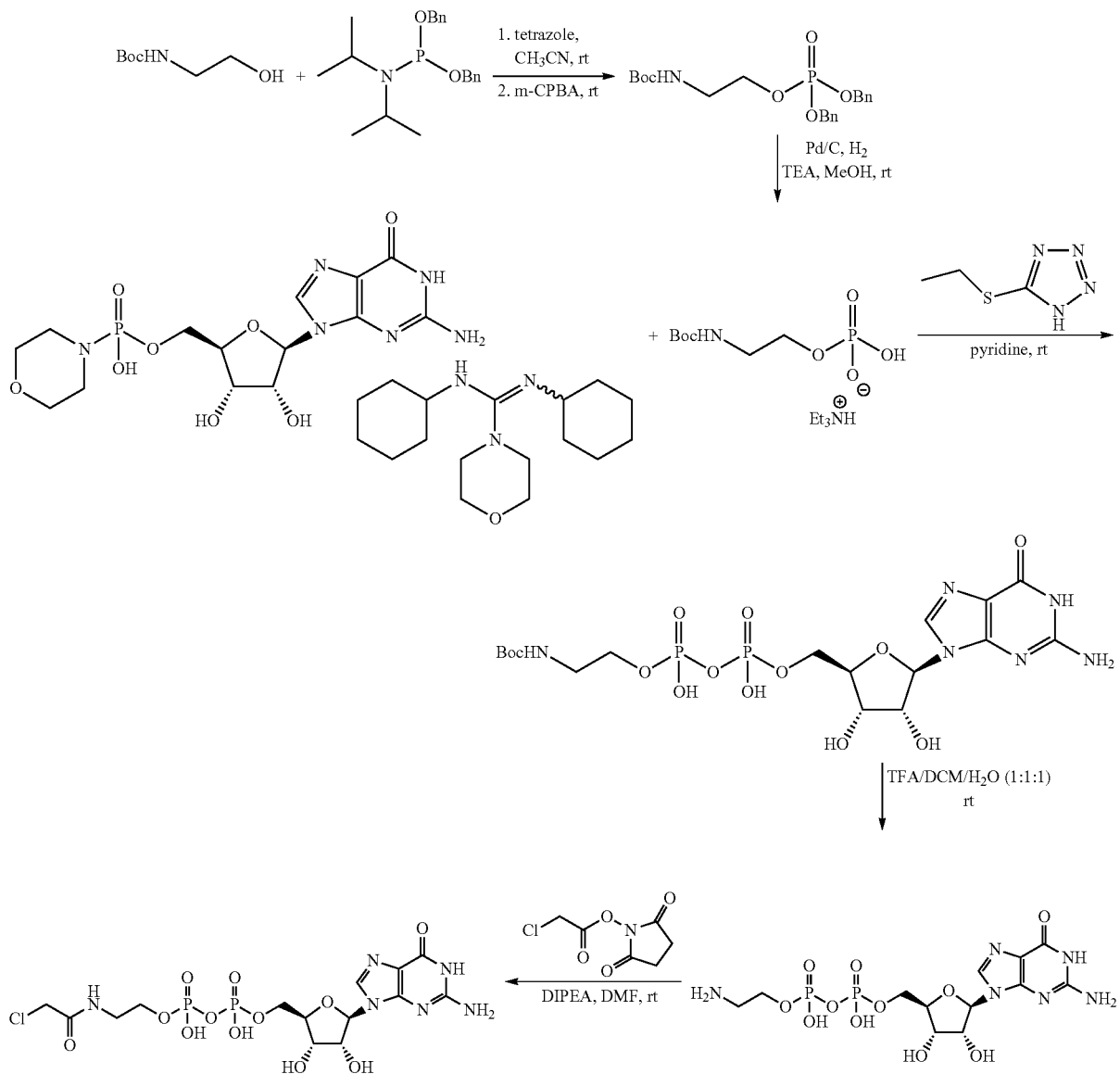

Step 1. tert-butyl(2-((bis(benzyloxy)phosphoryl)oxy)ethyl)carbamate

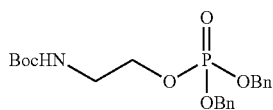 [SMILES: CC(C)(C)OC(=O)NCCOP(=O)(OCc1ccccc1)OCc1ccccc1]

To a mixture of tert-butyl(2-hydroxyethyl)carbamate (1.0 g, 6.2 mmol) and dibenzyl diisopropylphosphoramidite (4.2 mL, 12.4 mmol) was added a 0.45 M acetonitrile solution of tetrazole (42 mL, 18.6 mmol) at ambient temperature. The resulting solution was stirred at ambient temperature for 4 h. Then, at ambient temperature, m-CPBA (70%, 4.59 g, 18.6 mmol) was added to the reaction mixture that was stirred for further 1 h. The precipitate in the mixture was filtered through a pad of Celite®, and the filter cake was further washed with dichloromethane (100 mL). The combined filtrate was diluted with dichloromethane (50 mL) and washed with a saturated aqueous solution of sodium bicarbonate (100 mL, five times) and brine (100 mL). The organic layer was dried with sodium sulfate, filtered, and concentrated in vacuo. The residue was purified by flash column chromatography (4% methanol-dichloromethane) to provide tert-butyl (2-((bis(benzyloxy)phosphoryl)oxy)ethyl)carbamate (2.6 g, 68% over two steps) as a white solid.
$^1$H NMR 400 MHz (DMSO-$d_6$) δ 7.31-7.40 (m, 10H), 6.99 (m, 1H), 5.01 (d, J=7.2 Hz, 4H), 3.94 (q, J=6.0 Hz, 2H), 3.17 (q, J=5.4 Hz, 2H), 1.33 (s, 9H); MS m/z: 421.87 (M+1).

Step 2. 2-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(hydroxy)phosphoryl)oxy)ethylamine

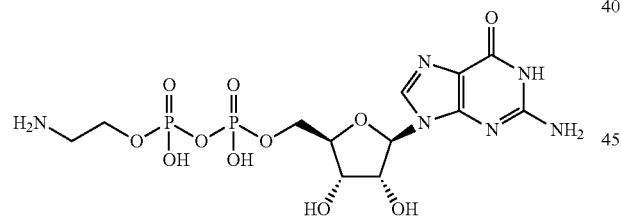

To a solution of tert-butyl(2-((bis(benzyloxy)phosphoryl)oxy)ethyl)carbamate (707.7 mg, 1.68 mmol) in methanol (35 mL) were added triethylamine (468.1 μL, 3.36 mmol) and Pd/C (500 mg) at ambient temperature. House vacuum was applied to the flask containing the suspension and hydrogen gas was back-filled to the flask. This process was repeated three times more. Under hydrogen atmosphere, the mixture was stirred at ambient temperature for 3 h. The mixture was diluted with methanol (50 mL) and filtered through a pad of Celite®. The filter cake was washed with additional methanol (50 mL), and the combined organic solution was concentrated in vacuo. A stock solution of crude 2-((tert-butoxycarbonyl)amino)ethyl phosphate-di-triethylamine salt was obtained by dissolving crude 2-((tert-butoxycarbonyl)amino)ethyl phosphate-di-triethylamine salt in pyridine (9 mL), and this solution was used in the next step without further purification. $^1$H NMR 600 MHz (DMSO-$d_6$) δ 7.00 (s, 1H), 3.62 (q, J=6.0 Hz, 2H), 3.03 (q, J=6.0 Hz, 2H), 2.90 (q, J=6.0 Hz, 6H), 1.36 (s, 9H), 1.12 (t, J=7.8 Hz, 9H); MS m/z: 242.25 (M+1).

To a suspension of Guanosine 5'-monophosphomorpholidate-4-morpholine-N,N'-dicyclohexylcarboxamidine salt (98.4 mg, 0.14 mmol) in pyridine (1 mL) were added a solution of 2-((tert-butoxycarbonyl)amino)ethyl phosphate-di-triethylamine salt (60.1 mg, 0.14 mmol) in pyridine (726 μL) followed by 5-(ethylthio)-tetrazole (52.9 mg, 0.41 mmol) at ambient temperature. The resulting mixture was stirred at ambient temperature for 2 h, and concentrated in vacuo. The residue was diluted with water (2 mL), and directly purified by preparative reverse-phase HPLC (methanol/water gradient) to provide tert-butyl(2-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(hydroxy)phosphoryl)oxy)ethyl)carbamate (50.3 mg, 53%). MS m/z: 587.29 (M+1).

tert-butyl(2-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(hydroxy)phosphoryl)oxy)ethyl)carbamate (50.3 mg, 0.072 mmol) was suspended in a mixture of dichloromethane (1 mL), water (1 mL), and trifluoroacetic acid (1 mL) at ambient temperature. The reaction mixture was stirred at ambient temperature for 1 h, and concentrated in vacuo. The residue was diluted with water (2 mL), and directly purified by preparative reverse-phase HPLC (methanol/water gradient) to provide 2-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(hydroxy)phosphoryl)-oxy)ethylamine (7.8 mg, 18%).
$^1$H NMR 600 MHz (D$_2$O) δ 9.04 (m, 1H), 6.00 (m, 1H), 4.62 (m, 1H), 4.44 (m, 1H), 4.35 (m, 1H), 4.29 (m, 1H), 4.19 (m, 1H), 4.16 (m, 2H), 3.24 (m, 2H); MS m/z: 487.12 (M+1).

Step 3. 2,5-dioxopyrrolidin-1-yl 2-chloroacetate

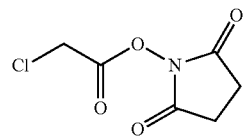

To a solution of N-hydroxysuccinimide (640.3 mg, 5.56 mmol) in chloroform (8.5 mL) was added triethylamine (861.6 μL, 6.18 mmol) 0° C. Then, α-chloroacetyl chloride was added dropwise over a 5 minute period and stirred for an additional 20 minutes at 0° C. The reaction mixture was washed with ice-cold water (15 mL) and brine (15 mL), concentrated to a volume of 1.7 mL in vacuo, then dried with sodium sulfate and filtered. To the resulting solution were added ethyl acetate (170 μL) and hexanes (1.2 mL), and the mixture was cooled down to 0° C. stirred for 2 h, and a white solid was precipitated. It was filtered and washed first with ice-cold 10 mL portion of hexanes/ethyl acetate (4:1), then with 10 mL hexanes/ethyl acetate (9:1), and finally with hexanes (10 mL, twice). The resulting white solid was dried under house vacuum to yield 2,5-dioxopyrrolidin-1-yl 2-chloroacetate (563.9 mg, 53%). $^1$H NMR 400 MHz (CDCl$_3$) δ 4.37 (s, 2H), 2.87 (s, 4H).

Step 4. (2-chloroacetamido)-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(hydroxy)phosphoryl)oxy)ethane

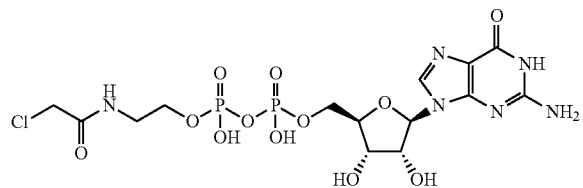 [SMILES: Nc1nc2c(ncn2[C@@H]2O[C@H](COP(=O)(O)OP(=O)(O)OCCNC(=O)CCl)[C@@H](O)[C@H]2O)c(=O)[nH]1]

To a solution of 2-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(hydroxy)phosphoryl)oxy)ethylamine (7.8 mg, 0.013 mmol) in DMF (1 mL) were added DIPEA (11.3 µL, 0.065 mmol) and 2,5-dioxopyrrolidin-1-yl 2-chloroacetate (5.0 mg, 0.026 mmol) at ambient temperature. The reaction mixture was stirred at ambient temperature for 1 h. It was diluted with water (10 mL) and washed with dichloromethane (10 mL). The aqueous layer was concentrated in vacuo, diluted with water (1 mL), and directly purified by preparative reverse-phase HPLC (methanol/water gradient) to provide (2-chloroacetamido)-(((((((2R,3S,4R,5R)-5-(2-amino-6-oxo-1H-purin-9(6H)-yl)-3,4-dihydroxytetrahydrofuran-2-yl)methoxy)(hydroxy) phosphoryl)oxy)(hydroxy)phosphoryl)-oxy)ethane (4.3 mg, 49%). $^1$H 400 MHz NMR (D$_2$O) δ 8.47 (s, 1H), 8.01 (s, 1H), 5.94 (d, J=6.6 Hz, 1H), 4.52 (dd, J=5.4, 3.0 Hz, 1H), 4.34-4.36 (m, 1H), 4.20-4.22 (m, 2H), 4.11 (s, 2H), 4.00-4.03 (m, 2H), 3.43-3.46 (m, 2H); MS m/z: 563.07 (M+1).

Example 3

(2S)-2-propylpentyl 2-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(2-(2-chloroacetamido)ethoxy)phosphoryl)amino)propanoate

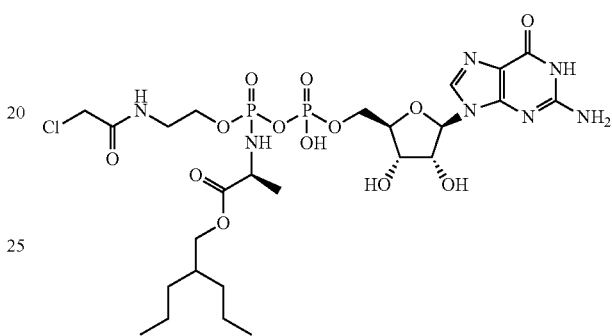

Scheme 3.

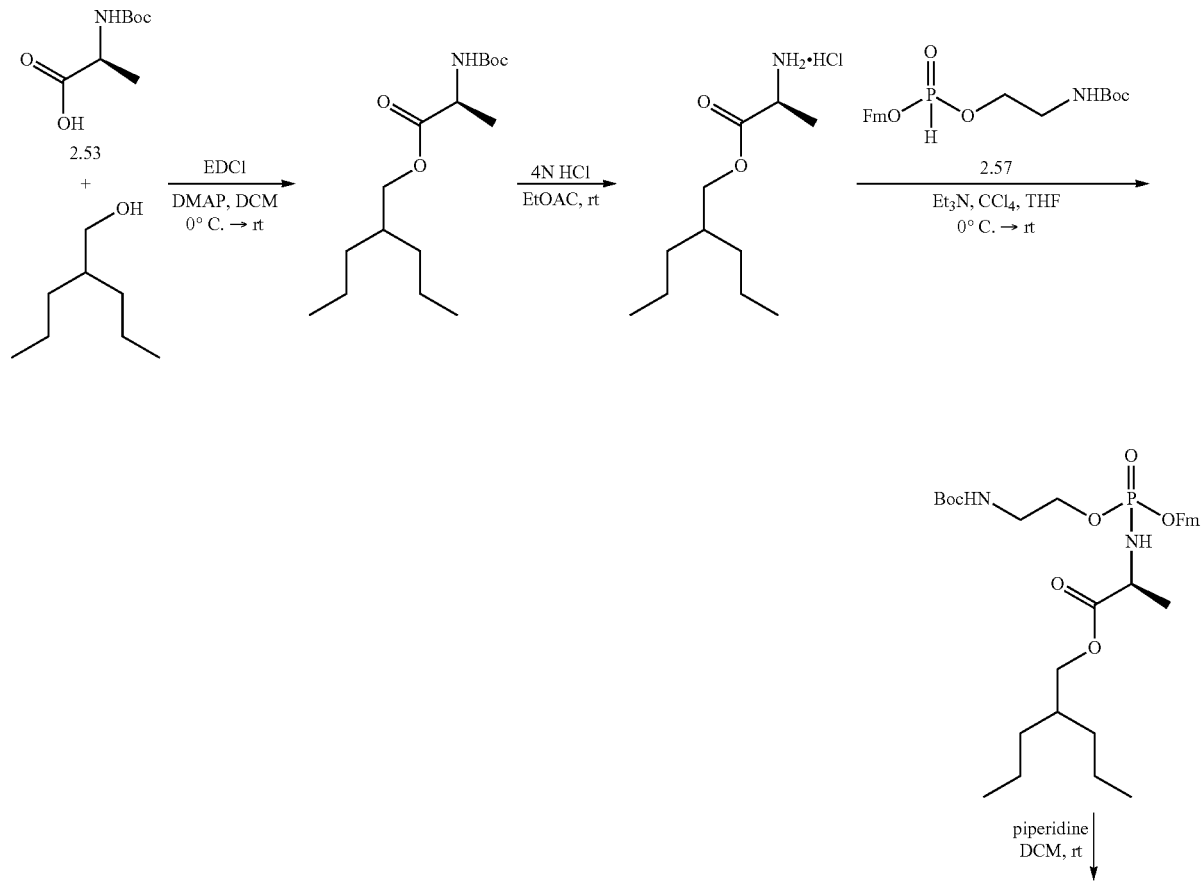

-continued
135
136
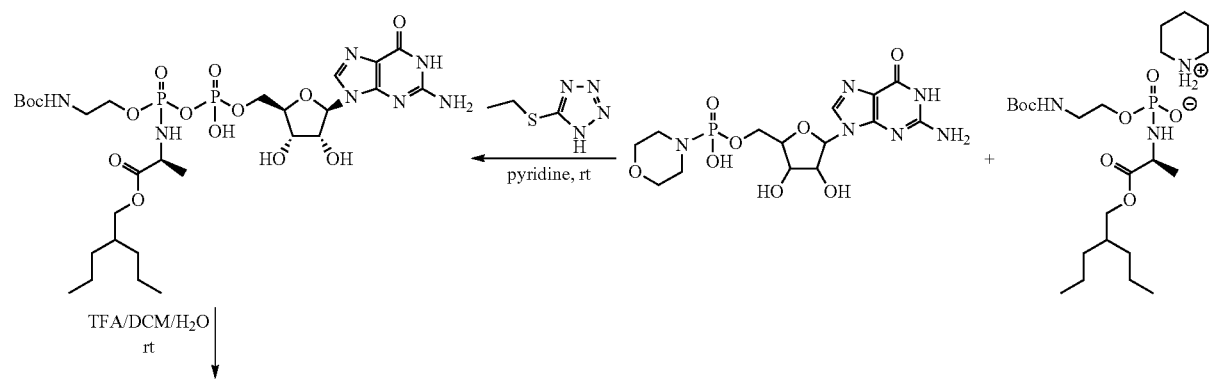
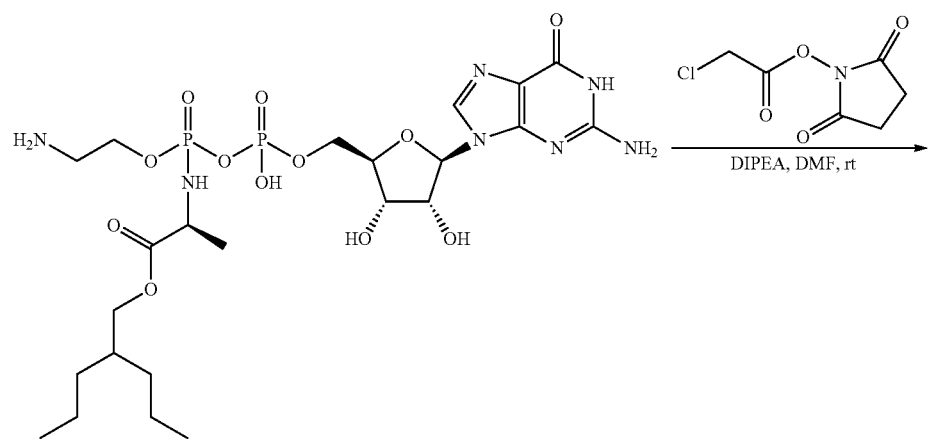
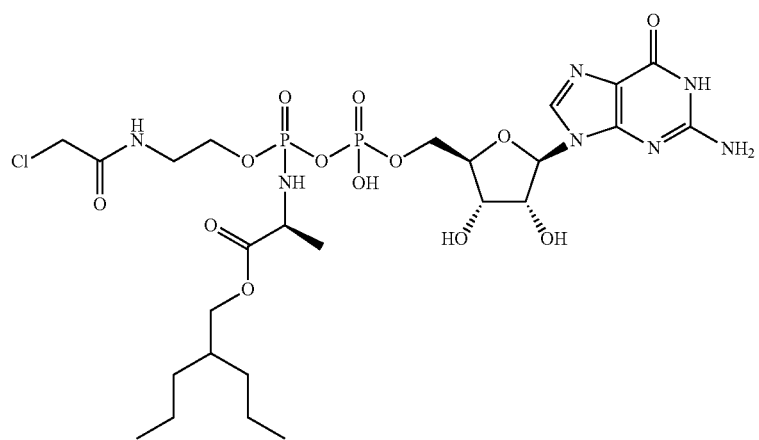 [SMILES: CCCC(CCC)COC(=O)[C@H](C)NP(=O)(OCCNC(=O)CCl)OP(=O)(O)OC[C@H]1O[C@@H](n2cnc3c(=O)[nH]c(N)nc32)[C@H](O)[C@@H]1O]

Step 1. (2S)-2-propylpentyl 2-((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(2-aminoethoxy)phosphoryl)amino)propanoate

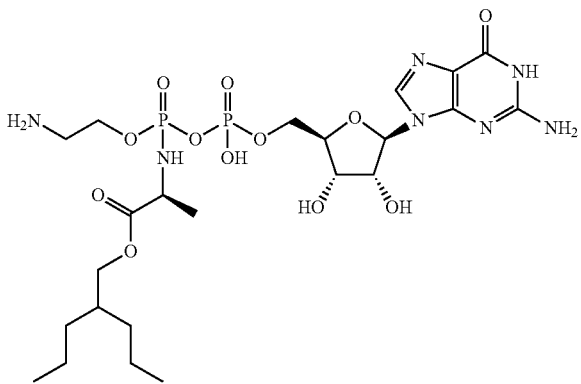 [SMILES: CCCC(CCC)COC(=O)[C@H](C)NP(=O)(OCCN)OP(=O)(O)OC[C@H]1O[C@@H](n2cnc3c(=O)[nH]c(N)nc32)[C@H](O)[C@@H]1O]

To a solution of (S)-2-((tert-butoxycarbonyl)amino)propanoic acid (1.14 g, 6.0 mmol) in dichloromethane (14.2 mL) were added 2-propylpentan-1-ol (941.4 µL, 6.0 mmol), DMAP (73.3 mg, 0.6 mmol), and EDCI (1.27 g, 6.6 mmol) at ambient temperature. The resulting dark yellow solution was stirred at ambient temperature for 14 h. It was diluted with ethyl acetate (100 mL), and washed with a saturated aqueous solution of sodium bicarbonate (100 mL, three times) and brine (100 mL, twice). The organic layer was dried with sodium sulfate, filtered, and concentrated in vacuo. The residue containing crude (S)-2-propylpentyl 2-((tert-butoxycarbonyl)amino)propanoate was used in the next step without further purification. MS m/z: 302.00 (M+1).

To a solution of crude (S)-2-propylpentyl 2-((tert-butoxycarbonyl)amino)propanoate in ethyl acetate (10 mL) was added a 4 N dioxane solution of hydrochloric acid (10.5 mL, 42 mmol) at ambient temperature. The yellow solution was stirred at ambient temperature for 2 h, and concentrated in vacuo. The residue containing crude (S)-2-propylpentyl 2-aminopropanoate was used in the next step without further purification. MS m/z: 201.94 (M+1).

To a solution of diphenylphosphine oxide (1.15 mL, 6.0 mmol) in pyridine (13 mL) was added a solution of 9-fluorenemethanol (981.2 mg, 5.0 mmol) in pyridine (13 mL) at 5° C. The reaction mixture was stirred at 5° C. for 30 min. Then, a solution of tert-butyl (2-hydroxyethyl)carbamate (1.08 mL, 7.0 mmol) in pyridine (13 mL) was added to the mixture that was heated to 40° C. and stirred for 1 h. The mixture was concentrated in vacuo. The residue containing crude (9H-fluoren-9-yl)methyl(2-(tert-butoxycarbonylamino)ethyl)phosphonate was used in the next step without further purification. MS m/z: 403.83 (M+1).

To a solution of crude (S)-2-propylpentyl 2-aminopropanoate in THF (25 mL) were added triethylamine (1.39 mL, 10 mmol) and carbon tetrachloride (2.5 mL) at 5° C. To this mixture was added crude (9H-fluoren-9-yl)methyl(2-(tert-butoxycarbonylamino)ethyl)phosphonate in THF (10 mL) at 5° C., and the resulting mixture was warmed up to ambient temperature and stirred for 3 h. It was concentrated in vacuo, and the residue was diluted with dichloromethane (200 mL), and washed with 0.1 N hydrochloric acid (150 mL, three times). The organic layer was dried with sodium sulfate, filtered, and concentrated in vacuo. The residue was purified by flash column chromatography (5% methanol-dichloromethane) to provide (((2-((tert-butoxycarbonyl)amino)ethoxy)((((S)-1-oxo-1-((2-propylpentyl)oxy)propan-2-yl)amino)phosphoryl)oxy)fermium. MS m/z: 603.21 (M+1).

To a solution of (((2-((tert-butoxycarbonyl)amino)ethoxy)((((S)-1-oxo-1-((2-propylpentyl)oxy)propan-2-yl)amino)phosphoryl)oxy)fermium (1.0 mmol) in dichloromethane (5 mL) was added piperidine (1 mL) at ambient temperature. The reaction mixture was stirred at ambient temperature for 30 min, and concentrated in vacuo. The residue was diluted with water (30 mL) and white precipitate was formed. The precipitate was filtered through a filter paper by gravity. Dichloromethane (30 mL) was added to the filtrate, and after a few shake two layers were formed and separated. The organic layer was concentrated in vacuo. The residue containing crude (S)-2-((tert-butoxycarbonyl)amino)ethyl(1-oxo-1-((2-propylpentyl)oxy)propan-2-yl)phosphoramidate-piperidine salt was used directly in the next step without further purification. MS m/z: 425.40 (M+1).

To a suspension of Guanosine 5'-monophosphomorpholidate-4-morpholine-N,N'-dicyclohexylcarboxamidine salt (93.6 mg, 0.13 mmol) in pyridine (1 mL) were added a solution of (S)-2-((tert-butoxycarbonyl)amino)ethyl(1-oxo-1-((2-propylpentyl)oxy)propan-2-yl)phosphoramidate-piperidine salt (85.4 mg, 0.17 mmol) in pyridine (1 mL) followed by 5-(ethylthio)-tetrazole (50.4 mg, 0.39 mmol) at ambient temperature. The resulting mixture was stirred at ambient temperature for 3 h, and concentrated in vacuo. The residue containing crude (2S)-2-propylpentyl 2-((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(2-((tert-butoxycarbonyl)amino)ethoxy)phosphoryl)amino)propanoate was suspended in a mixture of dichloromethane (1 mL), water (1 mL), and trifluoroacetic acid (2 mL) at ambient temperature. The reaction mixture was stirred at ambient temperature for 1 h, and concentrated in vacuo. The residue was diluted with water (1 mL) and purified by preparative reverse-phase HPLC (methanol/water gradient) to provide (2S)-2-propylpentyl 2-((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(2-aminoethoxy)phosphoryl)amino)propanoate. MS m/z: 670.46 (M+1).

Step 2. (2S)-2-propylpentyl 2-((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(2-(2-chloroacetamido)ethoxy)phosphoryl)amino)propanoate

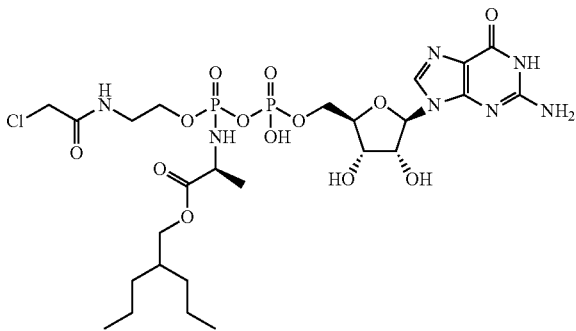 [SMILES: CCCC(CCC)COC(=O)[C@H](C)NP(=O)(OCCNC(=O)CCl)OP(=O)(O)OC[C@H]1O[C@@H](n2cnc3c(=O)[nH]c(N)nc32)[C@H](O)[C@@H]1O]

To a solution of (2S)-2-propylpentyl 2-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(2-aminoethoxy)phosphoryl)amino)propanoate (15.0 mg, 0.019 mmol) in DMF (1 mL) were added DIPEA (16.7 µL, 0.096 mmol) and 2.17 (7.3 mg, 0.038 mmol) at ambient temperature. The reaction mixture was stirred at ambient temperature for 30 min. It was diluted with water (10 mL) and washed with dichloromethane (10 mL). The aqueous layer was concentrated in vacuo, diluted with water (1 mL), and directly purified by preparative reverse-phase HPLC (methanol/water gradient) to provide (2S)-2-propylpentyl 2-(((((((2R,3S,4R,5R)-5-(2-amino-6-oxo-1H-purin-9(6H)-yl)-3,4-dihydroxytetrahydrofuran-2-yl)methoxy)(hydroxy)phosphoryl)oxy)(2-(2-chloroacetamido)ethoxy)phosphoryl)amino)-propanoate. MS m/z: 746.41 (M+1).

The compounds produced by using the corresponding starting compounds according to methods similar to that described in Example 1, 2 and 3 are shown in Table 1.

TABLE 1

Additional Compounds Prepared Based on Example 1, 2 and 3:

| Compound Code | Structure | NMR, Retention time and/or Mass m/z: (M + 1). |
|---|---|---|
| Example 4 | 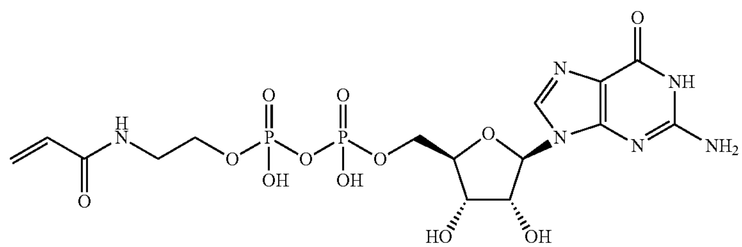 [SMILES: C=CC(=O)NCCOP(=O)(O)OP(=O)(O)OC[C@H]1O[C@@H](n2cnc3c(=O)[nH]c(N)nc32)[C@H](O)[C@@H]1O] | 541.12 (M + 1) |
| Example 5 | 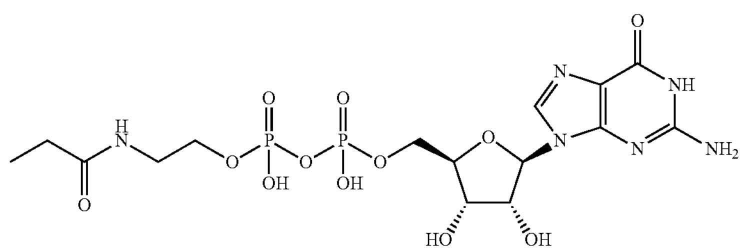 [SMILES: CCC(=O)NCCOP(=O)(O)OP(=O)(O)OC[C@H]1O[C@@H](n2cnc3c(=O)[nH]c(N)nc32)[C@H](O)[C@@H]1O] | 543.09 (M + 1) |
| Example 6 | 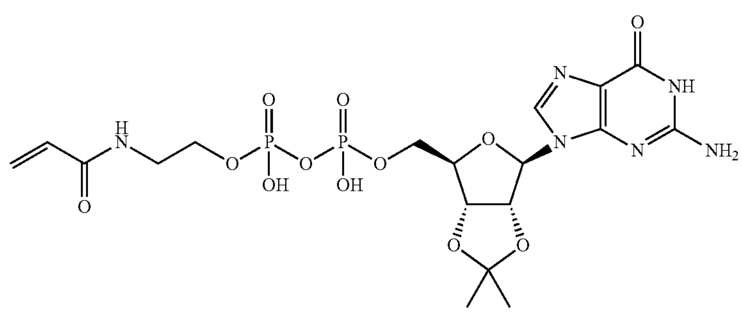 [SMILES: C=CC(=O)NCCOP(=O)(O)OP(=O)(O)OC[C@H]1O[C@@H](n2cnc3c(=O)[nH]c(N)nc32)[C@@H]2OC(C)(C)O[C@@H]21] | 581.10 (M + 1) |
| Example 7 | 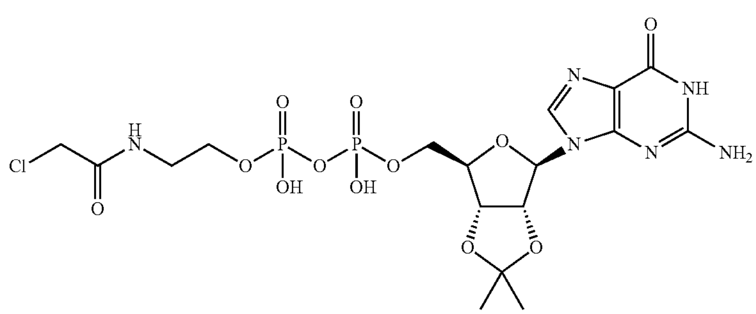 [SMILES: CC1(C)O[C@@H]2[C@H](O1)[C@@H](COP(=O)(O)OP(=O)(O)OCCNC(=O)CCl)O[C@H]2n1cnc2c(=O)[nH]c(N)nc21] | 603.07 (M + 1) |

TABLE 1-continued

Additional Compounds Prepared Based on Example 1, 2 and 3:

| Compound Code | Structure | NMR, Retention time and/or Mass m/z: (M + 1). |
|---|---|---|
| Example 8 | 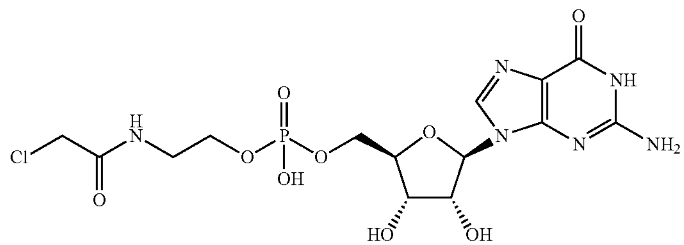 [SMILES: Nc1nc2c(ncn2[C@@H]2O[C@H](COP(=O)(O)OCCNC(=O)CCl)[C@@H](O)[C@H]2O)c(=O)[nH]1] | 483.05 (M + 1) |
| Example 9 | 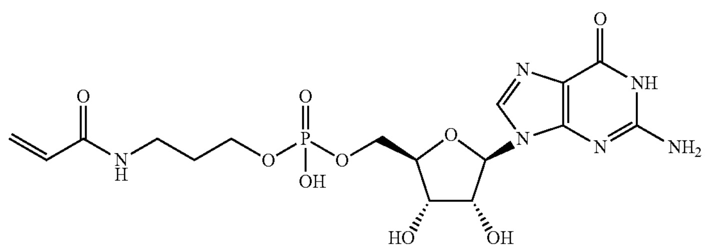 [SMILES: C=CC(=O)NCCCOP(=O)(O)OC[C@H]1O[C@@H](n2cnc3c(=O)[nH]c(N)nc32)[C@H](O)[C@@H]1O] | 475.10 (M + 1) |
| Example 10 | 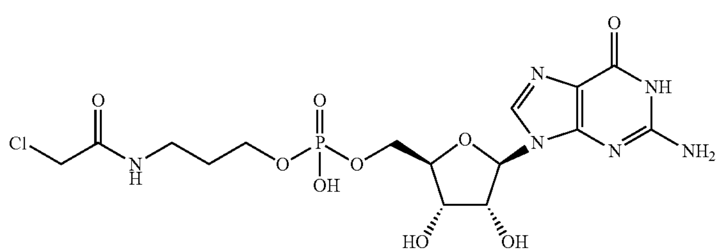 [SMILES: Nc1nc2c(ncn2[C@@H]2O[C@H](COP(=O)(O)OCCCNC(=O)CCl)[C@@H](O)[C@H]2O)c(=O)[nH]1] | 497.11 (M + 1) |
| Example 11 | 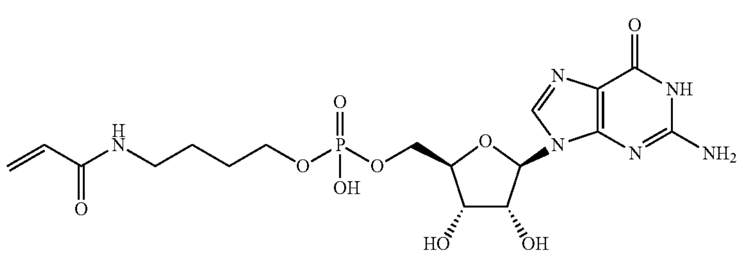 [SMILES: C=CC(=O)NCCCCOP(=O)(O)OC[C@H]1O[C@@H](n2cnc3c(=O)[nH]c(N)nc32)[C@H](O)[C@@H]1O] | 489.07 (M + 1) |
| Example 12 | 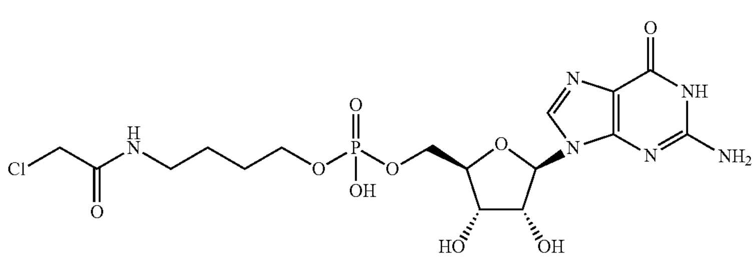 [SMILES: Nc1nc2c(ncn2[C@@H]2O[C@H](COP(=O)(O)OCCCCNC(=O)CCl)[C@@H](O)[C@H]2O)c(=O)[nH]1] | 510.02 (M + 1) |

TABLE 1-continued

Additional Compounds Prepared Based on Example 1, 2 and 3:

| Compound Code | Structure | NMR, Retention time and/or Mass m/z: (M + 1). |
|---|---|---|
| Example 13 | 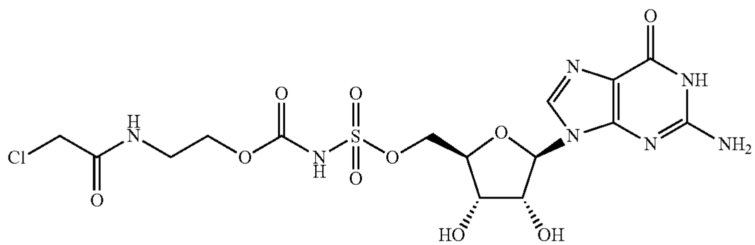 [SMILES: Nc1nc2c(ncn2[C@@H]2O[C@H](COS(=O)(=O)NC(=O)OCCNC(=O)CCl)[C@@H](O)[C@H]2O)c(=O)[nH]1] | 526.11 (M + 1) |
| Example 14 | 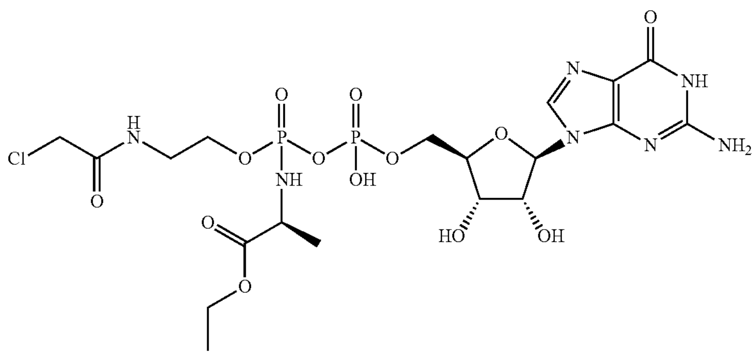 [SMILES: CCOC(=O)[C@H](C)NP(=O)(OCCNC(=O)CCl)OP(=O)(O)OC[C@H]1O[C@@H](n2cnc3c(=O)[nH]c(N)nc32)[C@H](O)[C@@H]1O] | 662.20 (M + 1) |
| Example 15 | 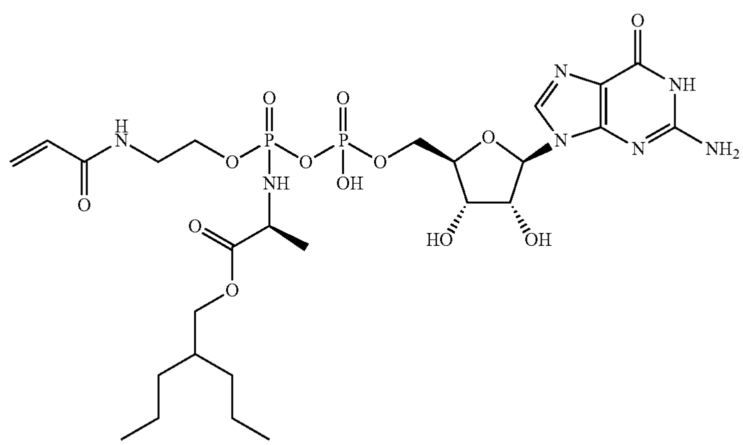 [SMILES: C=CC(=O)NCCOP(=O)(N[C@@H](C)C(=O)OCC(CCC)CCC)OP(=O)(O)OC[C@H]1O[C@@H](n2cnc3c(=O)[nH]c(N)nc32)[C@H](O)[C@@H]1O] | 724.25 (M + 1) |
| Example 16 | 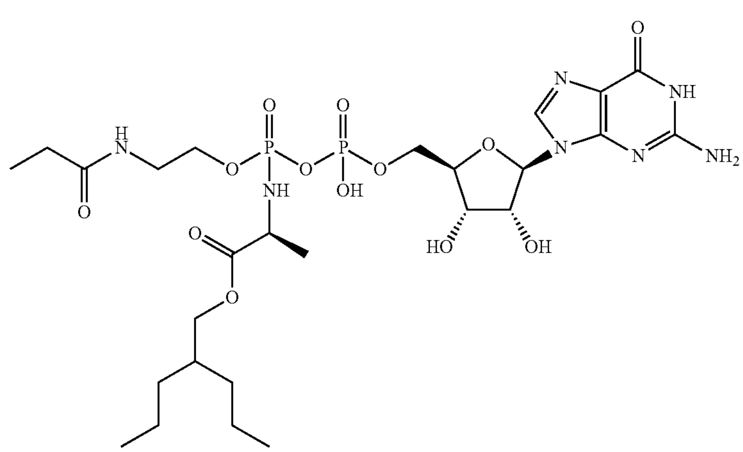 [SMILES: CCCC(CCC)COC(=O)[C@H](C)NP(=O)(OCCNC(=O)CC)OP(=O)(O)OC[C@H]1O[C@@H](n2cnc3c(=O)[nH]c(N)nc32)[C@H](O)[C@@H]1O] | 726.15 (M + 1) |

TABLE 1-continued
Additional Compounds Prepared Based on Example 1, 2 and 3:
| Compound Code | Structure | NMR, Retention time and/or Mass m/z: (M + 1). |
|---|---|---|
| Example 17 | 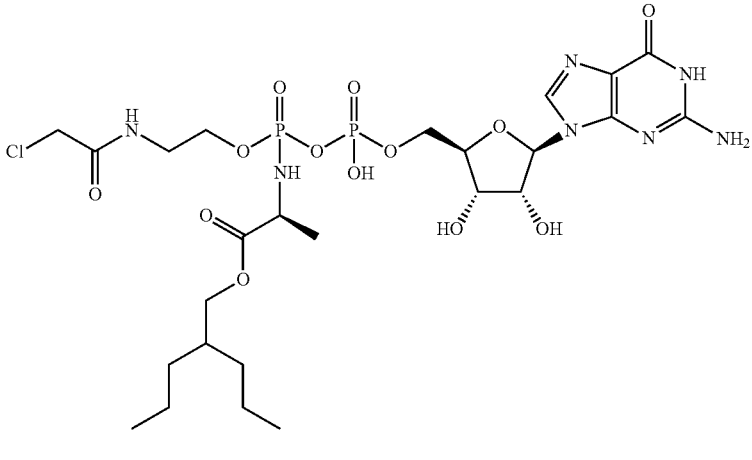 | 718.17 (M + 1) |
| Example 18 | 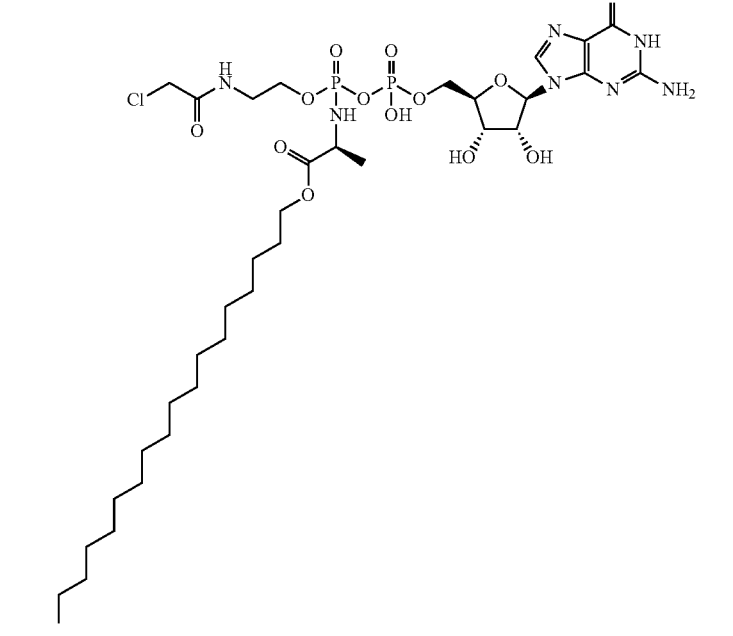 | 858.27 (M + 1) |
| Example 19 | 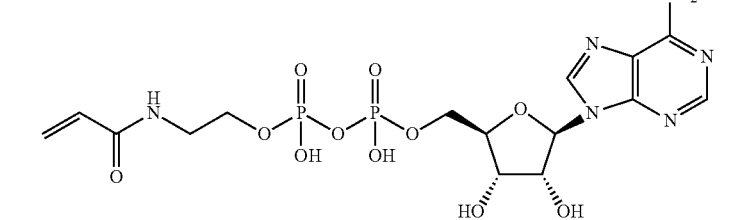 | 1.43 (B), 525.08 (M + 1) |

TABLE 1-continued
Additional Compounds Prepared Based on Example 1, 2 and 3:
| Compound Code | Structure | NMR, Retention time and/or Mass m/z: (M + 1). |
|---|---|---|
| Example 20 | 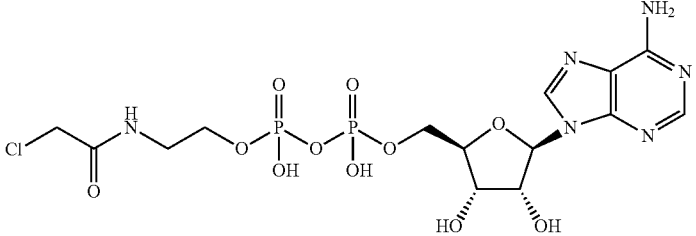 [SMILES: Nc1ncnc2c1ncn2[C@@H]1O[C@H](COP(=O)(O)OP(=O)(O)OCCNC(=O)CCl)[C@@H](O)[C@H]1O] | 1.65 (B), 547.20 (M + 1) |
Example 21
N-(2-((2-(((((2R,3S,4R,5R)-5-(2-amino-6-oxo-1H-purin-9(6H)-yl)-3,4-dihydroxytetrahydrofuran-2-yl)methyl)amino)-3,4-dioxocyclobut-1-en-1-yl)amino)ethyl)acrylamide
20
25
Scheme 4.
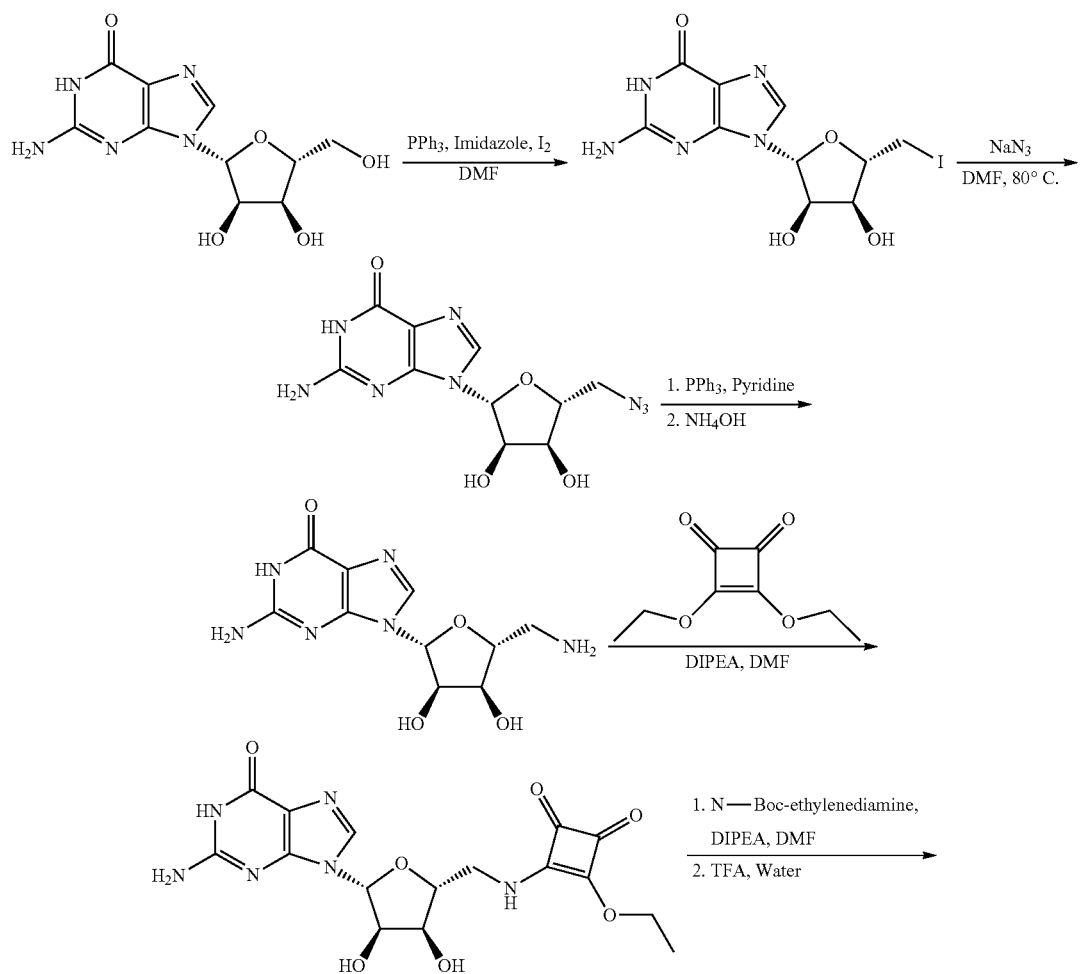

-continued

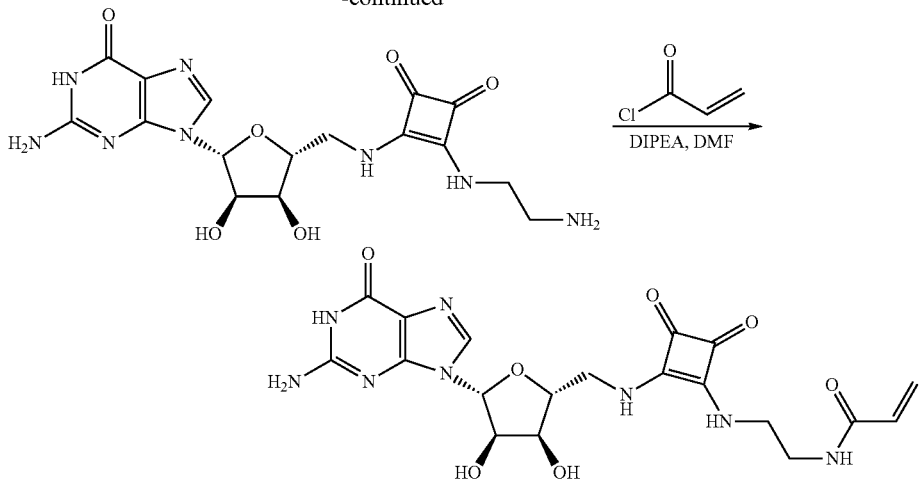

Step 1. 2-Amino-9-((2R,3R,4S,5S)-3,4-dihydroxy-5-(iodomethyl)-tetrahydrofuran-2-yl)-1H-purin-6(9H)-one

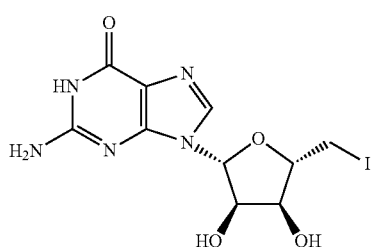 [SMILES: Nc1nc2c(ncn2[C@@H]2O[C@H](CI)[C@@H](O)[C@H]2O)c(=O)[nH]1]

To a suspension of guanosine (1.0 g, 3.54 mmol), triphenylphosphine (3.06 g, 11.67 mmol) and imidazole (1.59 g, 24.33 mmol) in anhydrous DMF (135 mL), iodine (2.85 g, 11.22 mmol) was added portionwise while vigorous stirring over a period of five minutes at 0° C. The orange solution was cooled down to room temperature and further stirred for 4 hours. The reaction mixture was poured into the mixture of DCM (130 mL) and water (40 mL). The white precipitate was filtered, washed with DCM (10 mL) and dried through nitrogen gas flow to give 2-Amino-9-((2R,3R,4S,5S)-3,4-dihydroxy-5-(iodomethyl)-tetrahydrofuran-2-yl)-1H-purin-6(9H)-one as a white powder in 68% yield (940 mg). RT: 2.38 (Method: A); $^1$H NMR 400 MHz (DMSO-$d_6$) δ 10.64 (s, 1H), 7.90 (s, 1H), 7.57 (s, 1H), 6.47 (s, 2H), 5.70 (d, J=6 Hz, 1H), 5.52 (br, 1H), 4.61 (t, J=5.6 Hz, 1H), 4.04 (m, 1H), 3.92 (m, 1H), 3.56 (m, 1H), 3.40 (m, 1H); Mass m/z: 394.10 (M+1).

Step 2. 2-amino-9-((2R,3R,4S,5R)-5-(azidomethyl)-3,4-dihydroxytetrahydrofuran-2-yl)-1H-purin-6(9H)-one

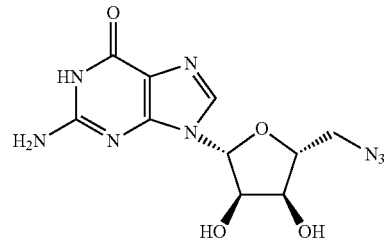 [SMILES: [N-]=[N+]=NC[C@H]1O[C@@H](n2cnc3c(=O)[nH]c(N)nc32)[C@H](O)[C@@H]1O]

To a suspension of 2-Amino-9-((2R,3R,4S,5S)-3,4-dihydroxy-5-(iodomethyl)-tetrahydrofuran-2-yl)-1H-purin-6(9H)-one (740 g, 1.90 mmol) in anhydrous DMF (5 mL) was added sodium azide (250 mg, 3.80 mmol). The reaction mixture was stirred at 80° C. for 22 hours. The solvent was removed in vacuo and added water (10 mL). The solid residue was sonicated for 15 minutes, filtered, washed with water and dried through nitrogen gas flow. The crude product was rinsed EtOH (2.5 mL) and diethylether (2.5 mL) and dried through nitrogen gas flow to give 2-amino-9-((2R,3R,4S,5R)-5-(azidomethyl)-3,4-dihydroxytetrahydrofuran-2-yl)-1H-purin-6(9H)-one as a brown powder in 72% yield (420 mg). RT: 1.86 (Method: A), Mass m/z: 309.23 (M+1).

Step 3. 2-Amino-9-((2R,3R,4S,5R)-3,4-dihydroxy-5-(aminomethyl)-tetrahydrofuran-2-yl)-1H-purin-6(9H)-one

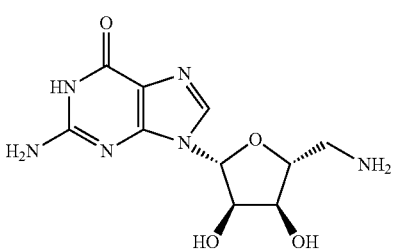 [SMILES: NC[C@H]1O[C@@H](n2cnc3c(=O)[nH]c(N)nc32)[C@H](O)[C@@H]1O]

To a solution of 2-amino-9-((2R,3R,4S,5R)-5-(azidomethyl)-3,4-dihydroxytetrahydrofuran-2-yl)-1H-purin-6(9H)-one (400 mg, 1.30 mmol) in anhydrous pyridine (8 ml) was added Triphenylphosphine (680 mg, 2.60 mmol). The reaction mixture was stirred at room temperature for 5 hours, after which water (8 mL) and aqueous ammonia (35%, 2.6 mL) were added. The reaction mixture was stirred for another 2 days. The solvents were removed in vacuo and was added ethylacetate (34 mL). The solid residue was sonicated for 15 minutes, filtered, washed with cold ethylacetate and dried through nitrogen gas flow. The crude product was rinsed cold ethylacetate-methanol and water and dried through nitrogen gas flow to give 2-Amino-9-((2R,3R,4S,5R)-3,4-dihydroxy-5-(aminomethyl)-tetrahydrofuran-2-yl)-1H-purin-6(9H)-one as a white powder in 65% yield (240 mg).

Step 4. 3-((((2R,3S,4R,5R)-5-(2-amino-6-oxo-1H-purin-9(6H)-yl)-3,4-dihydroxytetrahydrofuran-2-yl)methyl)amino)-4-ethoxycyclobut-3-ene-1,2-dione

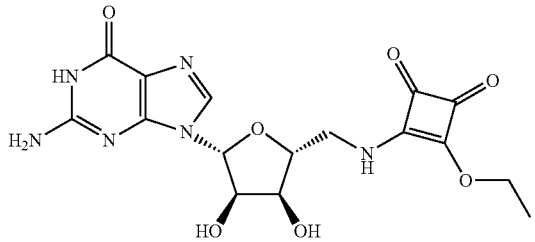 [SMILES: CCOc1c(NC[C@H]2O[C@@H](n3cnc4c(=O)[nH]c(N)nc43)[C@H](O)[C@@H]2O)c(=O)c1=O]

To a solution of 2-Amino-9-((2R,3R,4S,5R)-3,4-dihydroxy-5-(aminomethyl)-tetrahydrofuran-2-yl)-1H-purin-6(9H)-one as (200 mg, 0.71 mmol) in anhydrous DMF (10 mL) were added DIPEA (0.25 mL, 1.42 mmol) and 3,4-diethoxycyclobut-3-ene-1,2-dione (132 mg, 0.78 mmol). The reaction mixture was stirred at room temperature for 18 hours. The solvent was removed in vacuo and was added acetone (5 mL). The solid residue was sonicated for 15 minutes, filtered, washed with cold acetone and dried through nitrogen gas flow to give 3-(4(2R,3S,4R,5R)-5-(2-amino-6-oxo-1H-purin-9(6H)-yl)-3,4-dihydroxytetrahydrofuran-2-yl)methyl)amino)-4-ethoxycyclobut-3-ene-1,2-dione as a light yellow powder in 62% yield (180 mg). RT: 2.05 (Method: A), Mass m/z: 407.27 (M+1).

Step 5. 3-((((2R,3S,4R,5R)-5-(2-amino-6-oxo-1H-purin-9(6H)-yl)-3,4-dihydroxytetrahydrofuran-2-yl)methyl)amino)-4-((2-aminoethyl)amino)cyclobut-3-ene-1,2-dione

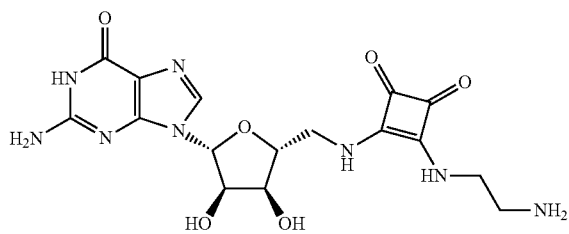 [SMILES: NCCNc1c(NC[C@H]2O[C@@H](n3cnc4c(=O)[nH]c(N)nc43)[C@H](O)[C@@H]2O)c(=O)c1=O]

To a solution of 3-((((2R,3S,4R,5R)-5-(2-amino-6-oxo-1H-purin-9(6H)-yl)-3,4-dihydroxytetrahydrofuran-2-yl)methyl)amino)-4-ethoxycyclobut-3-ene-1,2-dione (70 mg, 0.17 mmol) in anhydrous DMF (1 mL) were added DIEPA (44 µL, 0.26 mmol) and tert-butyl(2-aminoethyl)carbamate (30 mg, 0.19 mmol). The reaction mixture was stirred for 4 hours at room temperature. The reaction mixture was diluted with DMSO (1 mL). The solution was directly purified by preparative reverse-phase HPLC (methanol/water gradient). The solvent was removed in vacuo. To a concentrated mixture were added water (1 mL) and trifluoroacetic acid (0.2 mL). The reaction mixture was stirred for 1 hour. The trifluoroacetic acid was removed in vacuo and the water solution was freeze-dried to give 3-((((2R,3S,4R,5R)-5-(2-amino-6-oxo-1H-purin-9(6H)-yl)-3,4-dihydroxytetrahydrofuran-2-yl)methyl)amino)-4-((2-aminoethyl)amino)cyclobut-3-ene-1,2-dione trifluoroacetic acid salt as a white solid in 94% yield (82 mg). RT: 0.85 (Method: A), Mass m/z: 421.25 (M+1).

Step 6. N-(2-((2-((((2R,3S,4R,5R)-5-(2-amino-6-oxo-1H-purin-9(6H)-yl)-3,4-dihydroxytetrahydrofuran-2-yl)methyl)amino)-3,4-dioxocyclobut-1-en-1-yl)amino)ethyl)acrylamide

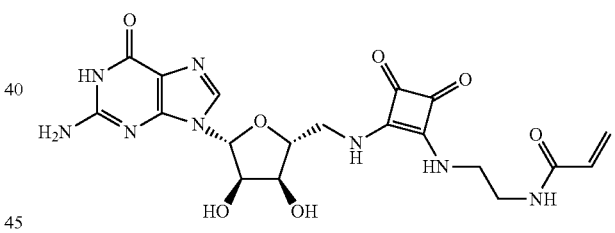

To a 3-(4(2R,3S,4R,5R)-5-(2-amino-6-oxo-1H-purin-9(6H)-yl)-3,4-dihydroxytetrahydrofuran-2-yl)methyl)amino)-4-((2-aminoethyl)amino)cyclobut-3-ene-1,2-dione trifluoroacetic acid salt (40 mg, 0.08 mmol) in anhydrous DMF (1 mL) were added DIPEA (42 µL, 0.24 mmol) and acryloyl chloride (7.3 µL, 0.09 mmol) at 0° C. for 2 hours. The reaction mixture was diluted with DMSO (1 mL) and was directly purified by preparative reverse-phase HPLC (methanol/water gradient). The methanol was removed in vacuo and the water solution was freeze-dried to give N-(2-((2-((((2R,3S,4R,5R)-5-(2-amino-6-oxo-1H-purin-9(6H)-yl)-3,4-dihydroxytetrahydrofuran-2-yl)methyl)amino)-3,4-dioxocyclobut-1-en-1-yl)amino)ethyl)acrylamide trifluoroacetic acid salt as a white solid in 88% yield (38 mg). RT: 1.83 (Method: A), Mass m/z: 475.25 (M+1).

Example 31
(E)-N-(2-((2-((((2R,3S,4R,5R)-5-(2-amino-6-oxo-1,6-dihydro-9H-purin-9-yl)-3,4-dihydroxytetrahydrofuran-2-yl)methyl)amino)-3,4-dioxocyclobut-1-en-1-yl)amino)ethyl)-4-(4-((4-chloro-5-iodo-2-methoxyphenyl)glycyl)piperazin-1-yl)but-2-enamide
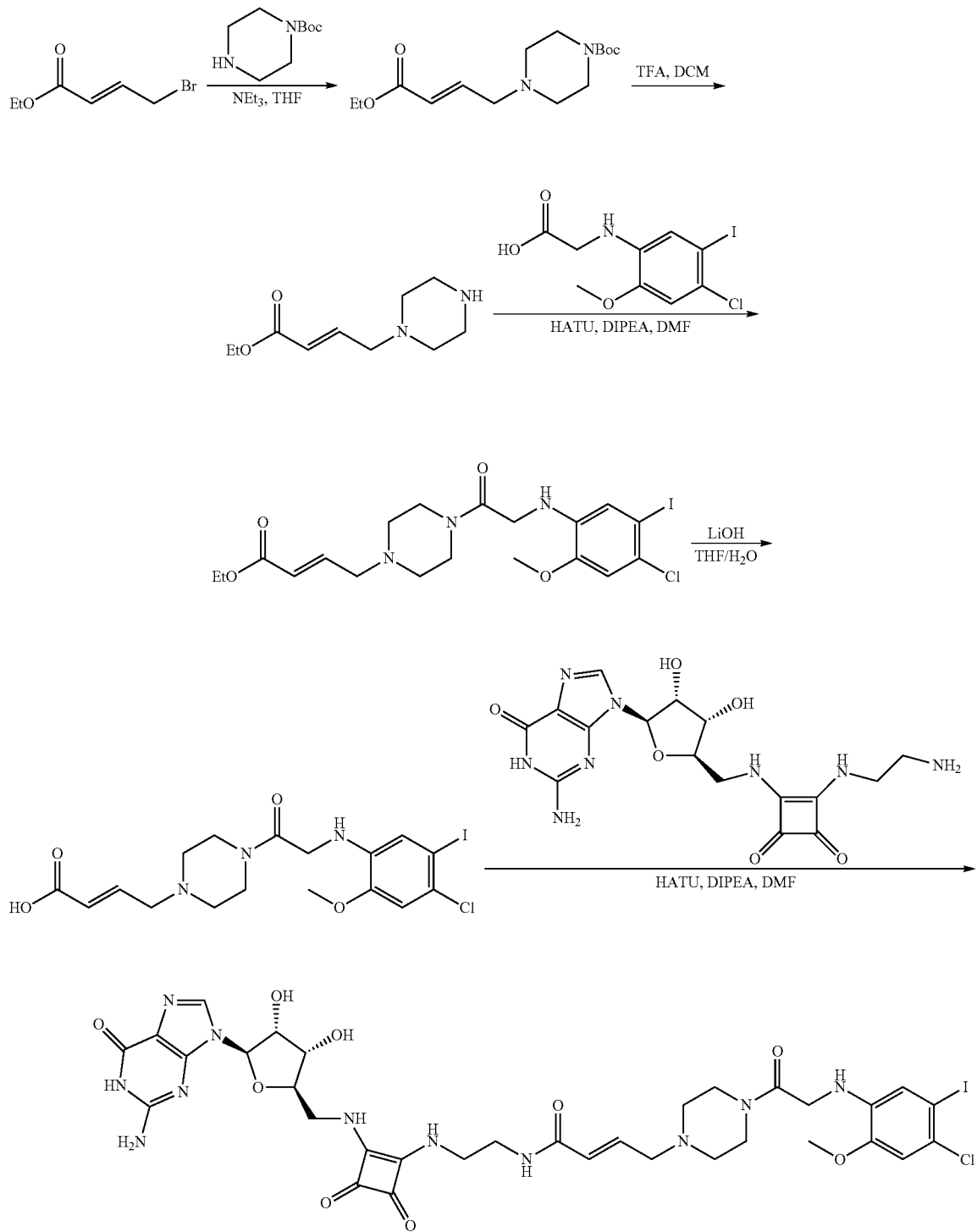

Step 1. tert-butyl (E)-4-(4-ethoxy-4-oxobut-2-en-1-yl)piperazine-1-carboxylate

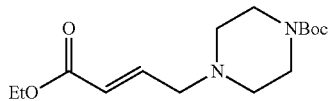 [SMILES: CCOC(=O)/C=C/CN1CCN(C(=O)OC(C)(C)C)CC1]

To a solution of ethyl (E)-4-bromobut-2-enoate (3.0 g, 26 mmol), and 1-Boc-piperazine (2.9 g, 26 mmol) in anhydrous THF (26 mL), triethylamine (6.48 mL, 78 mmol) was added dropwise. The solution stirred at room temperature for 12 hours. The reaction mixture was quenched with water and 1 N HCl and extracted with EtOAc. The organic layer was washed with brine, dried over $Na_2SO_4$, and concentrated in vacuo to give tert-butyl (E)-4-(4-ethoxy-4-oxobut-2-en-1-yl)piperazine-1-carboxylate which was used directly in the next step without further purification (3.7 g, 80%). RT (retention time in minutes): 1.83 (Method: A), Mass m/z: 299.12 (M+1).

Step 2. ethyl (E)-4-(piperazin-1-yl)but-2-enoate

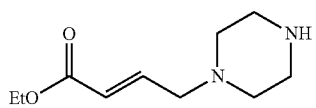 [SMILES: CCOC(=O)/C=C/CN1CCNCC1]

A solution of tert-butyl (E)-4-(4-ethoxy-4-oxobut-2-en-1-yl)piperazine-1-carboxylate (1 g, 3.3 mmol) in a mixture of TFA (10 mL) and DCM (10 mL) was stirred at room temperature for 12 hours. The volatiles were removed under reduced pressure, and the solid residue was triturated, filtered, and dried through nitrogen gas flow to give ethyl (E)-4-(piperazin-1-yl)but-2-enoate as a white powder in 95% yield (630 mg). RT: 0.97 (Method: A), Mass m/z: 199.08 (M+1).

Step 3. (E)-4-(4-((4-chloro-5-iodo-2-methoxyphenyl)glycyl)piperazin-1-yl)but-2-enoic acid

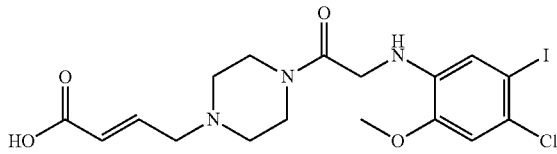 [SMILES: COc1cc(Cl)c(I)cc1NCC(=O)N1CCN(C/C=C/C(=O)O)CC1]

To a solution of ethyl (E)-4-(piperazin-1-yl)but-2-enoate (135 mg, 0.68 mmol) and (4-chloro-5-iodo-2-methoxyphenyl)glycine (233 mg, 0.68 mmol) in anhydrous DMF (3.4 ml) was added HATU (387 mg, 1.02 mmol) and DIPEA (0.237 mL, 1.36 mmol). The reaction mixture was stirred at room temperature for 12 hours. Water (4 mL) was added. The resulting mixture was extracted with EtOAc, and the organic layer was washed with water and brine, dried over $Na_2SO_4$, and concentrated under reduced pressure to give an oil. The oil was dissolved in a mixture of THF (2 mL) and water (1 mL), to which lithium hydroxide (86 mg, 2.04 mmol) was added in one portion. The mixture was stirred at room temperature for 1 h before being quenched with water. The mixture was extracted with EtOAc, and the organic layer was washed with water and brine, dried over $Na_2SO_4$, and concentrated under reduced pressure to give a white powder (200 mg, 60%). RT: 2.38 (Method: A), Mass m/z: 494.29 (M+1).

Step 4. (E)-N-(2-((2-(((((2R,3S,4R,5R)-5-(2-amino-6-oxo-1,6-dihydro-9H-purin-9-yl)-3,4-dihydroxytetrahydrofuran-2-yl)methyl)amino)-3,4-dioxocyclobut-1-en-1-yl)amino)ethyl)-4-(4-((4-chloro-5-iodo-2-methoxyphenyl)glycyl)piperazin-1-yl)but-2-enamide

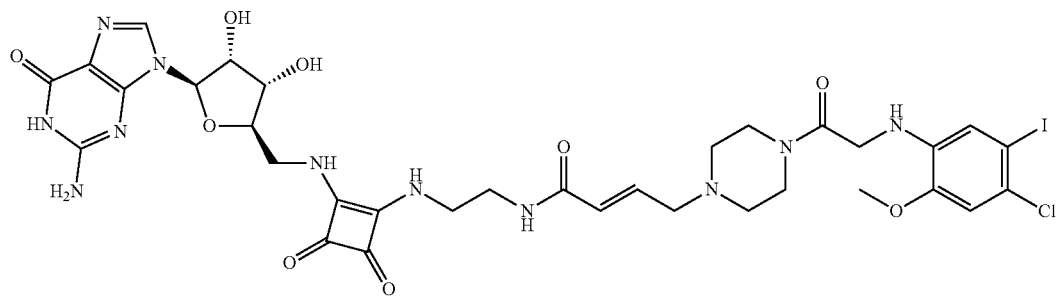 [SMILES: COc1cc(Cl)c(I)cc1NCC(=O)N1CCN(C/C=C/C(=O)NCCNc2c(NC[C@H]3O[C@@H](n4cnc5c(=O)[nH]c(N)nc54)[C@H](O)[C@@H]3O)c(=O)c2=O)CC1]

To a solution of (E)-4-(4-((4-chloro-5-iodo-2-methoxyphenyl)glycyl)piperazin-1-yl)but-2-enoic acid (15 mg, 0.03 mmol) and 3-((((2R,3S,4R,5R)-5-(2-amino-6-oxo-1,6-dihydro-9H-purin-9-yl)-3,4-dihydroxytetrahydrofuran-2-yl)methyl)amino)-4-((2-aminoethyl)amino)cyclobut-3-ene-1,2-dione (13 mg, 0.03 mmol) in anhydrous DMF (0.5 mL) were added HATU (17 mg, 0.05 mmol) and DIPEA (0.011 mL, 0.06 mmol). The reaction mixture was stirred at 50° C. for 5 hours before being quenched with water. The mixture was vigorously stirred for 10 min, and the aqueous layer was collected and directly purified by preparative reverse-phase HPLC (methanol/water gradient) to provide (E)-N-(2-((2-((((2R,3S,4R,5R)-5-(2-amino-6-oxo-1,6-dihydro-9H-purin-9-yl)-3,4-dihydroxytetrahydrofuran-2-yl)methyl)amino)-3,4-dioxocyclobut-1-en-1-yl)amino)ethyl)-4-(4-((4-chloro-5-iodo-2-methoxyphenyl)glycyl)piperazin-1-yl)but-2-enamide (1.2 mg, 4%). RT: 2.23 (Method: A), Mass m/z: 896.50 (M+1).

Example 32

3-((((2R,3S,4R,5R)-5-(2-amino-6-oxo-1,6-dihydro-9H-purin-9-yl)-3,4-dihydroxytetrahydrofuran-2-yl)methyl)amino)-4-((2-(((E)-4-(4-((4-chloro-5-iodo-2-methoxyphenyl)glycyl)piperazin-1-yl)-4-oxobut-2-en-1-yl)(methyl)amino)ethyl)amino)cyclobut-3-ene-1,2-dione

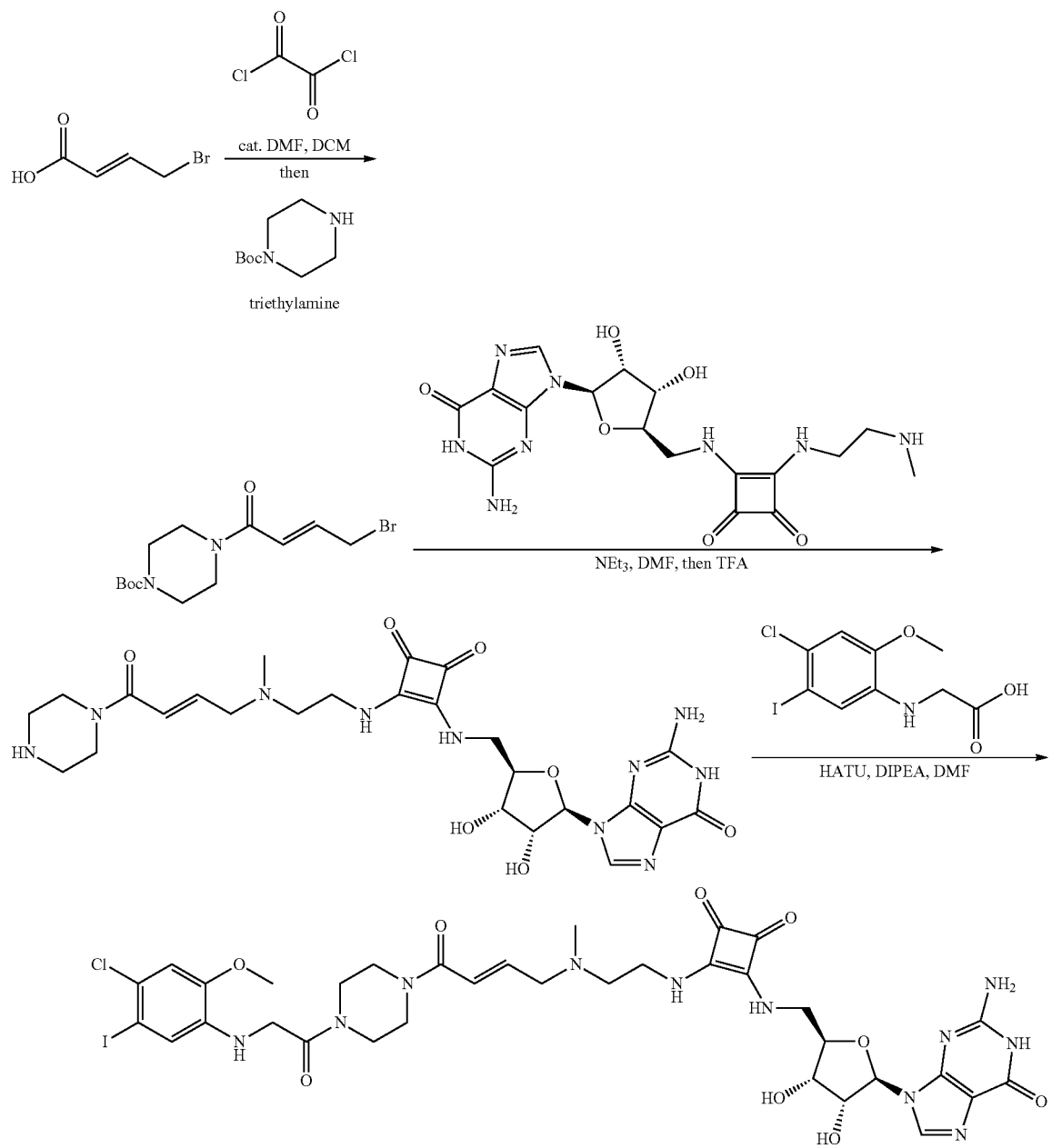

Scheme 6.

Step 1. tert-butyl (E)-4-(4-bromobut-2-enoyl)piperazine-1-carboxylate

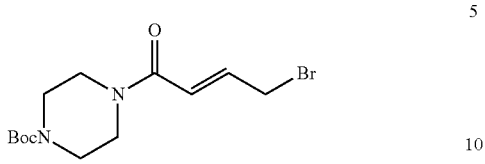

To a solution of (E)-4-bromobut-2-enoic acid (200 mg, 1.2 mmol) in DCM (20 mL), was added 1 drop of anhydrous DMF, followed by dropwise addition of oxalyl chloride (6.48 mL, 78 mmol) at 0° C. The solution was warmed up to room temperature and stirred at room temperature for 1 hours. The reaction mixture was concentrated under reduced pressure and redissolved in DCM (6 mL). To the mixture was added 1-Boc-piperazine (225 mg, 1.2 mmol) and triethylamine (0.51 mL, 3.6 mmol). The resulting mixture was stirred at room temperature for 1 h and quenched with water. The mixture was extracted with EtOAc, and the organic layer was washed with water and brine, dried over $Na_2SO_4$, and concentrated under reduced pressure to give a yellow oil. The yellow oil was purified using flash column chromatography (0-10% methanol-dichloromethane) to provide tert-butyl (E)-4-(4-bromobut-2-enoyl)piperazine-1-carboxylate as a yellow solid. RT: 2.95 (Method: A), Mass m/z: 333.36 (M+1).

Step 2. 3-((((2R,3S,4R,5R)-5-(2-amino-6-oxo-1,6-dihydro-9H-purin-9-yl)-3,4-dihydroxytetrahydrofuran-2-yl)methyl)amino)-4-((2-(methyl((E)-4-oxo-4-(piperazin-1-yl)but-2-en-1-yl)amino)ethyl)amino)cyclobut-3-ene-1,2-dione

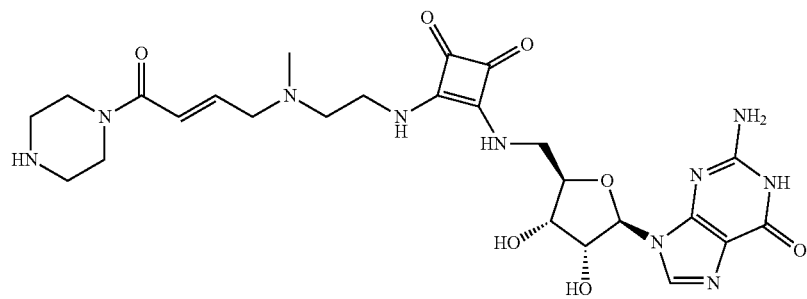 [SMILES: CN(C/C=C/C(=O)N1CCNCC1)CCNc1c(NC[C@H]2O[C@@H](n3cnc4c(=O)[nH]c(N)nc43)[C@H](O)[C@@H]2O)c(=O)c1=O]

To a solution of tert-butyl (E)-4-(4-bromobut-2-enoyl) piperazine-1-carboxylate (46 mg, 0.12 mmol) and 3-((((2R, 3S,4R,5R)-5-(2-amino-6-oxo-1,6-dihydro-9H-purin-9-yl)-3,4-dihydroxytetrahydrofuran-2-yl)methyl)amino)-4-((2-(methylamino)ethyl)amino)cyclobut-3-ene-1,2-dione (50 mg, 0.12 mmol) in anhydrous DMF (0.5 mL) was added triethylamine (0.05 mL, 0.36 mmol). The reaction mixture was stirred at 50° C. for 12 hours before being quenched with water. The mixture was vigorously stirred for 10 min, and the aqueous layer was collected and directly purified by preparative reverse-phase HPLC (methanol/water gradient) to provide tert-butyl 4-((E)-4-((2-((2-((((2R,3S,4R,5R)-5-(2-amino-6-oxo-1,6-dihydro-9H-purin-9-yl)-3,4-dihydroxytetrahydrofuran-2-yl)methyl)amino)-3,4-dioxocyclobut-1-en-1-yl)amino)ethyl)(methyl)amino)but-2-enoyl) piperazine-1-carboxylate as a white powder. RT: 1.72 (Method: A), Mass m/z: 687.61 (M+1). The white powder was subsequently subjected to a solution of DCM-TFA (1:1) at room temperature for 1 hour. The reaction mixture was concentrated under reduced pressure to yield 3-((((2R,3S,4R,5R)-5-(2-amino-6-oxo-1,6-dihydro-9H-purin-9-yl)-3,4-dihydroxytetrahydrofuran-2-yl)methyl)amino)-4-((2-(methyl((E)-4-oxo-4-(piperazin-1-yl)but-2-en-1-yl)amino)ethyl)amino)cyclobut-3-ene-1,2-dione as a white powder (30 mg, 37%), which was used directly in the next step without further purification.

Step 3. 3-((((2R,3S,4R,5R)-5-(2-amino-6-oxo-1,6-dihydro-9H-purin-9-yl)-3,4-dihydroxytetrahydrofuran-2-yl)methyl)amino)-4-((2-(((E)-4-(4-((4-chloro-5-iodo-2-methoxyphenyl)glycyl)piperazin-1-yl)-4-oxobut-2-en-1-yl)(methyl)amino)ethyl)amino)cyclobut-3-ene-1,2-dione

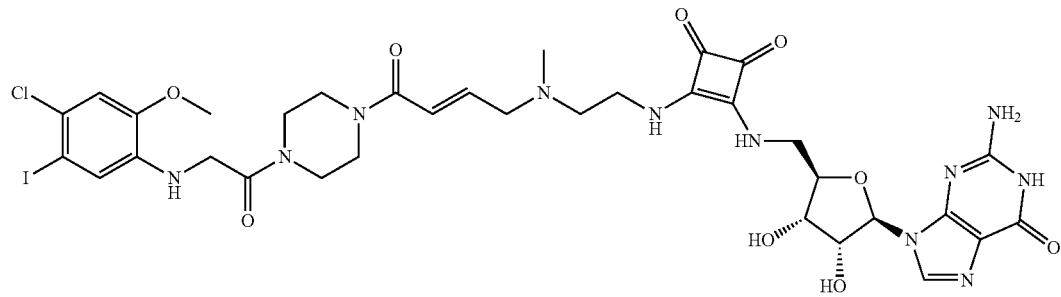 [SMILES: COc1cc(Cl)c(I)cc1NCC(=O)N1CCN(C(=O)/C=C/CN(C)CCNc2c(NC[C@H]3O[C@@H](n4cnc5c(=O)[nH]c(N)nc54)[C@H](O)[C@@H]3O)c(=O)c2=O)CC1]

To a solution of 3-((((2R,3S,4R,5R)-5-(2-amino-6-oxo-1,6-dihydro-9H-purin-9-yl)-3,4-dihydroxytetrahydrofuran-2-yl)methyl)amino)-4-((2-(methyl((E)-4-oxo-4-(piperazin-1-yl)but-2-en-1-yl)amino)ethyl)amino)cyclobut-3-ene-1,2-dione (20 mg, 0.03 mmol) and (4-chloro-5-iodo-2-methoxyphenyl)glycine (12 mg, 0.03 mmol) in anhydrous DMF (1 ml) was added HATU (19 mg, 0.05 mmol) and DIPEA (0.012 mL, 0.07 mmol). The reaction mixture was stirred at 50° C. for 12 hours and was quenched with water. The mixture was vigorously stirred for 10 min, and the aqueous layer was collected and directly purified by preparative reverse-phase HPLC (methanol/water gradient) to provide the title compound as an off white powder. RT: 2.44 (Method: A), Mass m/z: 910.61 (M+1).

Compounds prepared based on Example 4 are shown in Table 2.

TABLE 2

Compounds Prepared Based on Example 21, 31, or 32.

| Compound Code | Structure | NMR, Retention time (min) and/or Mass m/z: (M + 1). |
|---|---|---|
| Example 22 | 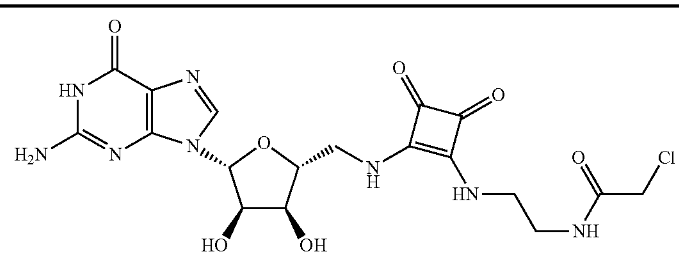 | 1.83 (A), 497.23 (M + 1) |

TABLE 2-continued

Compounds Prepared Based on Example 21, 31, or 32.

| Compound Code | Structure | NMR, Retention time (min) and/or Mass m/z: (M + 1). |
|---|---|---|
| Example 23 | 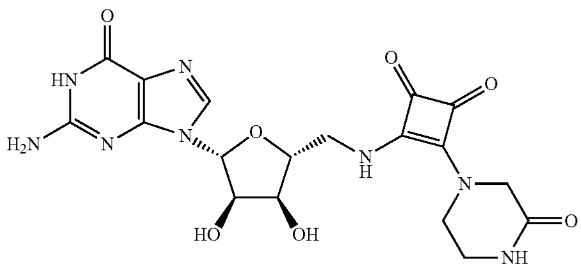 [SMILES: Nc1nc2c(ncn2[C@@H]2O[C@H](CNc3c(N4CCNC(=O)C4)c(=O)c3=O)[C@@H](O)[C@H]2O)c(=O)[nH]1] | 1.37 (A), 461.20 (M + 1) |
| Example 24 | 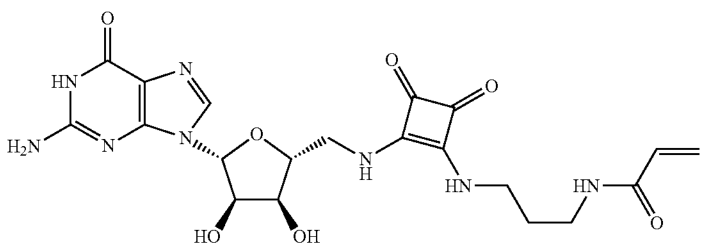 [SMILES: C=CC(=O)NCCCNc1c(NC[C@H]2O[C@@H](n3cnc4c(=O)[nH]c(N)nc43)[C@H](O)[C@@H]2O)c(=O)c1=O] | 2.07 (A), 489.30 (M + 1) |
| Example 25 | 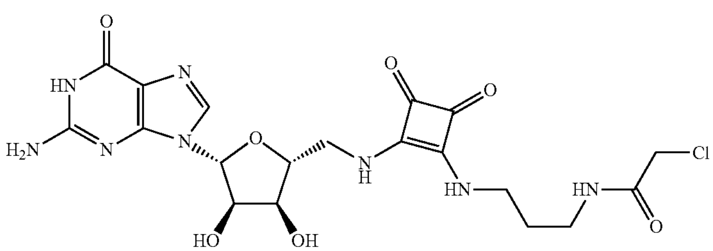 [SMILES: Nc1nc2c(ncn2[C@@H]2O[C@H](CNc3c(NCCCNC(=O)CCl)c(=O)c3=O)[C@@H](O)[C@H]2O)c(=O)[nH]1] | 2.05 (A), 511.22 (M + 1) |
| Example 26 | 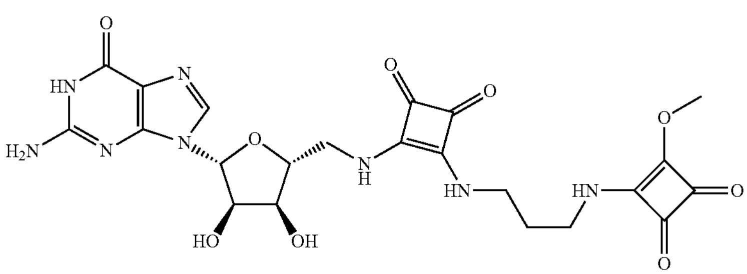 [SMILES: COc1c(NCCCNc2c(NC[C@H]3O[C@@H](n4cnc5c(=O)[nH]c(N)nc54)[C@H](O)[C@@H]3O)c(=O)c2=O)c(=O)c1=O] | 1.90 (A), 545.24 (M + 1) |
| Example 27 | 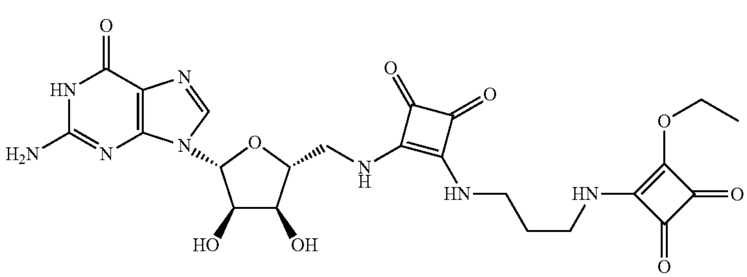 [SMILES: CCOc1c(NCCCNc2c(NC[C@H]3O[C@@H](n4cnc5c(=O)[nH]c(N)nc54)[C@H](O)[C@@H]3O)c(=O)c2=O)c(=O)c1=O] | 2.15 (A), 559.23 (M + 1) |

TABLE 2-continued

Compounds Prepared Based on Example 21, 31, or 32.

| Compound Code | Structure | NMR, Retention time (min) and/or Mass m/z: (M + 1). |
|---|---|---|
| Example 28 | 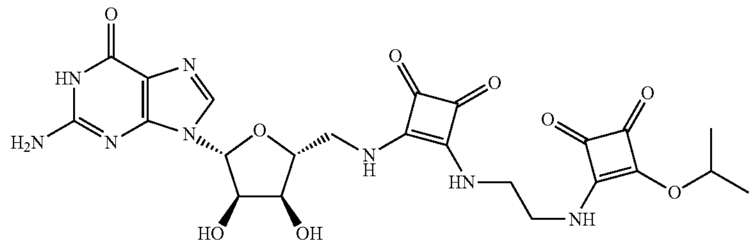 [SMILES: CC(C)Oc1c(NCCNc2c(NC[C@H]3O[C@@H](n4cnc5c(=O)[nH]c(N)nc54)[C@H](O)[C@@H]3O)c(=O)c2=O)c(=O)c1=O] | 2.18 (A), 559.23 (M + 1) |
| Example 29 | 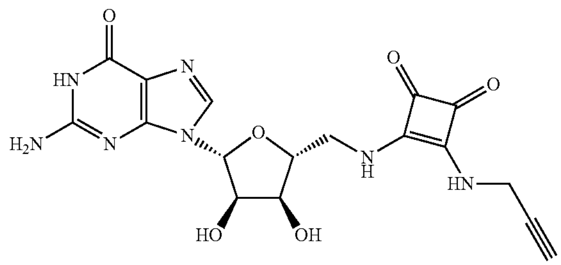 [SMILES: C#CCNc1c(NC[C@H]2O[C@@H](n3cnc4c(=O)[nH]c(N)nc43)[C@H](O)[C@@H]2O)c(=O)c1=O] | 1.47 (A), 417.22 (M + 1) |
| Example 30 | 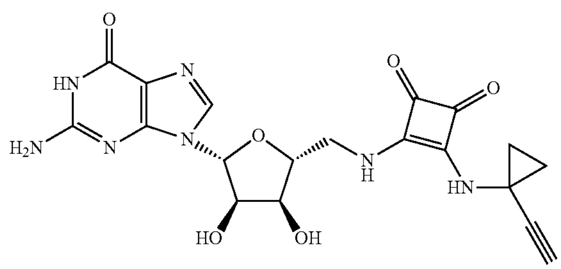 [SMILES: C#CC1(Nc2c(NC[C@H]3O[C@@H](n4cnc5c(=O)[nH]c(N)nc54)[C@H](O)[C@@H]3O)c(=O)c2=O)CC1] | 1.67 (A), 443.43 (M + 1) |
| Example 31 | 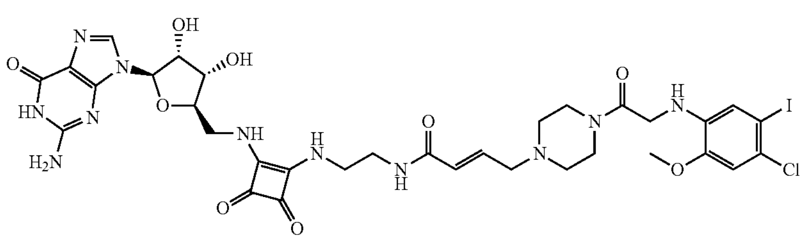 [SMILES: COc1cc(Cl)c(I)cc1NCC(=O)N1CCN(C/C=C/C(=O)NCCNc2c(NC[C@H]3O[C@@H](n4cnc5c(=O)[nH]c(N)nc54)[C@H](O)[C@@H]3O)c(=O)c2=O)CC1] | 2.23 (A), 896.50 (M + 1) |
| Example 33 | 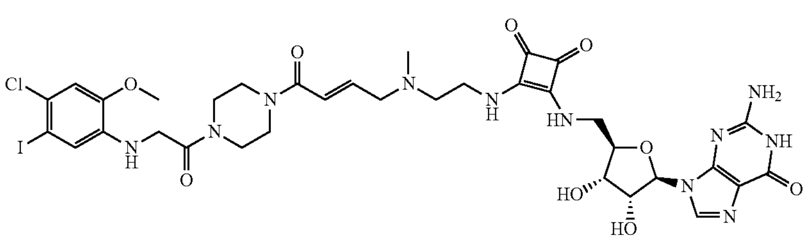 [SMILES: COc1cc(Cl)c(I)cc1NCC(=O)N1CCN(C(=O)/C=C/CN(C)CCNc2c(NC[C@H]3O[C@@H](n4cnc5c(=O)[nH]c(N)nc54)[C@H](O)[C@@H]3O)c(=O)c2=O)CC1] | 2.44 (A), 910.61 (M + 1) |

Biological Experiment

1. Anti-Proliferation Experiment:

A549 (K-Ras G12S), H23 (K-Ras G12C) and H358 (K-Ras G12C) cells were cultured in 60 mm plate with 10% fetal bovine serum (FBS), Roswell Park Memorial Institute medium (RPMI) medium. The anti-proliferation assay was carried out by using 96 well white bottom plates. 2000-4000 cells were seeded per well, and the medium volume per well was about 100 ul. Incubate for 3 days after adding and titrating indicated concentration of compounds. The cell viability was test by CellTiter-Glo® Luminescent Assay. In a typical experiment, add 10 ul CellTiter-Glo® reagent per well. Mix and shake the plate for 2 minutes to induce cell lysis at room temperature. Allow the plate to incubate at room temperature for approximately 10 minutes to stabilize luminescent signal. Read plate with Perkin Elmer EnVision.

The cell numbers were normalized by the DMSO control. And the EC50s were calculated by GraphPad Prism.

2. Western Blotting Experiment:

When the confluence reached 80%, the previous mentioned cells were treated with compounds in indicated concentration. After 8 hours, wash cells with PBS for three times. Cells were lysed with lysis buffer (25 mM Tris-HCl pH 7.4, 150 mM NaCl, 1 mM EDTA, 1% NP-40, 5% glycerol, Roche PhosSTOP phosphatase inhibitor cocktail tablets and Roche Complete Protease inhibitor cocktail tablets). The cell lysate was rotated end-to-end for approximately 30 min, centrifuged at 10,000 g for 15 minutes at 4° C. The supernatant was transferred to new tubes. The total protein concentration was measure by Pierce BCA protein assay: BCA reagent A and B were mixed with the ration of 20:1. Pipette 1 ml the mixture to each disposal plastic cuvette, add 2 ul lysate. Incubate at 37° C. for approximately 30 minutes. Cool all tubes to room temperature. With the spectrophotometer set to 562 nm, zero the instrument on a cuvette filled only with water. Subsequently, measure the absorbance of all the samples with 10 minutes. Subtract the average 562 nm absorbance measurement of the Blank standard replicates from the 562 nm absorbance measurement of all other individual standard and unknown sample replicates. Prepare a standard curve by plotting the average Blank-corrected 562 nm measurement for each BSA standard vs. its concentration. Use the standard curve to determine the protein concentration of each unknown sample. Dilute all samples to 1.0 mg/ml with lysis buffer. Add same volume 1:1 loading buffer to samples, heat samples at 95° C. for 10 min. Run samples on an SDS-PAGE gel at 110V. After transferred, the membrane was immunoblotted with antibodies: Phospho-Akt (Ser473) antibody, Cell Signaling 4060; Akt antibody, Cell Signaling 9272; Phospho-p44/42 MAPK (Erk1/2) (Thr202/Thr204), Cell Signaling 9101; p44/42 MAPK (Erk1/2), Cell Signaling 9102.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I)

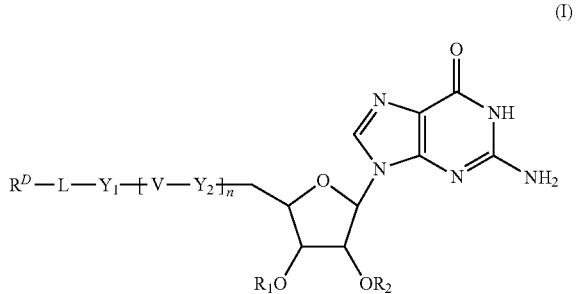

or a pharmaceutically acceptable salt thereof,
wherein:
each of $R_1$ and $R_2$ is independently hydrogen, optionally substituted alkyl, or an oxygen protecting group, or $R_1$ and $R_2$ are taken together with their intervening atoms to form an optionally substituted heterocyclic ring;
L is a bond, optionally substituted $C_{1-6}$ alkylene, —O—, —S—, or —NR$^N$—;
$Y_1$ is —O—, —NR$^N$—, or —C(R$^C$)$_2$—;
each instance of $Y_2$ is independently —O—, —S—, —NR$^N$—, or —C(R$^C$)$_2$—;
each instance of V is independently —C(=O)—, —S(=O)$_2$—, or

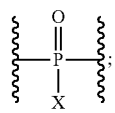

each instance of X is independently hydrogen, —OR$^O$, or —NR$^{N1}$R$^{N2}$;

each instance of R$^N$, R$^{N1}$, and R$^{N2}$ is independently hydrogen, optionally substituted alkyl, or a nitrogen protecting group; or R$^{N1}$ and R$^{N2}$ are taken together with their intervening atoms to form an optionally substituted heterocyclic ring;

each instance of R$^O$ is independently hydrogen, optionally substituted alkyl, optionally substituted aryl, or an oxygen protecting group;

each instance of R$^C$ is independently hydrogen, halogen, or optionally substituted alkyl;

n is 1, 2, or 3; and

R$^D$ is of the formula:

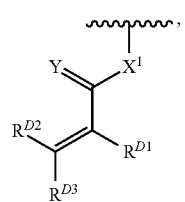
(i-1)

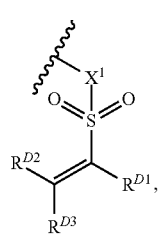
(i-2)

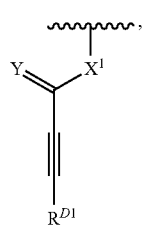
(i-3)

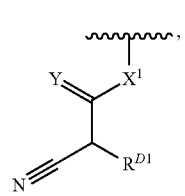
(i-4)

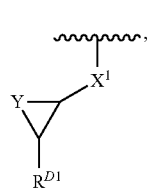
(i-6)

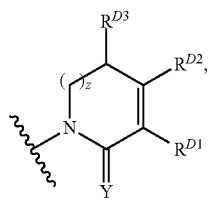
(i-7)

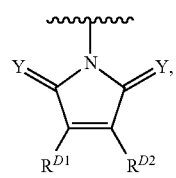
(i-8)

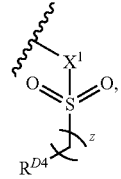
(i-10)

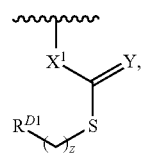
(i-12)

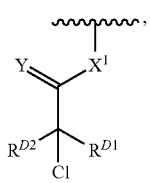
(i-14)

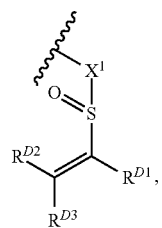
(i-15)

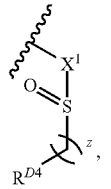
(i-16)

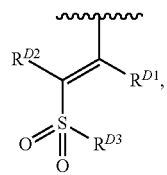
(i-17)

-continued (i-18)

(i-20)

(i-21)

(i-22)

(i-23)

(i-24)

(i-25)

(i-26)

(i-27)

-continued (i-28)

(i-29)

(i-30)

(i-31)

(i-33)

(i-35)

(i-36)

(i-38)

(i-39)

(i-40)

wherein:
each instance of $R^{D1}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, or —C(=NR$^{D1a}$)N(R$^{D1a}$)$_2$, wherein each occurrence of R$^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D1a}$ groups are joined to form an substituted or unsubstituted heterocyclic ring;

each instance of R$^{D2}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, and —C(=NR$^{D2a}$)N(R$^{D2a}$)$_2$, wherein each occurrence of R$^{D2a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two R$^{D2a}$ groups are joined to form an substituted or unsubstituted heterocyclic ring;

each instance of R$^{D3}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, or —C(=NR$^{D3a}$)N(R$^{D3a}$)$_2$ wherein each occurrence of R$^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D3a}$ groups are joined to form an substituted or unsubstituted heterocyclic ring;

optionally R$^{D1}$ and R$^{D3}$, or R$^{D2}$ and R$^{D3}$, or R$^{D1}$ and R$^{D2}$ are joined to form an substituted or unsubstituted carbocyclic or substituted or unsubstituted heterocyclic ring;

R$^{D4}$ is a leaving group selected from the group consisting of —Br, —Cl, —I, and —OS(=O)$_w$R$^{D4a}$, wherein w is 1 or 2, and R$^{D4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of X$^1$ is independently a bond, —C(=O)—, —S(=O)$_2$—, NR$^{D5}$, optionally substituted alkylene, or optionally substituted heteroarylene, wherein R$^{D5}$ is hydrogen, C$_{1-6}$ alkyl, or a nitrogen protecting group;

each instance of Y is independently O, S, or NR$^{D6}$, wherein R$^{D6}$ is hydrogen, C$_{1-6}$ alkyl, or a nitrogen protecting group; and each instance of z and z$_1$ is independently 0, 1, 2, 3, 4, 5, or 6, as valency permits.

2. The compound of claim 1, wherein the compound is of Formula (I-a):

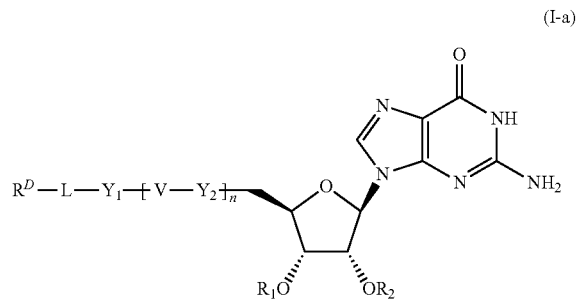

or a pharmaceutically acceptable salt thereof.

3. The compound of claim 1, wherein the compound is of Formula (I-b):

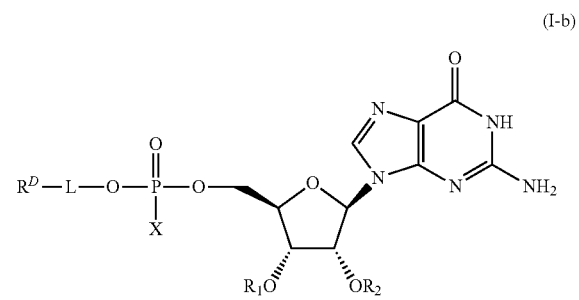

or a pharmaceutically acceptable salt thereof.

4. The compound of claim 1, wherein the compound is of Formula (I-b1):

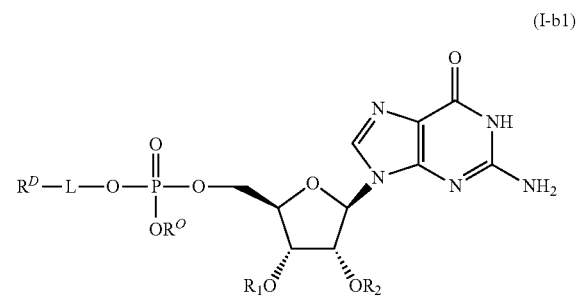

or a pharmaceutically acceptable salt thereof.

5. The compound of claim 1, wherein the compound is of Formula (I-c):

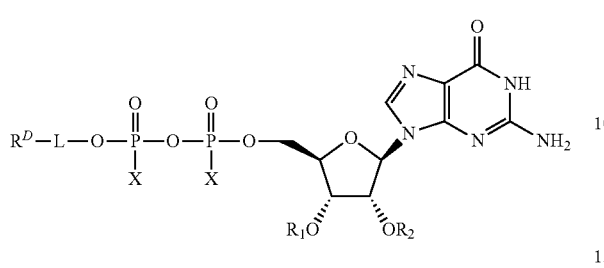

(I-c)

or a pharmaceutically acceptable salt thereof.

6. The compound of claim 1, wherein the compound is of Formula (I-c1) or (I-c2):

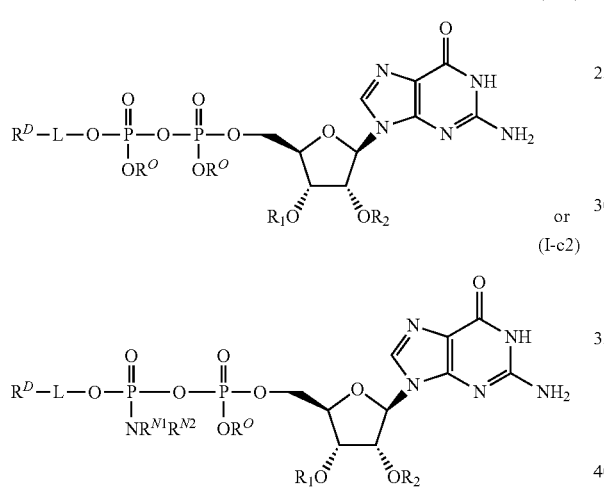

(I-c1)

or (I-c2)

or a pharmaceutically acceptable salt thereof.

7. The compound of claim 1, wherein the compound is of Formula (I-c2-1):

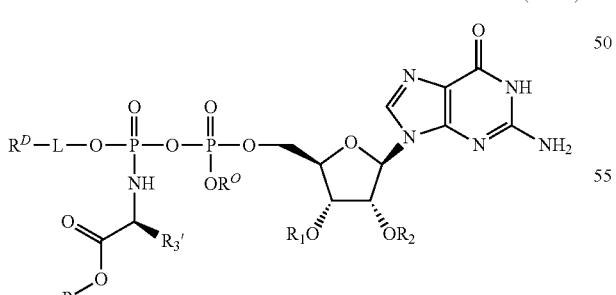

(I-c2-1)

or a pharmaceutically acceptable salt thereof, wherein:

$R_3$ is optionally substituted alkyl, optionally substituted heteroalkyl, optionally substituted aralkyl, or optionally substituted carbocyclyl; and $R_3$ is hydrogen, optionally substituted alkyl, optionally substituted carbocyclyl, optionally substituted heteroalkyl, or optionally substituted aralkyl.

8. The compound of claim 1, wherein the compound is of Formula (I-d):

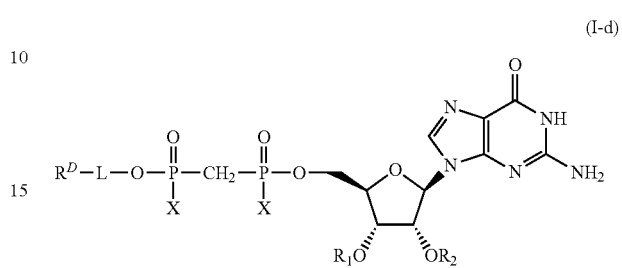

(I-d)

or a pharmaceutically acceptable salt thereof.

9. The compound of claim 1, wherein the compound is of Formula (I-d1) or (I-d2):

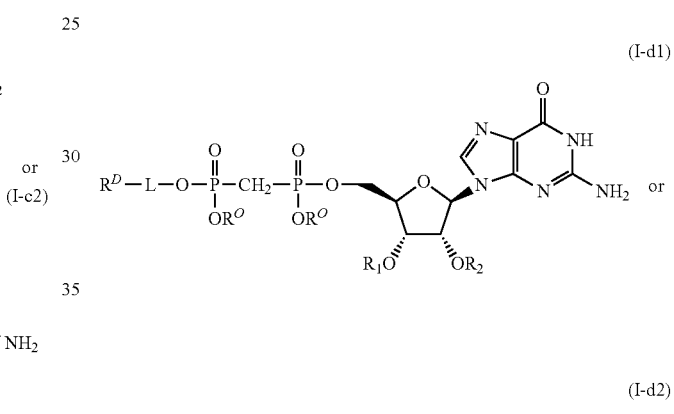

(I-d1)

or (I-d2)

or a pharmaceutically acceptable salt thereof.

10. The compound of claim 1, wherein the compound is of Formula (I-e):

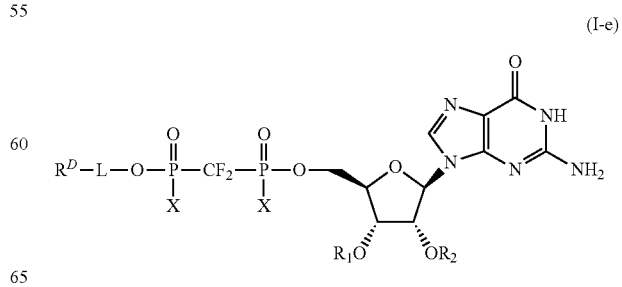

(I-e)

or a pharmaceutically acceptable salt thereof.

11. The compound of claim 1, wherein the compound is of Formula (I- or (I-e2):

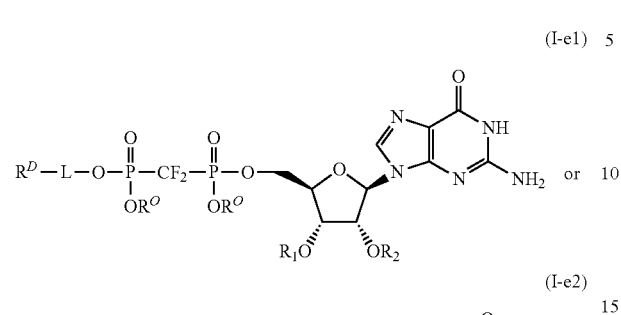

or a pharmaceutically acceptable salt thereof.

12. The compound of claim 1, wherein the compound is of Formula (I-f):

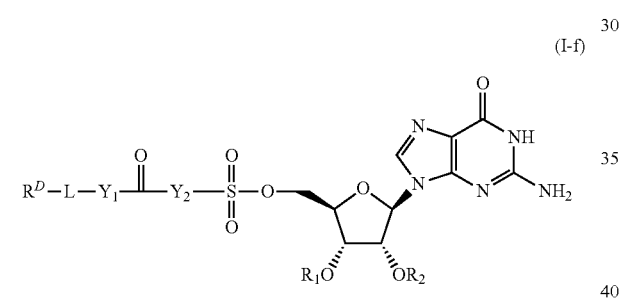

or a pharmaceutically acceptable salt thereof.

13. The compound of claim 1, wherein the compound is of Formula (I-f1):

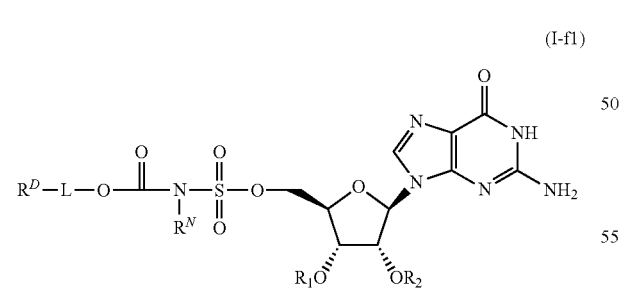

or a pharmaceutically acceptable salt thereof.

14. The compound of claim 1, or a pharmaceutically acceptable salt thereof, wherein L is —$(CH_2)_m$—, wherein m is 1, 2, 3, 4, 5, or 6.

15. The compound of claim 1, or a pharmaceutically acceptable salt thereof, wherein $R_1$ and $R_2$ are taken together with their intervening atoms to form a heterocyclic ring of the formula

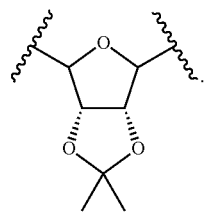 [SMILES: *C1OC(*)[C@@H]2OC(C)(C)O[C@H]12]

16. The compound of claim 1, or a pharmaceutically acceptable salt thereof, wherein $R^D$ is

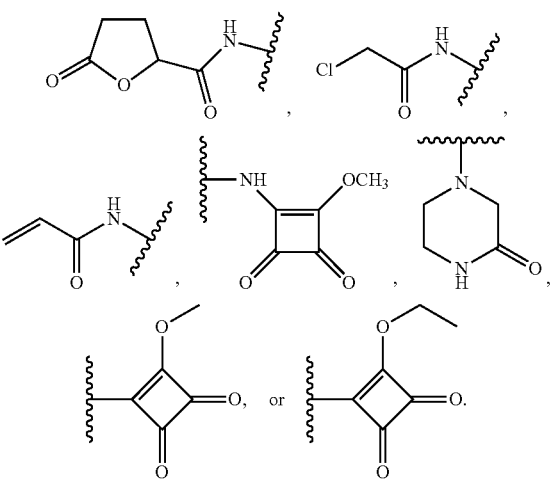

17. The compound of claim 1, wherein the compound is of the formula:

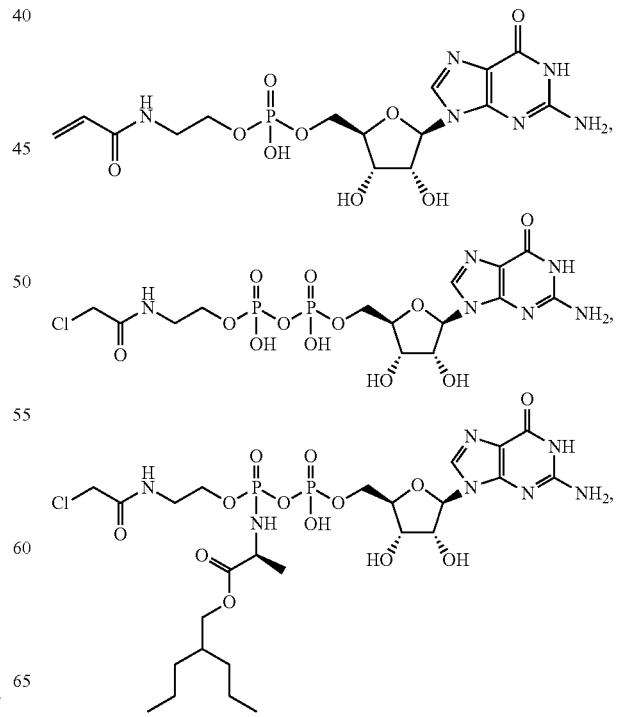

| 179 | 180 |
|---|---|
| -continued | -continued |
| 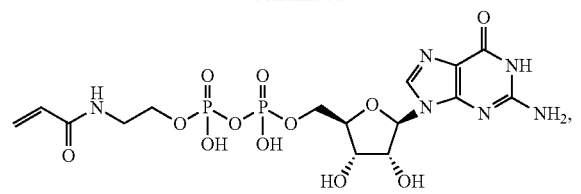 | 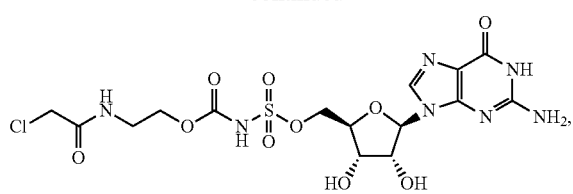 |
| 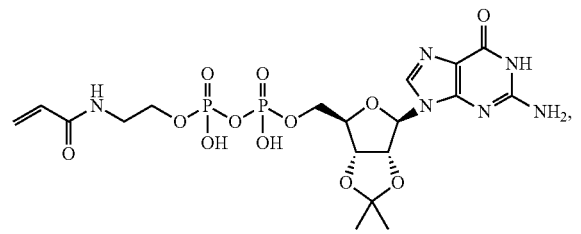 | 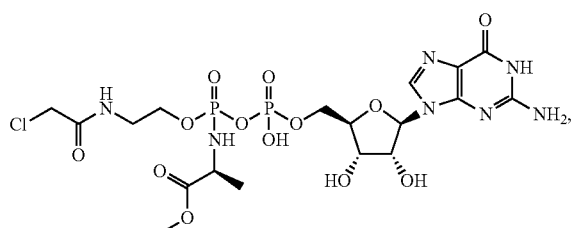 |
| 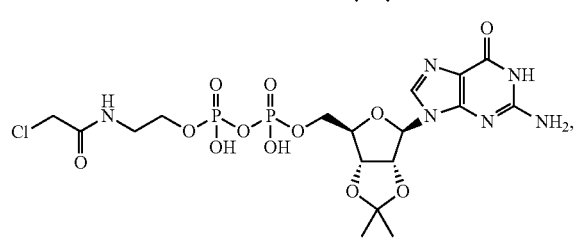 | 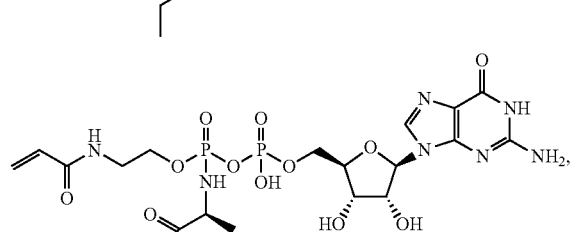 |
| 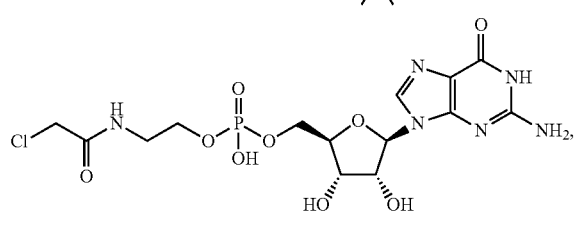 | 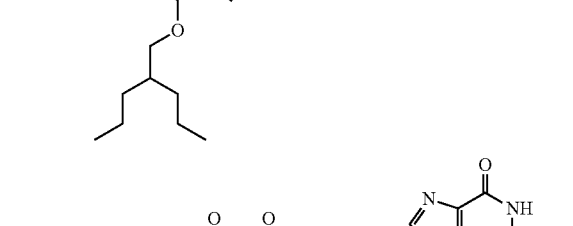 |
| 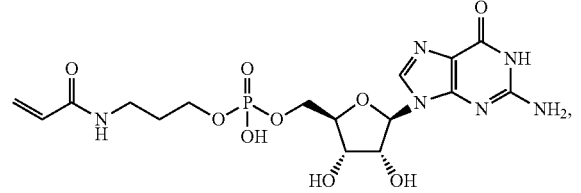 | 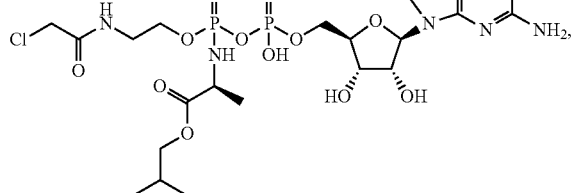 |
| 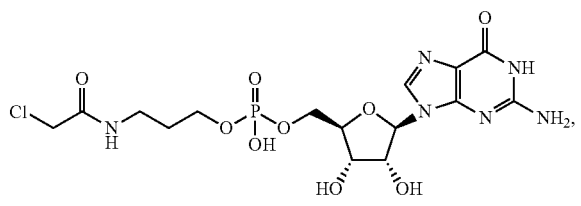 | 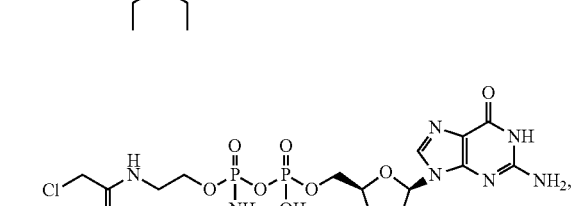 |
| 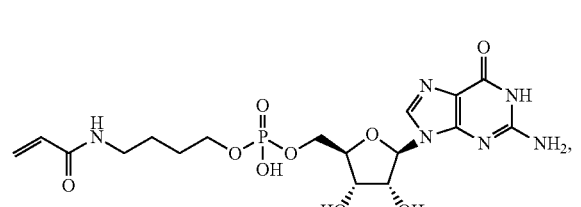 | 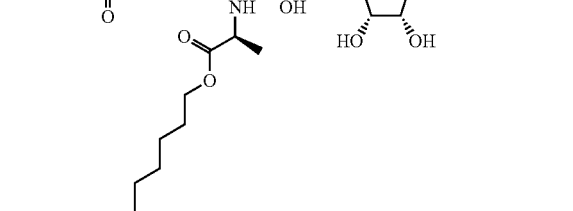 |
| 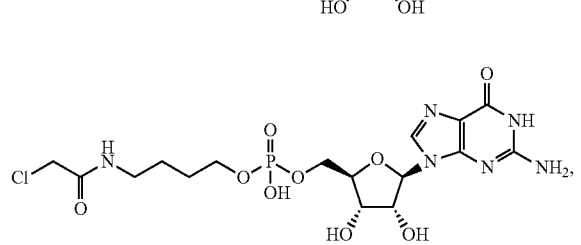 |  |

-continued

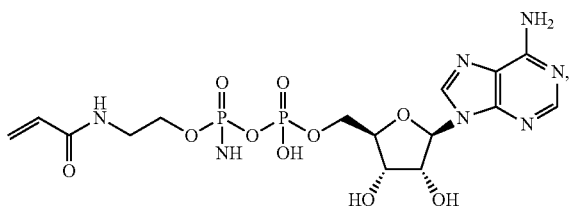

or

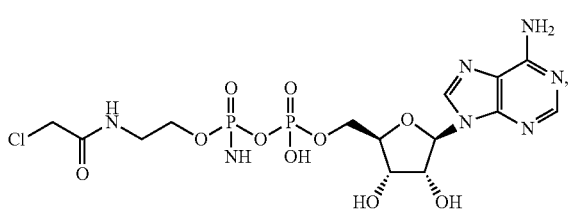

or a pharmaceutically acceptable salt thereof.

18. A pharmaceutical composition comprising a compound of claim 1, or a pharmaceutically acceptable salt thereof, and optionally a pharmaceutically acceptable excipient.

19. The compound of claim 1, or a pharmaceutically acceptable salt thereof, wherein each of $R_1$ and $R_2$ is hydrogen.

20. The compound of claim 1, or a pharmaceutically acceptable salt thereof, wherein $R^D$ is:

(i-1)

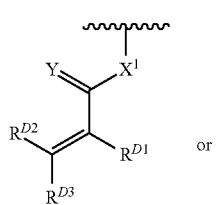

or (i-14)

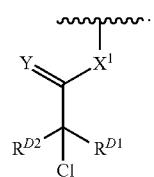

21. A compound of Formula (II):

(II)

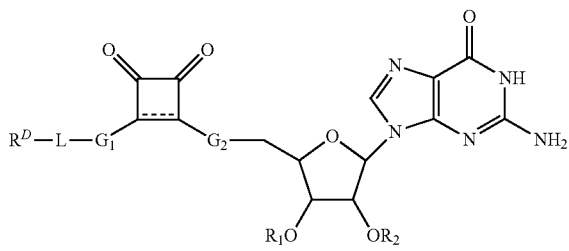

or a pharmaceutically acceptable salt thereof, wherein:

= represents a single bond or a double bond;

each of $R_1$ and $R_2$ is independently hydrogen, optionally substituted alkyl, or an oxygen protecting group, or $R_1$ and $R_2$ are taken together with their intervening atoms to form an optionally substituted heterocyclic ring;

L is a bond, optionally substituted $C_{1-6}$ alkylene, —O—, —S—, or —NR$^N$—;

each instance of $G_1$ and $G_2$ is independently —O—, —S—, —NR$^N$—, or —C(R$^C$)$_2$—;

each instance of R$^N$ is independently hydrogen, optionally substituted alkyl, or a nitrogen protecting group;

each instance of R$^C$ is independently hydrogen, halogen, or optionally substituted alkyl; and $R^D$ is of the formula:

(i-1)

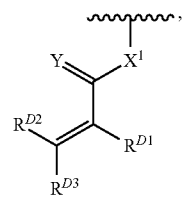

(i-2)

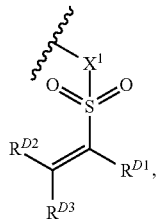, (i-3)

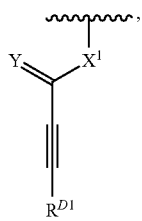

(i-4)

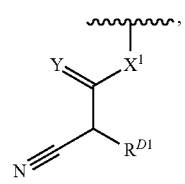

(i-5)

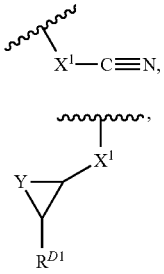

(i-6)

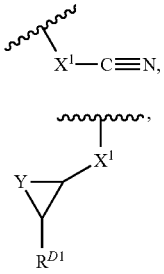

-continued
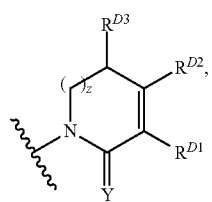 (i-7)
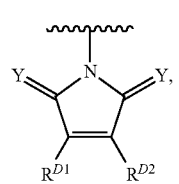 (i-8)
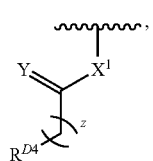 (i-9)
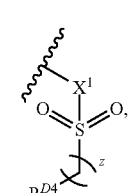 (i-10)
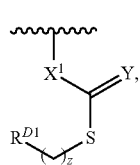 (i-12)
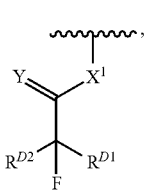 (i-13)
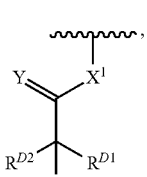 (i-14)
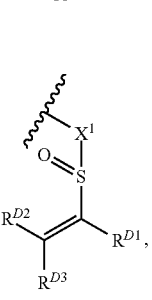 (i-15)
-continued
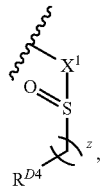 (i-16)
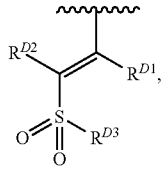 (i-17)
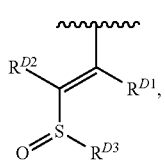 (i-18)
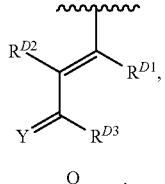 (i-19)
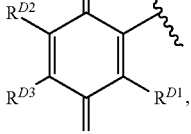 (i-20)
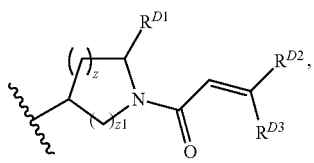 (i-21)
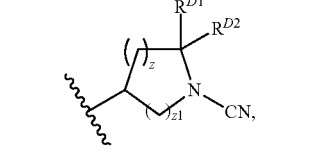 (i-22)
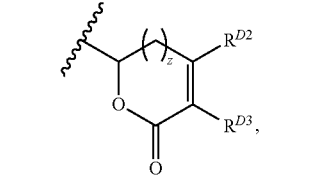 (i-23)
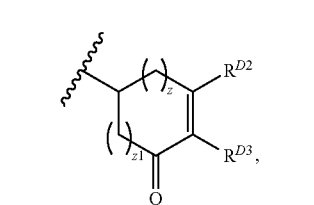 (i-24)

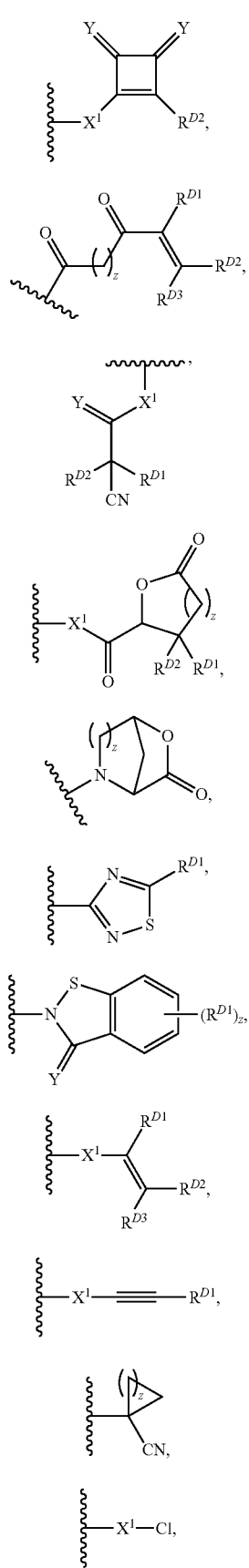
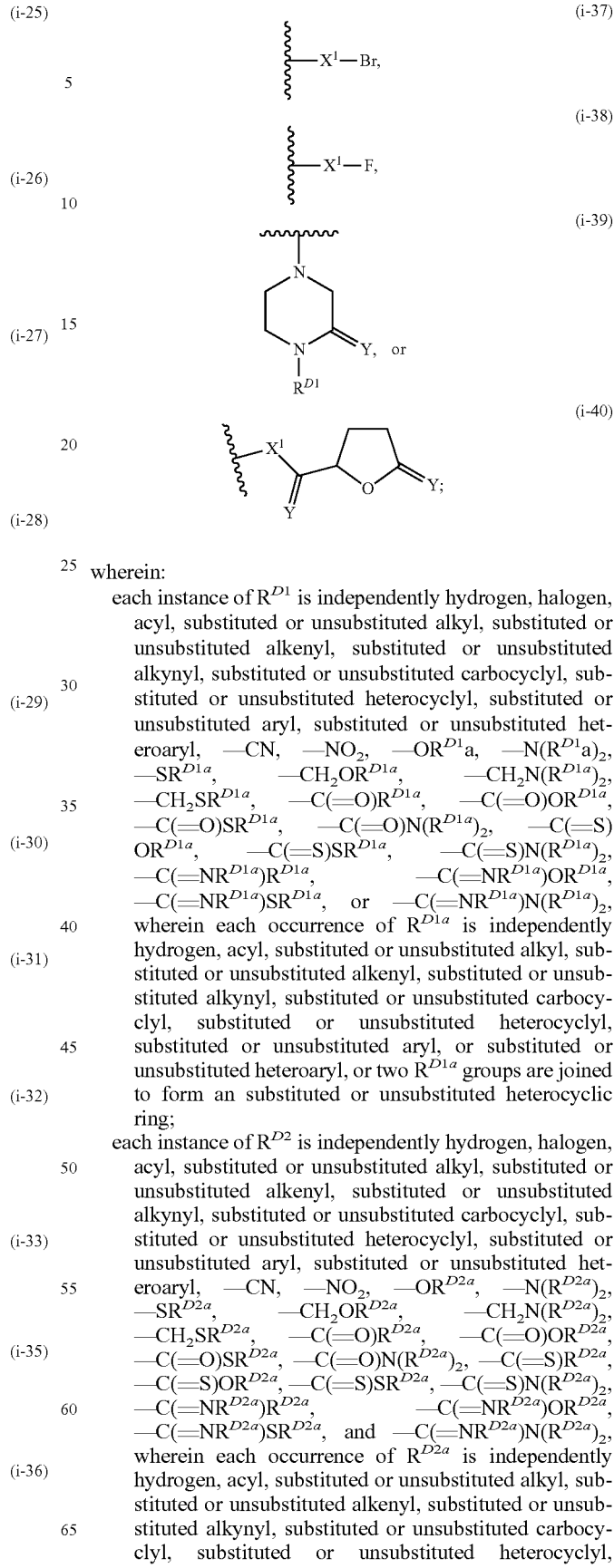

wherein:
each instance of $R^{D1}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1}$a, —N(R$^{D1}$a)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, or —C(=NR$^{D1a}$)N(R$^{D1a}$)$_2$, wherein each occurrence of $R^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D1a}$ groups are joined to form an substituted or unsubstituted heterocyclic ring;
each instance of $R^{D2}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, and —C(=NR$^{D2a}$)N(R$^{D2a}$)$_2$, wherein each occurrence of $R^{D2a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two $R^{D2a}$ groups are joined to form an substituted or unsubstituted heterocyclic ring;

each instance of $R^{D3}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D3a}$, —$N(R^{D3a})_2$, —$SR^{D3a}$, —$CH_2OR^{D3a}$, —$CH_2N(R^{D3a})_2$, —$CH_2SR^{D3a}$, —$C(=O)R^{D3a}$, —$C(=O)OR^{D3a}$, —$C(=O)SR^{D3a}$, —$C(=O)N(R^{D3a})_2$, —$C(=S)R^{D3a}$, —$C(=S)OR^{D3a}$, —$C(=S)SR^{D3a}$, —$C(=S)N(R^{D3a})_2$, —$C(=NR^{D3a})R^{D3a}$, —$C(=NR^{D3a})OR^{D3a}$, —$C(=NR^{D3a})SR^{D3a}$, or —$C(=NR^{D3a})N(R^{D3a})_2$ wherein each occurrence of $R^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D3a}$ groups are joined to form an substituted or unsubstituted heterocyclic ring;

optionally $R^{D1}$ and $R^{D3}$, or $R^{D2}$ and $R^{D3}$, or $R^{D1}$ and $R^{D2}$ are joined to form an substituted or unsubstituted carbocyclic or substituted or unsubstituted heterocyclic ring;

$R^{D4}$ is a leaving group selected from the group consisting of —Br, —Cl, —I, and —$OS(=O)_wR^{D4a}$, wherein w is 1 or 2, and $R^{D4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of $X^1$ is independently a bond, —C(=O)—, —S(=O)_2—, $NR^{D5}$, optionally substituted alkylene, or optionally substituted heteroarylene, wherein $R^{D5}$ is hydrogen, $C_{1-6}$ alkyl, or a nitrogen protecting group;

each instance of Y is independently O, S, or $NR^{D6}$, wherein $R^{D6}$ is hydrogen, $C_{1-6}$ alkyl, or a nitrogen protecting group; and each instance of z and $z_1$ is independently 0, 1, 2, 3, 4, 5, or 6, as valency permits.

22. The compound of claim 21, wherein the compound is of Formula (II-a):

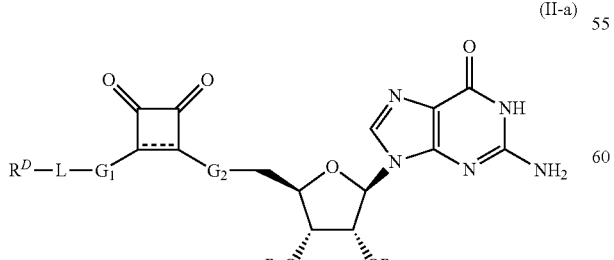

or a pharmaceutically acceptable salt thereof.

23. The compound of claim 21, wherein the compound is of Formula (II-a1):

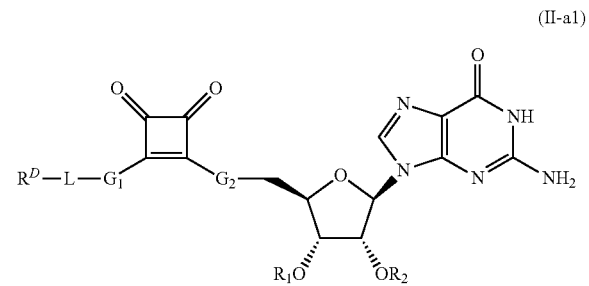

or a pharmaceutically acceptable salt thereof.

24. The compound of claim 21, wherein the compound is of Formula (II-a2):

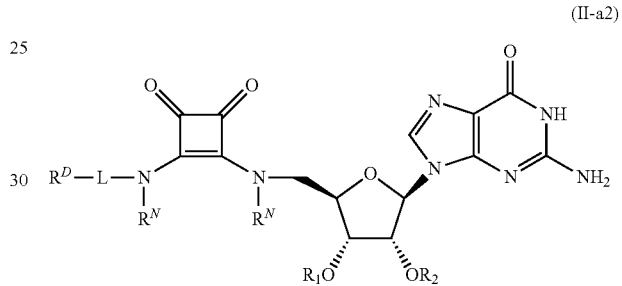

or a pharmaceutically acceptable salt thereof, wherein each instance of $R^N$ is independently hydrogen, optionally substituted alkyl, or a nitrogen protecting group.

25. The compound of claim 21, or a pharmaceutically acceptable salt thereof, wherein L is —$(CH_2)_m$—, wherein m is 1, 2, 3, 4, 5, or 6.

26. The compound of claim 21, or a pharmaceutically acceptable salt thereof, wherein $R_1$ and $R_2$ are taken together with their intervening atoms to form a heterocyclic ring of the formula

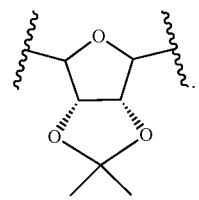 [SMILES: *C1OC(*)[C@@H]2OC(C)(C)O[C@H]12]

27. The compound of claim 21, or a pharmaceutically acceptable salt thereof, wherein $R^D$ is

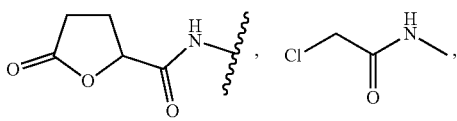

189
-continued

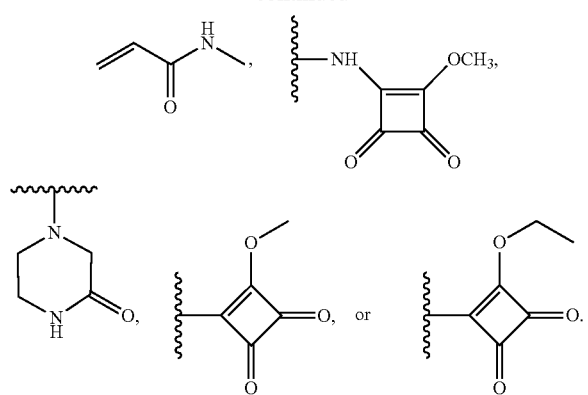

28. The compound of claim 21, wherein the compound is of the formula:

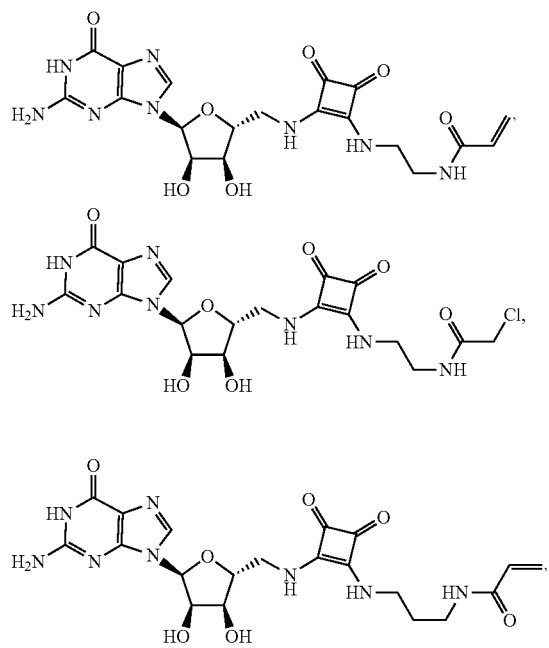

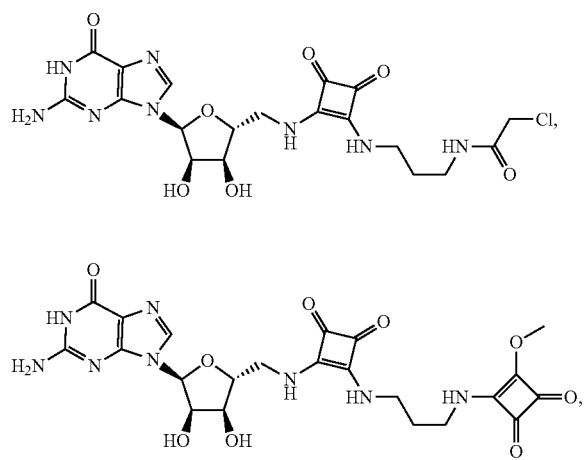

190
-continued
or

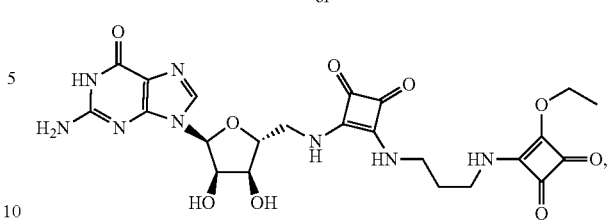

or a pharmaceutically acceptable salt thereof.

29. A pharmaceutical composition comprising a compound of claim 21, or a pharmaceutically acceptable salt thereof, and optionally a pharmaceutically acceptable excipient.

30. The compound of claim 21, or a pharmaceutically acceptable salt thereof, wherein each of $R_1$ and $R_2$ is hydrogen.

31. The compound of claim 21, or a pharmaceutically acceptable salt thereof, wherein $R^D$ is:

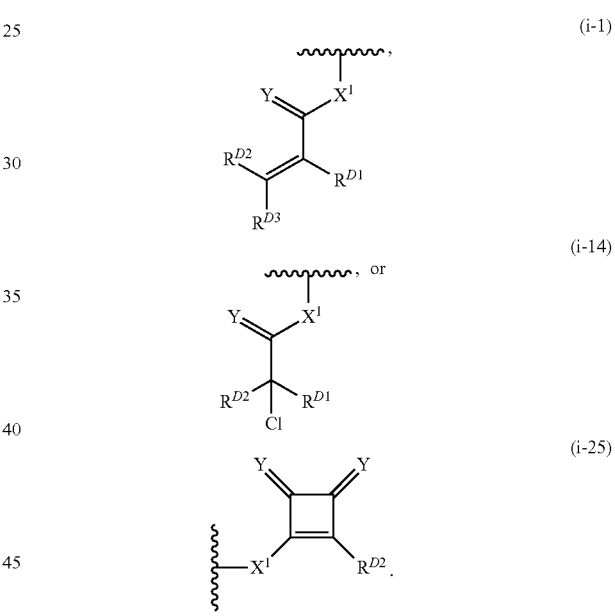

32. A compound of the formula:

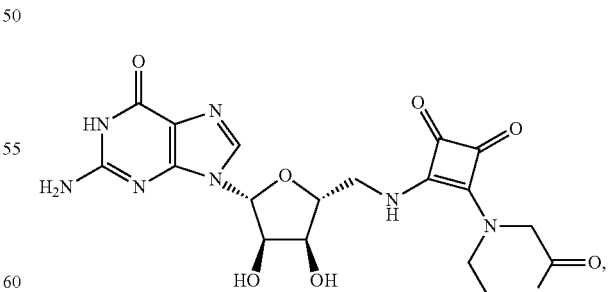

or a pharmaceutically acceptable salt thereof.

33. A pharmaceutical composition comprising a compound of claim 32, or a pharmaceutically acceptable salt thereof, and optionally a pharmaceutically acceptable excipient.

34. A method of treating a proliferative disease in a subject, the method comprising:
   administering to the subject a therapeutically effective amount of a compound of claim 1, or a pharmaceutically acceptable salt thereof.

35. A method of inhibiting Ras activity in a biological sample, the method comprising:
   contacting the biological sample with a therapeutically effective amount of a compound of claim 1, or a pharmaceutically acceptable salt thereof.

36. A method of inhibiting cell growth in a biological sample or subject, the method comprising:
   administering to the subject or contacting the biological sample with a therapeutically effective amount of a compound of claim 1, or a pharmaceutically acceptable salt thereof.

37. A method of inducing apoptosis of a cell in a subject or biological sample, the method comprising:
   administering to the subject or contacting the biological sample with a therapeutically effective amount of a compound of claim 1, or a pharmaceutically acceptable salt thereof.

38. A method of treating a proliferative disease in a subject, the method comprising administering to the subject a therapeutically effective amount of a compound of claim 32, or a pharmaceutically acceptable salt thereof.

39. A method of treating a proliferative disease in a subject, the method comprising administering to the subject a therapeutically effective amount of a compound of claim 21, or a pharmaceutically acceptable salt thereof.

* * * * *

UNITED STATES PATENT AND TRADEMARK OFFICE
CERTIFICATE OF CORRECTION

PATENT NO. : 10,723,753 B2
APPLICATION NO. : 14/775162
DATED : July 28, 2020
INVENTOR(S) : Gray et al.

Page 1 of 5

It is certified that error appears in the above-identified patent and that said Letters Patent is hereby corrected as shown below:

In the Claims

In Claim 11, at Column 177, Line 2, the text: "Formula (I- or (I-e2)" should be replaced with: --Formula (I-e1) or (I-e2)--.

In Claim 17, at Column 181, Lines 1-10, formula:

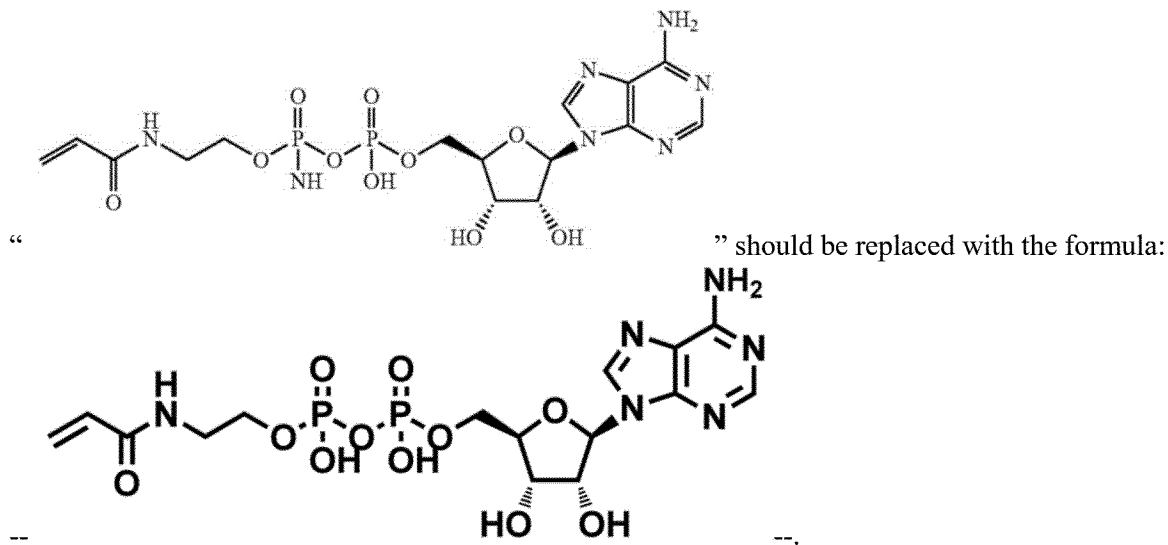

" should be replaced with the formula:

In Claim 17, at Column 181, Lines 12-19, formula:

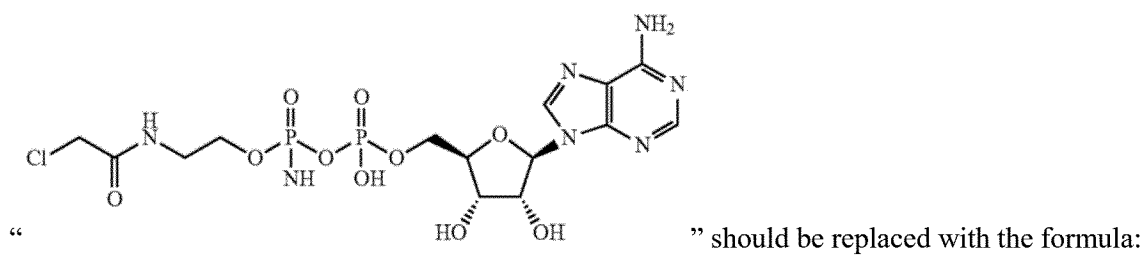

" should be replaced with the formula:

Signed and Sealed this
First Day of December, 2020

Andrei Iancu
*Director of the United States Patent and Trademark Office*

CERTIFICATE OF CORRECTION (continued)
U.S. Pat. No. 10,723,753 B2

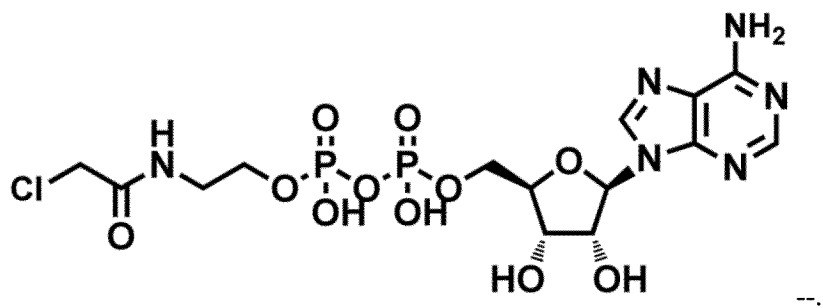
-- --.

In Claim 27, at Column 188, Lines 61-67, formula: " 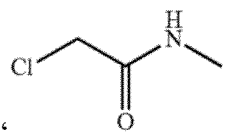 " should be replaced with the formula: -- 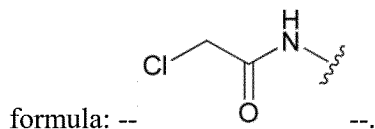 --.

In Claim 27, at Column 189, Lines 1-7, formula: "  " should be replaced with the formula: -- 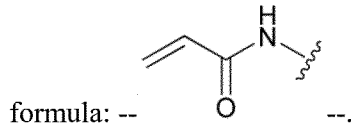 --.

In Claim 28, at Column 189, Lines 20-29, formula:

" 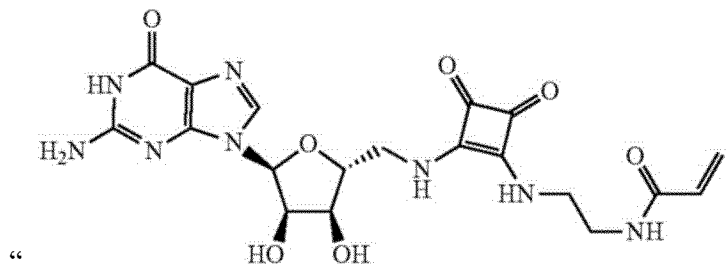 " should be replaced with the formula:

CERTIFICATE OF CORRECTION (continued)
U.S. Pat. No. 10,723,753 B2

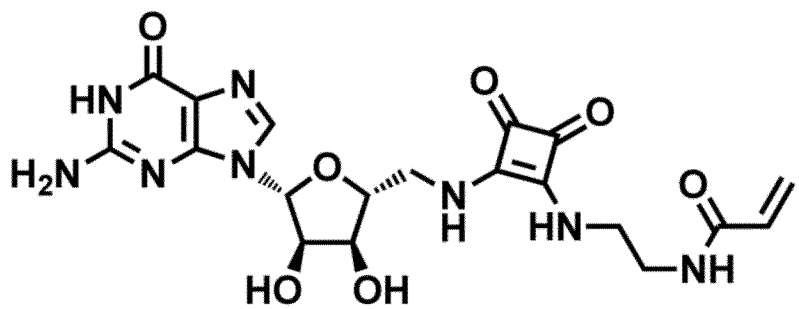

-- --.

In Claim 28, at Column 189, Lines 30-38, formula:

" 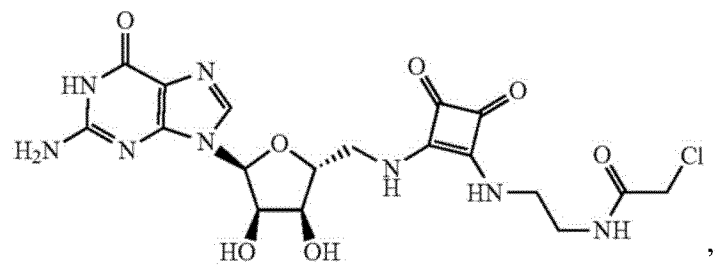 " should be replaced with the formula:

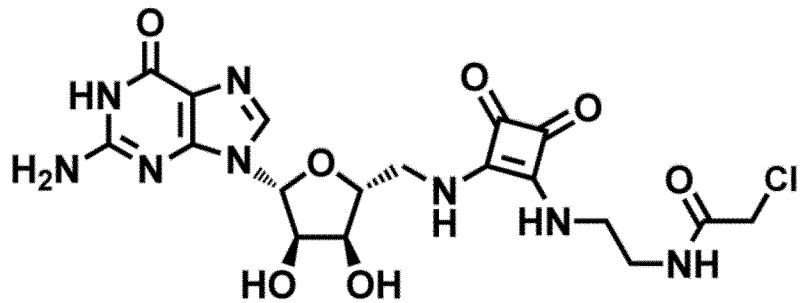

-- --.

In Claim 28, at Column 189, Lines 39-47, formula:

" 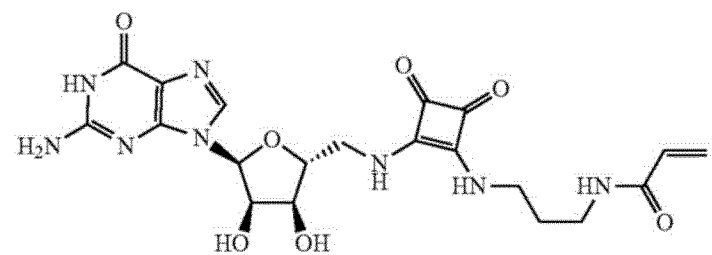 " should be replaced with the formula:

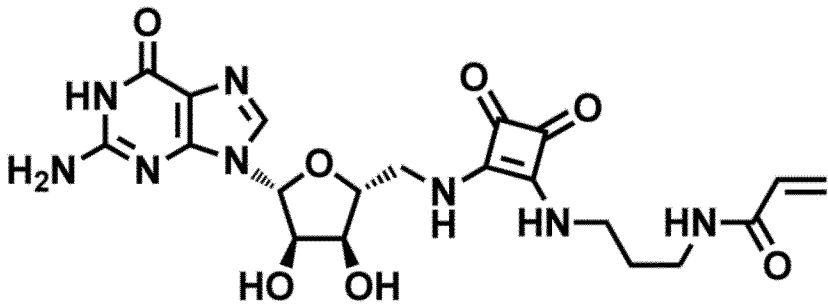

-- --.

In Claim 28, at Column 189, Lines 48-57, formula:
" 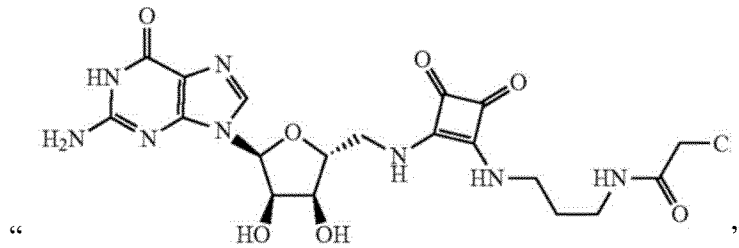 " should be replaced with the formula:
-- 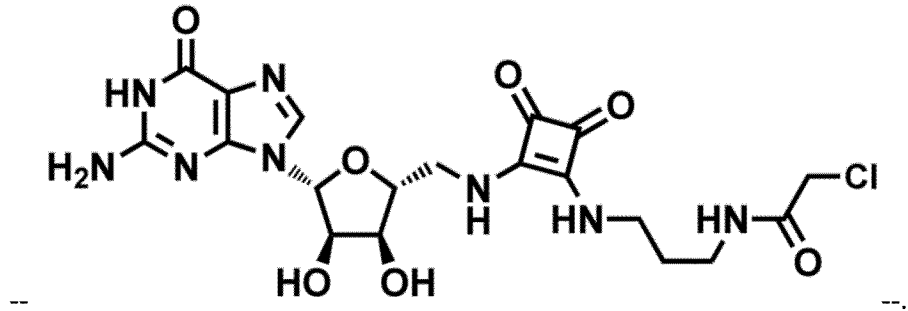 --.
In Claim 28, at Column 189, Lines 58-66, formula:
" 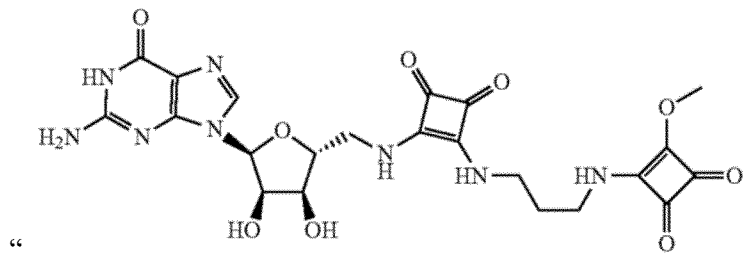 " should be replaced with the formula: -
- 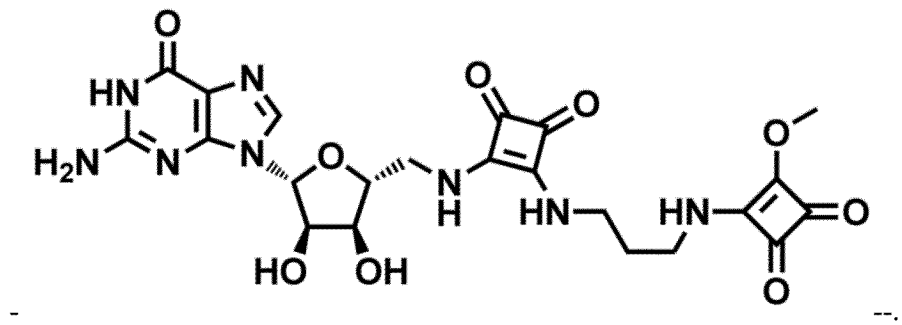 --.
In Claim 28, at Column 190, Lines 1-11, formula:
" 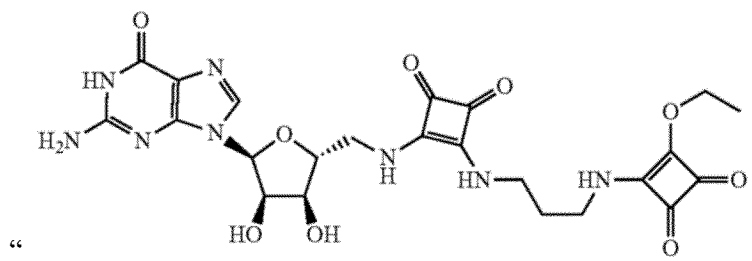 " should be replaced with the formula:

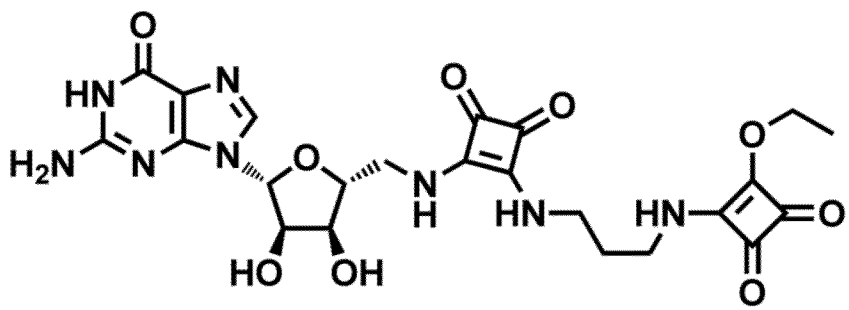
-- -- .